(12) United States Patent
Carry et al.

(10) Patent No.: US 6,699,895 B2
(45) Date of Patent: Mar. 2, 2004

(54) 2-AMINOTHIAZOLINE DERIVATIVES AND PROCESS FOR PREPARING THE SAME

(75) Inventors: Jean-Christophe Carry, Saint Maur des Fosses (FR); Dominique Damour, Orly (FR); Claude Guyon, Saint Maur des Fosses (FR); Serge Mignani, Chatenay-Malabry (FR); Antony Bigot, Massy (FR); Eric Bacque, Morsang sur Orge (FR); Michel Tabart, La Norville (FR)

(73) Assignee: Aventis Pharma S.A., Antony (FR)

( * ) Notice: Subject to any disclaimer, the term of this patent is extended or adjusted under 35 U.S.C. 154(b) by 60 days.

(21) Appl. No.: 10/159,498

(22) Filed: May 31, 2002

(65) Prior Publication Data

US 2002/0198243 A1 Dec. 26, 2002

Related U.S. Application Data

(62) Division of application No. 09/878,814, filed on Jun. 8, 2001, now Pat. No. 6,451,821.
(60) Provisional application No. 60/232,038, filed on Sep. 12, 2000.

(30) Foreign Application Priority Data

Jun. 9, 2000 (FR) ............................................. 00 07397

(51) Int. Cl.$^7$ ...................... C07D 417/06; A61K 31/427
(52) U.S. Cl. ........................ 514/370; 548/193; 548/198
(58) Field of Search ................................ 518/193, 198; 514/370

(56) References Cited

U.S. PATENT DOCUMENTS

| 5,066,662 A | 11/1991 | Hobbs et al. |
| 5,089,512 A | 2/1992 | Wilson et al. |
| 6,001,855 A | 12/1999 | Alig et al. |
| 6,011,028 A | 1/2000 | Hansen, Jr. et al. |

FOREIGN PATENT DOCUMENTS

| WO | WO 94/12165 | 6/1994 |
| WO | WO 95/11231 | 4/1995 |
| WO | WO 96/14842 | 5/1996 |
| WO | WO 01/47931 | 7/2001 |

OTHER PUBLICATIONS

A. J. Little et al., Preparation of Certain Optically Active Semicarbazldes and a Resolution of Benzoln, Journal Chem. Soc. (1940, pp. 336–338).
Benjamin Frydman et al., 1,4–Diaminobutanes From Furans: A new Synthetic Approach to Substituted Putrescines, Tetrahedron letters (1998, pp. 4765–4768, vol. 39).
Jean M. Defauw et al., Synthesis and Protein Kinase C. Inhibitory Activities of Acyclic Balanol Analogs That are Highly Selective for Protein Kinase C. over Protein Kinase A, J. Med. Chem. (1996, pp. 5215–5227, vol. 39).
Timothy D. Ocain et al., Synthesis of Sulfur–Containing Analogues of bestatin., Journal of Medicinal Chemistry (1988, pp. 2193–2199, vol. 31 No. 11).
Odile E. Levy et al., Potent and Selective Thrombin Inhibitors Incorporating the Constrained Arginine Mimic L–3–Piperidy(N–Guanldino)Alanine at P1, Journal of Medicinal Chemistry (1996, pp. 4527–4530, vol. 39 No. 23).
Robert J. Dummel et al., Salicytates of 2–Guanidyl–3–Methybutane–thiol and 2–Amino–5–Hexylthlazoline, Journal of Organic Chemistry ( 1962, pp. 1049, vol. 27 No. 3).
Ronald A. Wohl et al., The Stereochemistry of Azlridine Ring Expansion Reactions with Sulfur Nucleophiles to Give Thiazolidines and 2–Amino–Thiazolines, Journal Org. Chem. (1972, pp. 4401–4406, vol. 37 No. 26).
Salvador Moncada et al., Biosynthesis of Nitric Oxide From L–Arginine, Biochemical Pharmacology (1989, pp. 1709–1715, vol. 38 No. 11).
Yasuyuki Endo et al., Synthesis, Conformation, and Biological Activity of Teleocidin Mimica, Benzolactams. A Clarification of the Conformational Flexibility Problem in Structure–Activity Studies of Teleocidins, Journal Am. Chem. Soc. (1996, pp. 1841–1855, vol. 118).
Xianqi, Feng et al., Synthesis of (S,S)–isodityrosinol in a Fully Differentiated Form via Diels–Alder Methodology, Journal Org. Chem. (1992, pp. 5811–5812, vol. 57).

Primary Examiner—Robert Gerstl
(74) Attorney, Agent, or Firm—James W. Bolcsak

(57) ABSTRACT

The present invention relates to a class of 2-aminothiazoline derivatives of formula I:

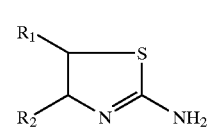

(I)

in which either $R_1$ is a hydrogen atom or an alkyl radical and $R_2$ is an alkyl, -alk-$NH_2$, —$CH_2$—$R_3$, —$CH_2$—S—$R_4$ or phenyl radical substituted with a nitro or —NH—C(=NH)$CH_3$ radical, or $R_1$ is an alkyl radical and $R_2$ is a hydrogen atom, $R_3$ is a (3-6C) cycloalkyl, pyridyl, pyridyl N-oxide, thienyl, thiazolyl, imidazolyl, pyrazinyl, triazolyl or phenyl radical or a phenyl radical substituted with a nitro, hydroxy or carboxyl radical, $R_4$ represents a pyridyl or pyridyl N-oxide radical, alk represents an alkylene radical, or pharmaceutically acceptable salts thereof, which are useful as inhibitors of inducible NO-synthase.

21 Claims, No Drawings

2-AMINOTHIAZOLINE DERIVATIVES AND PROCESS FOR PREPARING THE SAME

This application is a division of U.S. application Ser. No. 09/878,814, filed Jun. 8, 2001, now U.S. Pat. No. 6,451,821, which claims the benefit of U.S. Provisional Application No. 60/232,038, filed Sep. 12, 2000, which claims the benefit of priority of French Patent Application No. 00/07,397, filed Jun. 09, 2000.

The present invention relates to the use of 2-aminothiazoline derivatives of formula (I):

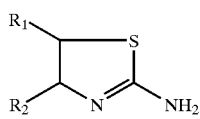

or pharmaceutically acceptable salts thereof, as inhibitors of inducible NO-synthase.

The subject of the invention is the use of 2-aminothiazoline derivatives of formula (I) and pharmaceutically acceptable salts thereof, for the preparation of pharmaceutical compositions intended for preventing and treating diseases in which an abnormal production of nitric oxide (NO) by induction of inducible NO-synthase (NOS-2 or iNOS) is involved, the pharmaceutical compositions containing the novel 2-aminothiazoline derivatives and the pharmaceutically acceptable salts thereof, and the novel 2-aminothiazoline derivatives and the pharmaceutically acceptable salts thereof.

Nitric oxide (NO) is a diffusable radical involved in many physiological and pathological processes. It is synthesized by oxidation of L-arginine, this reaction being catalyzed by a family of enzymes known as nitric oxide synthases or NO-synthases (NOSs), which is referenced in the international enzyme nomenclature system under the number E.C. 1.14.13.39.

Three NOS isoforms, two of which are constitutive and one inducible, are known:
- a neuronal NOS (NOS-1 or NNOS) was originally isolated and cloned from nerve tissue in which it is a constitutive enzyme. NOS-1 produces NO in response to various physiological stimuli such as the activation of membrane receptors according to a mechanism dependent on calcium and on calmodulin;
- an inducible NOS (NOS-2 or iNOS) can be induced in response to immunological stimuli such as, for example, cytokines or bacterial antigens in various cells such as, for example, macrophages, endothelial cells, hepatocytes, glial cells, as well as many other types of cell. The activity of this isoform is not regulated by calcium. Consequently, once induced, it produces large amounts of NO over prolonged periods.
- an endothelial NOS (NOS-3 or eNOS) is constitutive and calcium/calmodulin-dependent. It was originally identified in vascular endothelial cells, in which it generates NO in response to physiological stimuli such as the activation of membrane receptors.

The NO produced by the neuronal and endothelial constitutive isoforms (NOS-1 and NOS-3) is generally involved in intercellular signalling functions. For example, the endothelial cells which line the inner wall of the blood vessels induce the relaxation of the underlying smooth muscle cells via the production of NO. It thus contributes towards regulating the arterial pressure.

The NO produced in large amount by the inducible isoform NOS-2 is, inter alia, involved in pathological phenomena associated with acute and chronic inflammatory processes in a large variety of tissues and organs.

An excessive production of NO by induction of NOS-2 thus plays a part in degenerative pathologies of the nervous system such as, for example, multiple sclerosis, cerebral, focal or global ischemia, cerebral or spinal trauma, Parkinson's disease, Huntington's disease, Alzheimer's disease, amiotrophic lateral sclerosis, migraine, depression, schizophrenia, anxiety and epilepsy. Similarly, aside from the central nervous system, the induction of NOS-2 is involved in numerous pathologies with inflammatory components, such as, for example, diabetes, atherosclerosis, myocarditis, arthritis, arthrosis, asthma, irritable bowel syndrome, Crohn's disease, peritonitis, gastro-esophageal reflux, uveitis, Guillain-Barré syndrome, glomerulonephritis, lupus erythematosus and psoriasis. NOS-2 has also been implicated in the growth of certain forms of tumors such as, for example, epitheliomas, adenocarcinoma or sarcoma, and in infections with Gram-positive or Gram-negative intracellular or extracellular bacteria.

In all the situations in which an overproduction of NO is deleterious, it thus appears to be desirable to reduce the production of NO by administering substances capable of inhibiting NOS-2. However, given the important physiological roles played by the constitutive isoform NOS-3, in particular in regulating arterial pressure, it is of fundamental importance that the inhibition of the isoform NOS-2 should have the least possible effect on the isoform NOS-3. The reason for this is that it is known that the administration of unselective inhibitors of the NOS isoforms leads to vasoconstriction and an increase in arterial pressure (Moncada, S., Palmer, R. M. J. and Higgs, E. A., Biosynthesis of nitric oxide from L-arginine: a pathway for the regulation of cell function and communication, *Biochem. Pharmacol.,* 1989, 38: 1709–1715). These effects on the cardiovascular system are deleterious since they reduce the supply of nutrients to the tissues. Consequently, the present invention relates to compounds whose inhibitory activity with respect to NOS-2 is significantly higher than their inhibitory activity with respect to NOS-3.

Thiazoline-based NOS inhibitors are described in particular in patent applications WO 94/12165, WO 95/11231 and WO 96/14842.

The present invention relates to the use of 2-aminothiazoline derivatives of formula (I) in which: either $R_1$ is a hydrogen atom or an alkyl radical and $R_2$ is an alkyl, -alk-$NH_2$, —$CH_2$—$R_3$, —$CH_2$—S—$R_4$ or phenyl radical substituted with a nitro or —NH—C(=NH)$CH_3$ radical, or $R_1$ is an alkyl radical and $R_2$ is a hydrogen atom, $R_3$ is a (3-6C) cycloalkyl, pyridyl, pyridyl N-oxide, thienyl, thiazolyl, imidazolyl, pyrazinyl, triazolyl or phenyl radical or a phenyl radical substituted with a nitro or carboxyl radical, $R_4$ represents a pyridyl or pyridyl N-oxide radical, alk represents an alkylene radical for the preparation of medicinal products that are useful for preventing or treating diseases in which an abnormal production of nitric oxide (NO) by induction of inducible NO-synthase (NOS-2 or iNOS) is involved.

In the above definitions and in those which follow, the alkyl and alkylene radicals contain 1 to 6 carbon atoms in a straight or branched chain.

The compounds of formula (I) contain one or more asymmetric carbons and can thus be in racemic form or in the form of enantiomers and diastereoisomers; these also form part of the invention, along with mixtures thereof.

Moreover, the compounds of formula (I) can be in the tautomeric form (Ia):

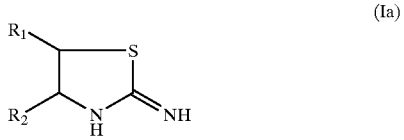

These tautomers also form part of the invention.

Among the compounds of formula (I) that are useful according to the invention, mention may be made of the following compounds:
4-(3-pyridylmethyl)-4,5-dihydro-1,3-thiazol-2-ylamine
4-(3-nitrobenzyl)-4,5-dihydro-1,3-thiazol-2-ylamine
4-benzyl-5-methyl-4,5-dihydro-1,3-thiazol-2-ylamine
4-(3-thienylmethyl)-4,5-dihydro-1,3-thiazol-2-ylamine
4-(2-thienylmethyl)-4,5-dihyro-1,3-thiazol-2-ylamine
[3-(2-amino-4,5-dihydrothiazol-4-yl)phenyl](1-iminoethyl) amine
4-benzyl-4,5-dihydro-1,3-thiazol-2-ylamine
4-(3-carboxybenzyl)-4,5-dihydro-1,3-thiazol-2-ylamine
4-(4-aminobutyl)-4,5-dihydro-1,3-thiazol-2-ylamine
4-butyl-4,5-dihydro-1,3-thiazol-2-ylamine
5-methyl-4,5-dihydro-1,3-thiazol-2-ylamine
4-cyclohexylmethyl-4,5-dihydro-1,3-thiazol-2-ylamine
4-(3-nitrophenyl)-4,5-dihydro-1,3-thiazol-2-ylamine
4-(4-pyridylmethyl)-4,5-dihydro-1,3-thiazol-2-ylamine
5-methyl-4-(4-pyridylmethyl)-4,5-dihydro-1,3-thiazol-2-ylamine
5-ethyl-4-(4-pyridylmethyl)-4,5-dihydro-1,3-thiazol-2-ylamine
4-(4-thiazolylmethyl)-4,5-dihydro-1,3-thiazol-2-ylamine
4-(1-imidazolylmethyl)-4,5-dihydro-1,3-thiazol-2-ylamine
4-(2-pyrazinylmethyl)-4,5-dihydro-1,3-thiazol-2-ylamine
4-(5-thiazolylmethyl)-4,5-dihydro-1,3-thiazol-2-ylamine
4-(4-hydroxybenzyl)-4,5-dihydro-1,3-thiazol-2-ylamine
4-(4-pyridylsulphanylmethyl)-4,5-dihydro-1,3-thiazol-2-ylamine
4-(3-aminopropyl)-4,5-dihydro-1,3-thiazol-2-ylamine
4-(1-triazolylmethyl)-4,5-dihydro-1,3-thiazol-2-ylamine
4-(4-pyridylmethyl)-4,5-dihydro-1,3-thiazol-2-ylamine N-oxide
the racemic mixtures, enantiomers, diastereoisomers and tautomers thereof, as well as the pharmaceutically acceptable salts thereof, and most particularly the following compounds:
(+)-(4R)-4-(3-pyridylmethyl)-4,5-dihydro-1,3-thiazol-2-ylamine
(+)-(4R)-4-(3-nitrobenzyl)-4,5-dihydro-1,3-thiazol-2-ylamine
(+)-(4R,5S)-4-benzyl-5-methyl-4,5-dihydro-1,3-thiazol-2-ylamine
(+)-(4R,5R)-4-benzyl-5-methyl-4,5-dihydro-1,3-thiazol-2-ylamine
(−)-(4R)-4-(3-thienylmethyl)-4,5-dihydro-1,3-thiazol-2-ylamine
(4R)-4-(2-thienylmethyl)-4,5-dihydro-1,3-thiazol-2-ylamine
[3-(2-amino-4,5-dihydrothiazol-4-yl)phenyl](1-iminoethyl) amine
(+)-(4R)-4-benzyl-4,5-dihydro-1,3-thiazol-2-ylamine
(+)-(4R)-4-(3-carboxybenzyl)-4,5-dihydro-1,3-thiazol-2-ylamine
(+)-(4R)-4-(4-aminobutyl)-4,5-dihydro-1,3-thiazol-2-ylamine
(−)-(4S)-4-(3-nitrobenzyl)-4,5-dihydro-1,3-thiazol-2-ylamine
(−)-(4S,5S)-4-benzyl-5-methyl-4,5-dihydro-1,3-thiazol-2-ylamine
(−)-(4S)-4-(4-aminobutyl)-4,5-dihydro-1,3-thiazol-2-ylamine
(4S,5R)-4-benzyl-5-methyl-4,5-dihydro-1,3-thiazol-2-ylamine
(−)-(4R)-4-butyl-4,5-dihydro-1,3-thiazol-2-ylamine
(+)-(5S)-5-methyl-4,5-dihydro-1,3-thiazol-2-ylamine
(−)-(4S)-4-cyclohexylmethyl-4,5-dihydro-1,3-thiazol-2-ylamine
(+)-(4R)-4-cyclohexylmethyl-4,5-dihydro-1,3-thiazol-2-ylamine
4-(3-nitrophenyl)-4,5-dihydro-1,3-thiazol-2-ylamine
(+)-(4R)-4-(4-pyridylmethyl)-4,5-dihydro-1,3-thiazol-2-ylamine
(+)-(4R,5R)-5-methyl-4-(4-pyridylmethyl)-4,5-dihydro-1,3-thiazol-2-ylamine
(+)-(4R,5R)-5-ethyl-4-(4-pyridylmethyl)-4,5-dihydro-1,3-thiazol-2-ylamine
(+)-4-(5-thiazolylmethyl)-4,5-dihydro-1,3-thiazol-2-ylamine
(−)-4-(5-thiazolylmethyl)-4,5-dihydro-1,3-thiazol-2-ylamine
(+)-(4R)-4-(2-pyrazinylmethyl)-4,5-dihydro-1,3-thiazol-2-ylamine
(4R)-4-(1-imidazolylmethyl)-4,5-dihydro-1,3-thiazol-2-ylamine
(4S)-4-(1-imidazolylmethyl)-4,5-dihydro-1,3-thiazol-2-ylamine
(+)-(4R)-4-(4-thiazolylmethyl)-4,5-dihydro-1,3-thiazol-2-ylamine
(+)-(4R)-4-(3-aminopropyl)-4,5-dihydro-1,3-thiazol-2-ylamine
(+)-(4R)-4-(4-hydroxybenzyl)-4,5-dihydro-1,3-thiazol-2-ylamine
(+)-(4-(4-pyridylsulphanylmethyl)-4,5-dihydro-1,3-thiazol-2-ylamine
(4R)-4-(4-pyridylmethyl)-4,5-dihydro-1,3-thiazol-2-ylamine N-oxide
(+)-4-(1-triazolylmethyl)-4,5-dihydro-1,3-thiazol-2-ylamine
the tautomers thereof, as well as the pharmaceutically acceptable salts thereof.

The compounds which are particularly preferred are the useful compounds of formula (I) according to the invention for which $R_1$ is a hydrogen atom or an alkyl radical and $R_2$ is an -alk-$NH_2$ radical or a phenyl radical substituted with an —NH—C(=NH)$CH_3$, —$CH_2$—$R_3$ or —$CH_2$—S—$R_4$ radical and $R_3$ is a pyridyl, thienyl, thiazolyl, imidazolyl, pyrazinyl, triazolyl or phenyl radical or phenyl radical substituted with a nitro or carboxyl radical, $R_4$ is a pyridyl radical.

In particular, when $R_2$ is a —$CH_2$—$R_3$ or —$CH_2$—S—$R_4$ chain, $R_3$ is a 3- or 4-pyridyl, 2- or 3-thienyl, 4- or 5-thiazolyl, 1-imidazolyl, 1-triazolyl, 2-pyrazinyl or phenyl radical or a phenyl radical substituted in position −3 with a nitro or carboxyl radical and $R_4$ is a 4-pyridyl radical.

Among the compounds which are useful according to the invention and particularly preferred, mention may be made of the following compounds:

4-(3-pyridylmethyl)-4,5-dihydro-1,3-thiazol-2-ylamine
4-(3-nitrobenzyl)-4,5-dihydro-1,3-thiazol-2-ylamine
4-benzyl-5-methyl-4,5-dihydro-1,3-thiazol-2-ylamine
4-(3-thienylmethyl)-4,5-dihydro-1,3-thiazol-2-ylamine
4-(2-thienylmethyl)-4,5-dihyro-1,3-thiazol-2-ylamine
[3-(2-amino-4,5-dihydrothiazol-4-yl)phenyl](1-iminoethyl)amine
4-benzyl-4,5-dihydro-1,3-thiazol-2-ylamine
4-(3-carboxybenzyl)-4,5-dihydro-1,3-thiazol-2-ylamine
4-(4-aminobutyl)-4,5-dihydro-1,3-thiazol-2-ylamine
4-(4-pyridylmethyl)-4,5-dihydro-1,3-thiazol-2-ylamine
5-methyl-4-(4-pyridylmethyl)-4,5-dihydro-1,3-thiazol-2-ylamine
5-ethyl-4-(4-pyridylmethyl)-4,5-dihydro-1,3-thiazol-2-ylamine
4-(4-thiazolylmethyl)-4,5-dihydro-1,3-thiazol-2-ylamine
4-(1-imidazolylmethyl)-4,5-dihydro-1,3-thiazol-2-ylamine
4-(2-pyrazinylmethyl)-4,5-dihydro-1,3-thiazol-2-ylamine
4-(5-thiazolylmethyl)-4,5-dihydro-1,3-thiazol-2-ylamine
4-(4-pyridylsulphanylmethyl)-4,5-dihydro-1,3-thiazol-2-ylamine
4-(1-triazolylmethyl)-4,5-dihydro-1,3-thiazol-2-ylamine
the racemic mixtures, enantiomers, diastereoisomers and tautomers thereof, as well as the pharmaceutically acceptable salts thereof, and in particular the following compounds:
(+)-(4R)-4-(3-pyridylmethyl)-4,5-dihydro-1,3-thiazol-2-ylamine
(+)-(4R)-4-(3-nitrobenzyl)-4,5-dihydro-1,3-thiazol-2-ylamine
(+)-(4R,5S)-4-benzyl-5-methyl-4,5-dihydro-1,3-thiazol-2-ylamine
(+)-(4R,5R)-4-benzyl-5-methyl-4,5-dihydro-1,3-thiazol-2-ylamine
(−)-(4R)-4-(3-thienylmethyl)-4,5-dihydro-1,3-thiazol-2-ylamine
(4R)-4-(2-thienylmethyl)-4,5-dihydro-1,3-thiazol-2-ylamine
[3-(2-amino-4,5-dihydrothiazol-4-yl)phenyl](1-iminoethyl)amine
(+)-(4R)-4-benzyl-4,5-dihydro-1,3-thiazol-2-ylamine
(+)-(4R)-4-(3-carboxybenzyl)-4,5-dihydro-1,3-thiazol-2-ylamine
(+)-(4R)-4-(4-aminobutyl)-4,5-dihydro-1,3-thiazol-2-ylamine
(−)-(4S)-4-(3-nitrobenzyl)-4,5-dihydro-1,3-thiazol-2-ylamine
(−)-(4S,5S)-4-benzyl-5-methyl-4,5-dihydro-1,3-thiazol-2-ylamine
(−)-(4S)-4-(4-aminobutyl)-4,5-dihydro-1,3-thiazol-2-ylamine
(4S,5R)-4-benzyl-5-methyl-4,5-dihydro-1,3-thiazol-2-ylamine
(+)-(4R)-4-(4-pyridylmethyl)-4,5-dihydro-1,3-thiazol-2-ylamine
(+)-(4R,5R)-5-methyl-4-(4-pyridylmethyl)-4,5-dihydro-1,3-thiazol-2-ylamine
(+)-(4R,5R)-5-ethyl-4-(4-pyridylmethyl)-4,5-dihydro-1,3-thiazol-2-ylamine
(+)-4-(5-thiazolylmethyl)-4,5-dihydro-1,3-thiazol-2-ylamine
(−)-4-(5-thiazolylmethyl)-4,5-dihydro-1,3-thiazol-2-ylamine
(+)-(4R)-4-(2-pyrazinylmethyl)-4,5-dihydro-1,3-thiazol-2-ylamine
(4R)-4-(1-imidazolylmethyl)-4,5-dihydro-1,3-thiazol-2-ylamine
(4S)-4-(1-imidazolylmethyl)-4,5-dihydro-1,3-thiazol-2-ylamine
(+)-(4R)-4-(4-thiazolylmethyl)-4,5-dihydro-1,3-thiazol-2-ylamine
(+)-4-(4-pyridylsulphanylmethyl)-4,5-dihydro-1,3-thiazol-2-ylamine
(+)-4-(1-triazolylmethyl)-4,5-dihydro-1,3-thiazol-2-ylamine
the tautomers thereof, as well as the pharmaceutically acceptable salts thereof.

The compounds of formula (I) for which $R_1$ is methyl or hexyl and $R_2$ is hydrogen or else $R_1$ and $R_2$ are methyl are known as chemical products (J. Org. Chem., 27, 1049 (1962); J. Org. Chem., 37, 4401 (1972); Beilstein Registry Numbers 6114855, 6114856, 6117694, 6117695).

Moreover, certain compounds of formula (I) are known as radioprotective agents. These are the racemic compounds for which $R_1$ is a methyl radical and $R_2$ is a hydrogen atom (Chem. Abst., 1980, 92, 209060 and 209061), $R_1$ is hydrogen and $R_2$ is methyl (Chem. Abst., 1997, 87, 193910), $R_1$ is hydrogen and $R_2$ is ethyl (Khim. Geterotsikl. Soedin, 1987, 11, 1572), $R_1$ is hydrogen and $R_2$ is n-propyl (Radiobiologiya, 1979, 19 (5), 671).

The other compounds of formula (I) are novel and, as such, they form part of the invention, as do the racemic mixtures, enantiomers, diastereoisomers and tautomers thereof and the pharmaceutically acceptable salts thereof.

These are the compounds for which either $R_1$ is a hydrogen atom or an alkyl radical and $R_2$ is an alkyl, -alk-$NH_2$, —$CH_2$—$R_3$ or —$CH_2$—S—$R_4$ radical or a phenyl radical substituted with a nitro or —NH—C(=NH)$CH_3$ radical, or $R_1$ is an alkyl radical and $R_2$ is a hydrogen atom, $R_3$ is a cycloalkyl (3-6C), pyridyl, thienyl, thiazolyl, imidazolyl, pyrazinyl, triazolyl or phenyl radical or a phenyl radical substituted with a nitro, hydroxyl or carboxyl radical, $R_4$ represents a pyridyl radical, alk represents an alkylene radical, the racemic mixtures, enantiomers and diastereoisomers thereof and mixtures thereof, the tautomers thereof and the pharmaceutically acceptable salts thereof, with the exception of the compounds for which $R_1$ is hexyl or methyl and $R_2$ is hydrogen or else $R_1$ and $R_2$ are methyl, and the racemic mixtures of the compounds for which $R_1$ is hydrogen and $R_2$ is methyl, ethyl or n-propyl.

The compounds of formula (I) that are particularly preferred are those for which $R_1$ is a hydrogen atom or an alkyl radical and $R_2$ is an -alk-$NH_2$ radical, a phenyl radical substituted with an —NH—C(=NH)$CH_3$ radical, a radical —$CH_2$—$R_3$ for which $R_3$ is a pyridyl, thienyl, thiazolyl, imidazolyl, triazolyl, pyrazinyl or phenyl radical or a phenyl radical substituted with a nitro or carboxyl radical, or a radical —$CH_2$—S—$R_4$ for which $R_4$ is a pyridyl radical, the racemic mixtures, enantiomers and diastereoisomers thereof and mixtures thereof, the tautomers thereof and the pharmaceutically acceptable salts thereof.

In particular, $R_3$ is a 3- or 4-pyridyl, 2- or 3-thienyl, 4- or 5-thiazolyl, 1-imidazolyl, 1-triazolyl, 2-pyrazinyl or phenyl radical or a phenyl radical substituted in position −3 with a nitro or carboxyl radical and $R_4$ is a 4-pyridyl radical.

Among the novel compounds of formula (I) which may be mentioned are the following compounds:

4-(3-pyridylmethyl)-4,5-dihydro-1,3-thiazol-2-ylamine
4-(3-nitrobenzyl)-4,5-dihydro-1,3-thiazol-2-ylamine
4-benzyl-5-methyl-4,5-dihydro-1,3-thiazol-2-ylamine
4-(3-thienylmethyl)-4,5-dihydro-1,3-thiazol-2-ylamine
4-(2-thienylmethyl)-4,5-dihydro-1,3-thiazol-2-ylamine
4-(4-pyridylmethyl)-4,5-dihydro-1,3-thiazol-2-ylamine
5-methyl-4-(4-pyridylmethyl)-4,5-dihydro-1,3-thiazol-2-ylamine
5-ethyl-4-(4-pyridylmethyl)-4,5-dihydro-1,3-thiazol-2-ylamine
4-(4-thiazolylmethyl)-4,5-dihydro-1,3-thiazol-2-ylamine
4-(1-imidazolylmethyl)-4,5-dihydro-1,3-thiazol-2-ylamine
4-(2-pyrazinylmethyl)-4,5-dihydro-1,3-thiazol-2-ylamine
4-(5-thiazolylmethyl)-4,5-dihydro-1,3-thiazol-2-ylamine
4-(1-triazolylmethyl)-4,5-dihydro-1,3-thiazol-2-ylamine
4-(4-pyridylsulphanylmethyl)-4,5-dihydro-1,3-thiazol-2-ylamine the racemic mixtures, enantiomers, diastereoisomers and tautomers thereof and the pharmaceutically acceptable salts thereof, and in particular the following compounds:
(+)-(4R)-4-(3-pyridylmethyl)-4,5-dihydro-1,3-thiazol-2-ylamine
(+)-(4R)-4-(3-nitrobenzyl)-4,5-dihydro-1,3-thiazol-2-ylamine
(+)-(4R,5S)-4-benzyl-5-methyl-4,5-dihydro-1,3-thiazol-2-ylamine
(+)-(4R,5R)-4-benzyl-5-methyl-4,5-dihydro-1,3-thiazol-2-ylamine
(−)-(4R)-4-(3-thienylmethyl)-4,5-dihydro-1,3-thiazol-2-ylamine
(4R)-4-(2-thienylmethyl)-4,5-dihydro-1,3-thiazol-2-ylamine
[3-(2-amino-4,5-dihydrothiazol-4-yl)phenyl](1-iminoethyl)amine
(+)-(4R)-4-benzyl-4,5-dihydro-1,3-thiazol-2-ylamine
(+)-(4R)-4-(3-carboxybenzyl)-4,5-dihydro-1,3-thiazol-2-ylamine
(+)-(4R)-4-(4-aminobutyl)-4,5-dihydro-1,3-thiazol-2-ylamine
(−)-(4S)-4-(3-nitrobenzyl)-4,5-dihydro-1,3-thiazol-2-ylamine
(−)-(4S,5S)-4-benzyl-5-methyl-4,5-dihydro-1,3-thiazol-2-ylamine
(−)-(4S)-4-(4-aminobutyl)-4,5-dihydro-1,3-thiazol-2-ylamine
(4S,5R)-4-benzyl-5-methyl-4,5-dihydro-1,3-thiazol-2-ylamine
(+)-(4R)-4-(4-pyridylmethyl-4,5-dihydro-1,3-thiazol-2-ylamine
(+)-(4R,5R)-5-methyl-4-(4-pyridylmethyl-4,5-dihydro-1,3-thiazol-2-ylamine
(+)-(4R,5R)-5-ethyl-4-(4-pyridylmethyl-4,5-dihydro-1,3-thiazol-2-ylamine
(4S,5R)-4-benzyl-5-methyl-4,5-dihydro-1,3-thiazol-2-ylamine
(+)-(4R)-4-(4-pyridylmethyl)-4,5-dihydro-1,3-thiazol-2-ylamine
(+)-(4R,5R))-5-methyl)-4-(4-pyridylmethyl)-4,5-dihydro-1,3-thiazol-2-ylamine
(+)-(4R,5R))-5-ethyl)-4-(4-pyridylmethyl)-4,5-dihydro-1,3-thiazol-2-ylamine
(+)-4-(5-thiazolylmethyl)-4,5-dihydro-1,3-thiazol-2-ylamine
(−)-4-(5-thiazolylmethyl)-4,5-dihydro-1,3-thiazol-2-ylamine
(+)-(4R)-4-(2-pyrazinylmethyl)-4,5-dihydro-1,3-thiazol-2-ylamine
(4R)-4-(1-imidazolylmethyl)-4,5-dihydro-1,3-thiazol-2-ylamine
(4S)-4-(1-imidazolylmethyl)-4,5-dihydro-1,3-thiazol-2-ylamine
(+)-(4R)-4-(4-thiazolylmethyl)-4,5-dihydro-1,3-thiazol-2-ylamine
(+)-4-(4-pyridylsulphanylmethyl)-4,5-dihydro-1,3-thiazol-2-ylamine
(+)-4-(1-triazolylmethyl)-4,5-dihydro-1,3-thiazol-2-ylamine the tautomers thereof and the pharmaceutically acceptable salts thereof.

The invention also relates to pharmaceutical compositions containing, as active principle, a derivative of formula (I) for which either $R_1$ is a hydrogen atom or an alkyl radical and $R_2$ is an alkyl, -alk-$NH_2$, —$CH_2$—$R_3$ or —$CH_2$—$S$—$R_4$ radical or a phenyl radical substituted with a nitro or —NH—C(=NH)$CH_3$ radical, or $R_1$ is an alkyl radical and $R_2$ is a hydrogen atom, $R_3$ is a cycloalkyl (3-6C), pyridyl, thienyl, thiazolyl, imidazolyl, pyrazinyl, triazolyl or phenyl radical or a phenyl radical substituted with a nitro, hydroxyl or carboxyl radical, $R_4$ represents a pyridyl radical and alk represents an alkylene radical, as well as the racemic mixtures, enantiomers and diastereoisomers thereof and mixtures thereof, the tautomer thereof and the pharmaceutically acceptable salts thereof, with the exception of the racemic compounds for which $R_1$ is a methyl radical and $R_2$ is a hydrogen atom or else $R_1$ is hydrogen and $R_2$ is methyl, ethyl or n-propyl.

The compounds of formula (I) can be prepared by cyclization of a derivative of formula:

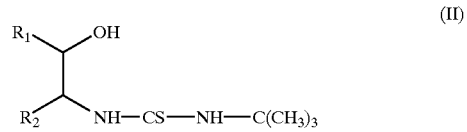

(II)

in which $R_1$ and $R_2$ have the same meanings as in formula (I).

This cyclization is generally carried out using an acid such as hydrochloric acid, in aqueous medium, at a temperature of 100° C. 6N hydrochloric acid is preferably used.

The derivatives of formula (II) can be obtained according to the following reaction schemes: Scheme 1 for the compounds for which $R_1$ is hydrogen

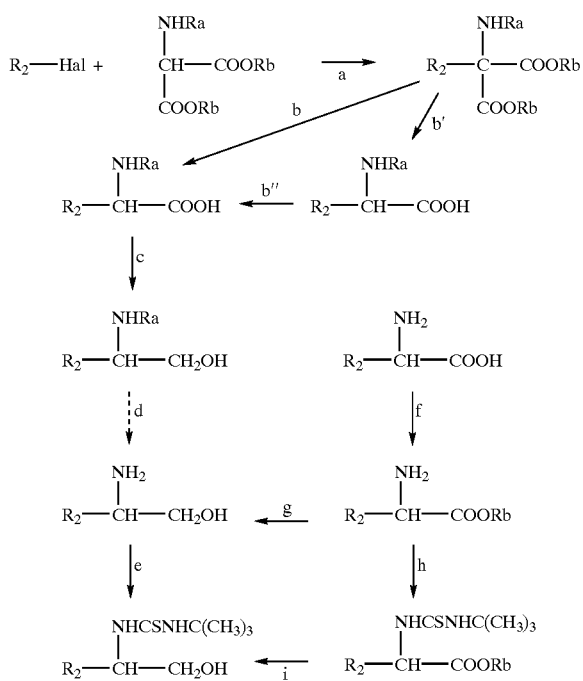

in these formulae $R_2$ has the same meanings as in formula (I), Ra is a hydrogen atom or a protecting group for the amine function, such as those described by T. W. Greene, Protective groups in organic synthesis, J. Wiley-Interscience Publication (1991) and Rb is a (1-4C) alkyl or alkoxycarbonyl radical, preferably methyl, ethyl or isobutyloxycarbonyl. The protecting group for the amine function is preferably an acetyl or tert-butoxycarbonyl radical.

Reaction a is generally carried out in the presence of a sodium (1-4C) alkoxide (preferably sodium ethoxide), in the corresponding alcohol, at a temperature of between 10° C. and the boiling point of the reaction medium.

Reaction b is generally carried out in an inert solvent such as dimethylformamide in the presence of lithium iodide, at a temperature of between 100° C. and the boiling point of the reaction medium, or in a (1-4C) aliphatic alcohol, in the presence of sodium hydroxide, at a temperature from 10° C. to 30° C., followed by neutralizing with 6N HCl then heating in a solvent such as dioxane at a temperature in the region of 100° C.

Reaction b' is preferably carried out using hydrochloric acid, at a temperature of 100° C.

Reaction b" for the derivatives for which Rb is an alkyl radical is generally carried out by the action of a (1-4C) aliphatic alcohol (preferably methanol or ethanol), in the presence of an inorganic acid such as sulfuric acid, at a temperature of between 50° C. and the boiling point of the reaction medium. For the derivatives for which Rb is an isobutyloxycarbonyl radical, this reaction is generally carried out by the action of isobutyl chloroformate in the presence of a base such as triethylamine, in an inert solvent such as tetrahydrofuran, at a temperature of between −20° C. and 0° C.

The reduction reactions c, g and i are preferably carried out using a hydride such as sodium borohydride or lithium aluminum hydride, in a (1-4C) aliphatic alcohol or tetrahydrofuran, at a temperature of between 10° C. and 30° C., or alternatively using a borane derivative such as the $BH_3$-THF complex, in a solvent such as tetrahydrofuran, at a temperature of between 0° C. and 30° C.

The deprotection reaction d for the compounds for which Ra is a protecting group for the amine function is carried out by any deprotection method known to those skilled in the art, and in particular those described by T. W. Greene, Protective groups in organic synthesis, J. Wiley-Interscience Publication (1991). Preferably, when the protecting group is an acetyl radical, this reaction is carried out using aqueous hydrochloric acid, at a temperature of 100° C. When the protecting group is a tert-butoxycarbonyl radical, this reaction is carried out using hydrochloric acid in dioxane, at a temperature in the region of 20° C.

Reactions e and h are carried out by the action of tert-butyl isothiocyanate, in an inert solvent such as a (1-4C) aliphatic alcohol (preferably methanol or ethanol), optionally in the presence of a tertiary amine such as triethylamine, at a temperature of between 20° C. and the boiling point of the reaction medium.

Reaction f is carried out by the action of a (1-4C) aliphatic alcohol (preferably methanol or ethanol), in the presence of an inorganic acid such as hydrochloric acid, at a temperature of between 20° C. and the boiling point of the reaction medium, or alternatively by the action of thionyl chloride, in a (1-4C) aliphatic alcohol (preferably methanol or ethanol), at a temperature of between 25° C. and 30° C. Scheme 2 for the compounds for which $R_1$ is alkyl

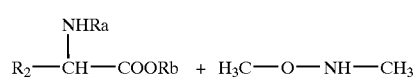

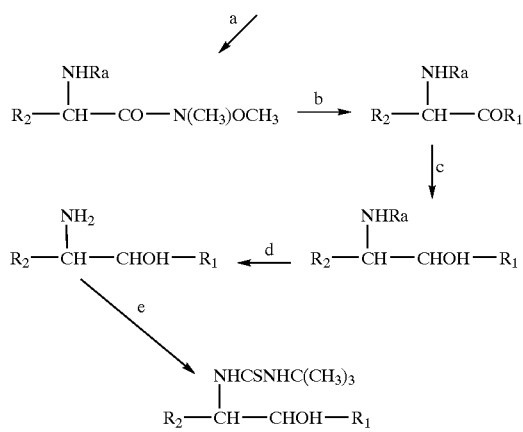

in these formulae $R_1$ and $R_2$ have the same meanings as in formula (I), Ra is a hydrogen atom or a protecting group for the amine function, such as those described by T. W. Greene, Protective groups in organic synthesis, J. Wiley-Interscience Publication (1991) and preferably an acetyl or tert-butoxycarbonyl radical, and Rb is an alkyl or alkoxycarbonyl radical, and preferably methyl, ethyl or isobutyloxycarbonyl.

Reaction a is preferably carried out in an inert solvent such as a chlorinated solvent (for example chloroform or dichloromethane), optionally in the presence of a base such as N-methylmorpholine or triethylamine, at a temperature of between −15° C. and 30° C.

Reaction b is carried out by the action of an alkylmagnesium halide such as an alkylmagnesium bromide, in an ether such as tetrahydrofuran or ethyl ether, at a temperature of between 0° C. and 30° C.

The reduction reaction c is preferably carried out using a hydride such as sodium borohydride or lithium aluminum hydride, in a (1-4C) aliphatic alcohol or tetrahydrofuran, at a temperature of between 10° C. and 30° C., or using a borane derivative such as the BH₃-THF complex, in a solvent such as tetrahydrofuran, at a temperature of between 0° C. and 30° C.

The deprotection reaction d is carried out by any method known to those skilled in the art for deprotecting an amine function, and in particular those described by T. W. Greene, Protective groups in organic synthesis, J. Wiley-Interscience Publication (1991). Preferably, when the protecting group is an acetyl radical, this reaction is carried out using aqueous hydrochloric acid, at a temperature of 100° C. When the protecting group is a tert-butoxycarbonyl radical, this reaction is carried out using hydrochloric acid in dioxane, at a temperature in the region of 20° C.

Reaction e is carried out by the action of tert-butyl isothiocyanate, in an inert solvent such as a (1-4C) aliphatic alcohol (preferably methanol or ethanol), in the presence of a tertiary amine such as triethylamine, at a temperature of between 20° C. and the boiling point of the reaction medium.

The compounds of formula (I) for which $R_2$ is a phenyl radical substituted with an —NH—C(=NH)CH₃ radical can also be prepared from the corresponding amine derivatives which are themselves obtained by reducing the nitro derivatives of formula (I) according to the following scheme:

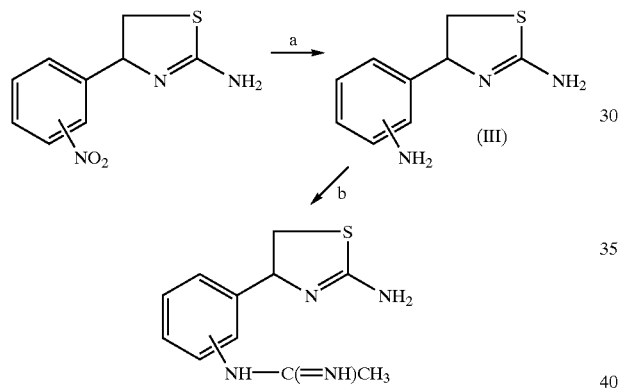

The reduction reaction a is carried out by any reduction method known to those skilled in the art for proceeding from a nitro to an amino without affecting the rest of the molecule. The process is preferably performed using zinc, in acetic acid, at a, temperature in the region of 20° C.

Reaction b is carried out by reaction of benzyl ethanimidothioate hydrochloride, in an inert solvent such as a (1-4C) aliphatic alcohol and preferably methanol or ethanol, at a temperature of between 0° C. and 45° C.

The intermediates of formula (III) are novel and form part of the invention.

The compounds of formula (I) for which $R_2$ is a radical —CH₂—$R_3$ in which $R_3$ is a 1-imidazolyl or 1-(1,2,4-triazolyl) radical may also be prepared by the action of imidazolyl or of 1,2,4-triazole on a derivative of formula:

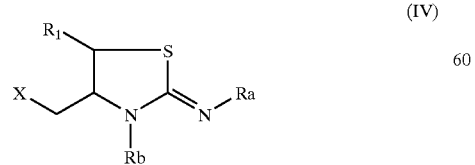

in which $R_1$ has the same meanings as in formula (I), X is a halogen atom, and in particular an iodine atom, or a tosyl radical, Ra and Rb are hydrogen atoms or protecting groups for the amine function such as those described by T. W. Greene, Protective Groups in Organic Synthesis, J. Wiley-Interscience Publication (1991), preferably alkoxycarbonyl or acetyl and more particularly tert-butoxycarbonyl, optionally followed by a deprotection.

This reaction is generally carried out in the presence of a base such as an alkali metal hydride, preferably sodium hydride, in a solvent such as dimethyl sulfoxide, at a temperature of between 20° C. and the boiling point of the reaction medium.

The deprotection reaction for the compounds for which Ra or Rb is a protecting group for the amine function is carried out by any deprotection method known to those skilled in the art and in particular those described by T. W. Greene, Protective Groups in Organic Synthesis, J. Wiley-Interscience Publication (1991). Preferably, when the protecting group is an acetyl radical, this reaction is carried out using aqueous hydrochloric acid, at a temperature of 100° C. When the protecting group is a tert-butoxycarbonyl radical, this reaction is carried out using hydrochloric acid in dioxane, at a temperature in the region of 20° C.

The compounds of formula (IV) may themselves be obtained according to the following reaction scheme:

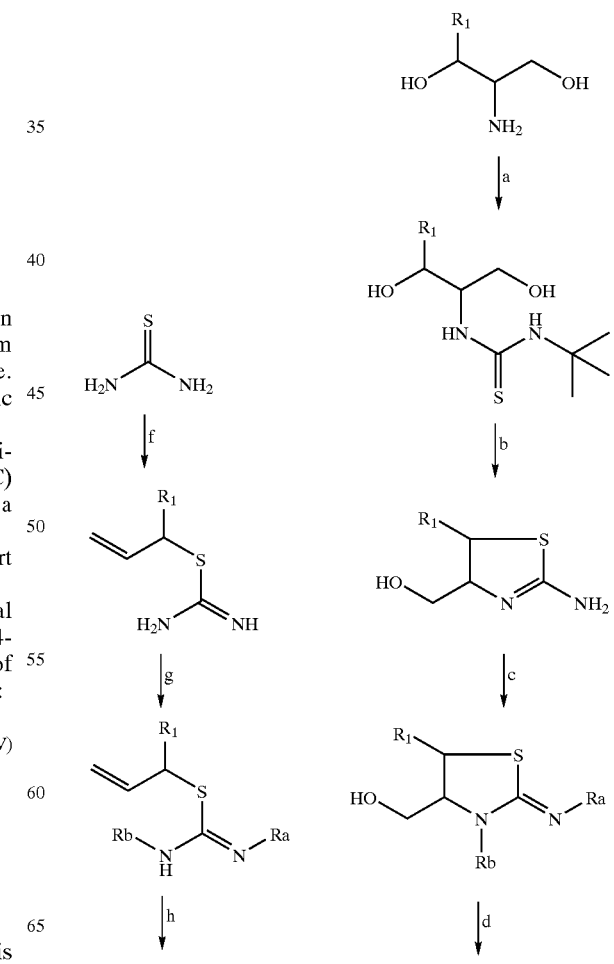

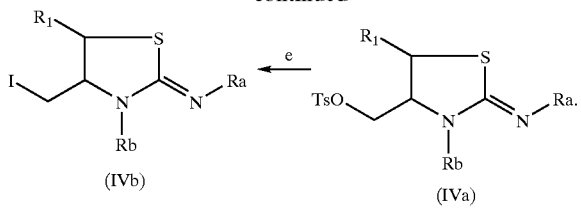

In these formulae, $R_1$ has the same meaning as in formula (I), Ts is a tosylate radical, Ra and Rb are a hydrogen atom or a protecting group for the amine function such as those described by T. W. Greene, Protective Groups in Organic Synthesis, J. Wiley-Interscience Publication (1991), preferably alkoxycarbonyl or acetyl and more particularly tert-butoxycarbonyl.

Reaction a is generally carried out by the action of tert-butyl isothiocyanate, in an inert solvent such as an aliphatic alcohol (1-4C) (preferably methanol or ethanol), optionally in the presence of a tertiary amine such as triethylamine, at a temperature of between 20° C. and the boiling point of the reaction medium.

Cyclization reaction b is generally carried out using an acid such as hydrochloric acid, in aqueous medium, at a temperature in the region of 100° C. 6N hydrochloric acid is preferably used.

When Ra or Rb is a tert-butoxycarbonyl group, reactions c and g are carried out by any protection method known to those skilled in the art and in particular those described by T. W. Greene, Protective Groups in Organic Synthesis, J. Wiley-Interscience Publication (1991). This reaction is preferably carried out using di-tert-butyl dicarbonate, in the presence of a base such as triethylamine and optionally in the presence of 4-(dimethylamino)pyridine, in a solvent such as dichloromethane and at a temperature in the region of 20° C., or alternatively in the presence of a base such as potassium carbonate, in a solvent such as water and at a temperature in the region of 20° C.

Reaction d is generally carried out by the action of p-toluenesulfonyl chloride, in the presence of a tertiary amine such as triethylamine, in an inert solvent such as dichloromethane, at a temperature of between 20° C. and the boiling point of the reaction medium.

Reaction e is generally carried out by the action of sodium iodide, in an inert solvent such as acetone, at a temperature of between 20° C. and the boiling point of the reaction medium.

Reaction f is generally carried out by the action of an allyl halide, for example allyl chloride, in an aliphatic alcohol (1-4C), preferably ethanol, at a temperature of between 20° C. and the boiling point of the reaction medium.

Reaction h is generally carried out by the action of iodine, in the presence of base such as sodium bicarbonate, in a solvent such as dichloromethane, at a temperature of between 20° C. and the boiling point of the reaction medium.

The compounds of formula (I) for which $R_2$ is a radical —$CH_2$—S—$R_4$ may be prepared by the action of a corresponding compound of formula (IVa) or (IVb) with a derivative of formula HS-$R_4$ in which $R_4$ has the same meaning as in formula (I) and Ra and Rb are hydrogen atoms or protecting groups for the amine function such as those described by T. W. Greene, Protective Groups in Organic Synthesis, J. Wiley-Interscience Publication (1991), preferably alkoxycarbonyl or acetyl and more particularly tert-butoxycarbonyl, optionally followed by a deprotection of the amine function.

This reaction is generally carried out in the presence of a base such as potassium carbonate, in a solvent such as acetonitrile or dimethylformamide (preferably acetonitrile), at a temperature of between 20° C. and the boiling point of the reaction medium.

The deprotection reaction for the compounds for which Ra or Rb is a protecting group for the amine function is carried out by any deprotection method known to those skilled in the art and in particular those described by T. W. Greene, Protective Groups in Organic Synthesis, J. Wiley-Interscience Publication (1991). Preferably, when the protecting group is an acetyl radical, this reaction is carried out using aqueous hydrochloric acid, at a temperature of 100° C. When the protecting group is a tert-butoxycarbonyl radical, this reaction is carried out using hydrochloric acid in dioxane, at a temperature in the region of 20° C. The compounds of formula (I) are isolated and may be purified by the usual known methods, for example by crystallization, chromatography or extraction.

The enantiomers of the compounds of formula (I) can be obtained by resolving the racemic mixtures, for example by chromatography on a chiral column according to Pirckle W. H. et al., Asymmetric Synthesis, Vol. 1, Academic Press (1983) or by formation of salts or by synthesis from chiral precursors. The diastereoisomers can be prepared according to the known conventional methods (crystallization or chromatography or from chiral precursors).

The compounds of formula (I) can optionally be converted into addition salts with an inorganic or organic acid by the action of such an acid in an organic solvent such as an alcohol, a ketone, an ether or a chlorinated solvent. These salts also form part of the invention.

Examples of pharmaceutically acceptable salts which may be mentioned are the following salts: benzenesulfonate, hydrobromide, hydrochloride, citrate, ethanesulfonate, fumarate, gluconate, iodate, isethionate, maleate, methanesulfonate, methylenebis-β-oxynaphthoate, nitrate, oxalate, pamoate, phosphate, salicylate, succinate, sulfate, tartrate, theophyllineacetate and p-toluenesulfonate.

The compounds of formula (I) are inhibitors of inducible NO-synthase or type-2 NO-synthase (NOS-2) and are thus useful for preventing and treating disorders associated with excessive NO production, such as multiple sclerosis, cerebral, focal or global ischemia, cerebral or spinal trauma, Parkinson's disease, Huntington's disease, Alzheimer's disease, amiotrophic lateral sclerosis, migraine, depression, schizophrenia, anxiety and epilepsy, diabetes, atherosclerosis, myocarditis, arthritis, arthrosis, asthma, irritable bowel syndrome, Crohn's disease, peritonitis, gastro-esophageal reflux, uveitis, Guillain-Barré syndrome, glomerulonephritis, lupus erythematosus, psoriasis, the growth of certain forms of tumors such as, for example, epitheliomas, adenocarcinomas or sarcomas, and infections with Gram-positive or Gram-negative intracellular or extracellular bacteria.

Their activities as NOS-2 and NOS-3 inhibitors were determined by measuring the conversion of [$^3$H]-L-arginine into [$^3$H]-L-citrulline with, respectively, an NOS-2 enzymatic fraction extracted from the lungs of rats or mice pretreated with lipopolysaccharides (10 mg/kg i.p. 6 hours before collecting the tissue) and with a commercial preparation of recombinant bovine NOS-3. The compounds were incubated for 20 to 30 minutes at 37° C. in the presence of 5 μM (for NOS-2 activity) or 10 μM (for NOS-3 activity) of [$^3$H]-L-arginine, 1 mM of NADPH, 15 μM of tetrabiopterine, 1 μM of FAD, 0.1 mM of DTT in a HEPES buffer (50 mM, pH 6.7) containing 10 μg/ml of calmodulin and 1.25 mM of $CaCl_2$ when the NOS-3 activity was measured. The incubation was stopped by adding cold HEPES buffer (100 mM, pH 5.5) containing 10 mM of EGTA and 500 mg of a cationic ion-exchange resin (AG50W-X8, counterion: $Na^+$) to separate the $[^3H]$-L-arginine from the $[^3H]$-L-citrulline. After separation of the phases by settling for 5 min, the radioactivity remaining in the liquid phase was measured in a scintillation counter in the presence of a suitable scintillation liquid. The yield for the recovery of the $[^3H]$-L-citrulline formed was able to be estimated using $[^{14}C$-ureido]-L-citrulline as external standard. The NOS-2 or NOS-3 activity was expressed in picomole(s) of $[^3H]$-L-citrulline formed per minute and per milligram of protein contained in the reaction medium.

In this test on the enzyme NOS-2, the $IC_{50}$ value for the compounds of formula (I) is less than or equal to 10 μM.

The selectivity is measured by the NOS-3 $IC_{50}$/NOS-2 $IC_{50}$ ratio. This selectivity is greater than 20.

The compounds of formula (I) are of low toxicity. Their $LD_{50}$ value is greater than 40 mg/kg via the cutaneous route in mice.

The examples which follow illustrate the invention.

EXAMPLE 1

(+)-(4R)-4-(3-Pyridylmethyl)-4,5-dihydro-1,3-thiazol-2-ylamine dihydrochloride

A suspension of 3.35 g of N-(tert-butyl)-N'-[(1R)-2-hydroxy-1-(3-pyridylmethyl)ethyl]thiourea in 32 $cm^3$ of 6N hydrochloric acid is heated at a temperature in the region of 100° C. for 5 hours and the heating is then stopped. The solution is then evaporated under reduced pressure (2 kPa) at a temperature in the region of 50° C. 4.42 g of a yellow oil which becomes pasty are obtained. This paste is taken up in acetone and then re-evaporated under reduced pressure (2 kPa) at a temperature in the region of 40° C. The residue is taken up in diethyl ether. Light beige-colored crystals are obtained, and are filtered off on a sinter funnel and then washed with diethyl ether and dried in an oven under reduced pressure (0.1 kPa) at a temperature in the region of 50° C. 3.28 g of (+)-(4R)-4-(3-pyridylmethyl)-4,5-dihydro-1,3-thiazol-2-ylamine dihydrochloride are obtained in the form of a light beige-colored sandy solid melting at 124° C. [$^1$H NMR spectrum (300 MHz, $(CD_3)_2SO-d_6$, δ in ppm): 3.20 (mt: 2H); 3.40 (dd, J=11 and 5 Hz: 1H); 3.70 (dd, J=11 and 8 Hz: 1H); 4.67 (mt: 1H); 7.97 (dd, J=8 and 5.5 Hz: 1H); 8.46 (broad d, J=8 Hz: 1H); 8.83 (broad d, J=5.5 Hz: 1H); 8.90 (d, J=2 Hz: 1H); 9.28 (unres. mult.: 1H); 9.75 (unres. mult.: 1H); 10.30 (unres. mult.: 1H); ($\alpha_D^{20}$=+18.3±0.7 at a concentration of 0.5% in methanol)].

N-(tert-Butyl)-N'-[(1R)-2-hydroxy-1-(3-pyridylmethyl)ethyl]thiourea: 22.7 $cm^3$ of triethylamine and then 14 $cm^3$ of tert-butyl isothiocyanate are added dropwise to a suspension, under an inert atmosphere, of 16.51 g of (2R)-2-amino-3-(3-pyridyl)-1-propanol dihydrochloride in 200 $cm^3$ of ethanol. The mixture is then heated at a temperature in the region of 60° C. for 1 hour 30 min. After cooling to a temperature in the region of 20° C., the insoluble material is filtered off on a sinter funnel and the filtrate is then evaporated under reduced pressure (2 kPa) at a temperature in the region of 40° C. A yellow paste is obtained, and is taken up in 200 $cm^3$ of ethyl acetate and 100 $cm^3$ of water. The aqueous phase is extracted and then washed with twice 200 $cm^3$ of ethyl acetate. The organic phases are combined, washed with 3 times 50 $cm^3$ of saturated sodium chloride solution and dried over magnesium sulfate. After filtration and then evaporation under reduced pressure (2 kPa) at a temperature in the region of 40° C., a yellow oil is obtained, which is taken up in dichloromethane and re-evaporated to give 3.25 g of N-(tert-butyl)-N'-[(1R)-2-hydroxy-1-(3-pyridylmethyl)-ethyl]thiourea in the form of a pale yellow foam: [$^1$H NMR spectrum (400 MHz, $(CD_3)_2SO-d_6$, δ in ppm): 1.41 (s: 9H); 2.84 (mt: 2H); 3.37 (mt: 2H); 4.43 (unres. mult.: 1H); 4.96 (t, J=5 Hz: 1H); 7.24 (d, J=8 Hz: 1H); 7.27 (broad s: 1H); 7.33 (dd, J=8 and 5 Hz: 1H); 7.67 (dt, J=8 and 2 Hz: 1H); 8.42 (dd, J=5 and 2 Hz: 1H); 8.46 (d, J=2 Hz: 1H)].

(2R)-2-Amino-3-(3-pyridyl)-1-propanol dihydrochloride: A suspension of 13.55 g of N-[(1R)-2-hydroxy-1-(3-pyridylmethyl)ethyl]acetamide in 110 $cm^3$ of aqueous 6N hydrochloric acid is heated at a temperature in the region of 100° C. for 3 hours. The water is evaporated off under reduced pressure (3 kPa) at a temperature in the region of 50° C. 16.51 g of (2R)-2-amino-3-(3-pyridyl)-1-propanol dihydrochloride are obtained in the form of an off-white solid. [$^1$H NMR spectrum (400 MHz, $(CD_3)_2SO-d_6$, δ in ppm): 3.13 (d, J=7.5 Hz: 2H); 3.50 (mt: 2H); 3.62 (mt: 1H); 7.94 (dd, J=8 and 5.5 Hz: 1H); 8.27 (unres. mult.: 3H); 8.43 (broad d, J=8 Hz: 1H); 8.79 (broad d, J=5.5 Hz: 1H); 8.86 (broad s: 1H)].

N-[(1R)-2-Hydroxy-1-(3-pyridylmethyl)ethyl]-acetamide: A solution, under an inert atmosphere, of 20.77 g of ethyl (2R)-2-(acetylamino)-3-(3-pyridyl)propanoate in 208 $cm^3$ of anhydrous ethanol is cooled to a temperature in the region of 10° C., followed by portionwise addition of 8.31 g of sodium borohydride. The reaction mixture is stirred for 16 hours at room temperature. The ethanol is evaporated off under reduced pressure (2 kPa) at a temperature in the region of 40° C., to give 43.56 g of a pale yellow paste which is taken up and stirred in 50 $cm^3$ of water. The solution, which has a pH in the region of 12, is cooled to a temperature in the region of 0° C. and then neutralized by dropwise addition of concentrated hydrochloric acid. The resulting mixture is stirred for 1 hour at this temperature and the white precipitate formed is then filtered off on a sinter funnel, then dried in an oven under vacuum (0.1 kPa) at a temperature in the region of 55° C. 11.15 g of N-[(1R)-2-hydroxy-1-(3-pyridylmethyl)ethyl]acetamide are obtained in the form of a white solid melting at a temperature above 260° C. The filtrate is extracted with 3 times 100 $cm^3$ of ethyl acetate and the organic phases are then combined, dried over magnesium sulfate, filtered and evaporated under reduced pressure (2 kPa) at a temperature in the region of 40° C. 2.4 g of N-[(1R)-2-hydroxyl-1-(3-pyridylmethyl)ethyl]acetamide partially complexed with boron are obtained in the form of a white paste. [$^1$H NMR spectrum (300 MHz, $(CD_3)_2SO-d_6$, δ in ppm): 1.75 (s: 3H); 2.61 (dd, J=14 and 9 Hz: 1H); 2.88 (dd, J=14 and 5.5 Hz: 1H); from 3.20 to 3.45 (mt: 2H); 3.91 (mt: 1H); 4.82 (broad t, J=5 Hz: 1H); 7.30 (dd, J=7.5 and 5 Hz: 1H); 7.62 (dt, J=7.5 and 2 Hz: 1H); 7.72 (d, J=9 Hz: 1H); from 8.35 to 8.45 (mt: 2H)].

Ethyl (2R)-2-(acetylamino)-3-(3-pyridyl)propanoate: A suspension of 54.7 g of ethyl 2-(acetylamino)-3-(3-pyridyl) propanoate in 420 $cm^3$ of water, to which has been added 18.5 g of potassium chloride, is dissolved by adding 100 $cm^3$ of acetonitrile. An orange-colored solution of neutral pH is obtained, 0.168 g of α-chymotrypsin is then added and the pH falls. Aqueous 2N potassium hydroxide solution is added dropwise, with stirring, to remain at a constant pH of 7.2. After 1 hour 30 min, with the pH showing little change, the mixture is stirred for 48 hours at room temperature. The pH of the solution is then approximately 5.6 and, on adding aqueous 2N potassium hydroxide solution, it is thereby adjusted to about 7. 0.084 g of α-chymotrypsin is introduced and the pH is adjusted to 7.2 by a further addition of aqueous 2N potassium hydroxide solution, and the mixture is left stirring for 1 hour 30 min. The pH of the reaction medium does not change. 400 cm³ of ethyl acetate are added and the mixture is stirred for 30 min and then filtered through Celite. The filtrate is separated out after settling has taken place and the aqueous phase is extracted with 3 times 400 cm³ of ethyl acetate. The organic phases are combined, washed with 400 cm³ of saturated sodium chloride solution and dried over magnesium sulfate. After filtration and concentration under reduced pressure (2 kPa) at a temperature in the region of 40° C., 20.77 g of ethyl (2R)-2-(acetylamino)-3-(3-pyridyl) propanoate are obtained in the form of a beige-colored solid melting at 80° C. [$^1$H NMR spectrum (400 MHz, (CD$_3$)$_2$SO-d$_6$, δ in ppm): 1.13 (t, J=7 Hz: 3H); 1.81 (s: 3H); 2.92 (dd, J=14 and 9.5 Hz: 1H); 3.05 (dd, J=14 and 5.5 Hz: 1H); 4.07 (q, J=7 Hz: 2H); 4.48 (mt: 1H); 7.33 (dd, J=8 and 5 Hz: 1H); 7.66 (dt, J=8 and 2 Hz: 1H); 8.36 (d, J=8 Hz: 1H); 8.44 (mt: 2H)].

Ethyl 2-(acetylamino)-3-(3-pyridyl)-propanoate: 44.45 cm³ of aqueous 6N sodium hydroxide are added dropwise to a solution of 51.4 g of diethyl 2-(acetylamino)-2-(3-pyridylmethyl)malonate in 857 cm³ of ethanol. The mixture is stirred for 1 hour 30 minutes at a temperature in the region of 20° C. and then cooled to a temperature in the region of 0° C. 22.2 cm³ of 12N hydrochloric acid are added dropwise; a precipitate forms. The reaction medium is warmed to room temperature and, after stirring for 2 hours, its pH is 5–6. It is concentrated under reduced pressure (4 kPa) at a temperature in the region of 50° C., to give a sticky dark-beige solid which is dried for 16 hours in an oven under vacuum (0.1 kPa) at a temperature in the region of 50° C. This residue is taken up in 1000 cm³ of dioxane and then heated to a temperature in the region of 100° C. for 1 hour. The dioxane is evaporated off under reduced pressure (2 kPa) at a temperature in the region of 40° C., and the residue is dissolved in 250 cm³ of water. This solution is neutralized by addition of 4 cm³ of aqueous 10N sodium hydroxide, followed by addition of 750 cm³ of ethyl acetate. After separation of the phases by settling, the organic phase is extracted and the aqueous phase is washed with twice 300 cm³ of ethyl acetate. The organic phases are combined, dried over magnesium sulfate, filtered and concentrated under reduced pressure (2 kPa) at a temperature in the region of 40° C. The solid residue obtained is taken up in 70 cm³ of ethyl acetate and 20 cm³ of heptane and then filtered on a sinter funnel. 27.76 g of ethyl 2-(acetylamino)-3-(3-pyridyl) propanoate are obtained in the form of a beige-colored solid melting at 118° C. [$^1$H NMR spectrum (400 MHz, (CD$_3$)$_2$SO-d$_6$, δ in ppm): 1.13 (t, J=7 Hz: 3H); 1.81 (s: 3H); 2.92 (dd, J=14 and 9 Hz: 1H); 3.04 (dd, J=14 and 5.5 Hz: 1H); 4.07 (q, J=7 Hz: 2H); 4.48 (mt: 1H); 7.33 (dd, J=8 and 5 Hz: 1H); 7.66 (dt, J=8 and 2 Hz: 1H); 8.38 (d, J=8 Hz: 1H); 8.45 (mt: 2H)]. By re-extracting the aqueous phase with twice 500 cm³ of ethyl acetate and after drying and concentration of the combined organic phases under reduced pressure, 4 g of ethyl 2-(acetylamino)-3-(3-pyridyl)propanoate are recovered in the form of a beige-yellow solid melting at 121° C.

In the same way, starting with 50.2 g of diethyl 2-(acetylamino)-2-(3-pyridylmethyl)malonate, 26.94 g of ethyl 2-(acetylamino)-3-(3-pyridyl)-propanoate are obtained.

Diethyl 2-(acetylamino)-2-(3-pyridylmethyl)-malonate: 17.2 g of sodium prewashed twice with pentane are added portionwise, with stirring under an inert atmosphere, to 600 cm³ of ethanol. After total consumption of the sodium, 73.5 g of diethyl acetamidomalonate are added rapidly and the mixture is left stirring for 30 min at a temperature in the region of 40° C. A suspension of 56 g of 3-picolyl chloride hydrochloride in 300 cm³ of ethanol is then added rapidly and the resulting pinkish suspension is stirred for 44 hours at a temperature in the region of 20° C. 28.1 g of potassium iodide are added and stirring is continued at room temperature for 4 hours, and the reaction mixture is finally heated at a temperature in the region of 50° C. for 44 hours. The mixture is cooled to a temperature in the region of 0° C. and then filtered through a sinter funnel to remove the salts, which are washed with ethanol. The filtrate is concentrated under reduced pressure (2 kPa) at a temperature in the region of 40° C. A brown-colored paste is obtained, and is dissolved in 100 cm³ of water and treated with 7 cm³ of aqueous 3N hydrochloric acid until a pH in the region of 6 is obtained. The mixture is placed in a refrigerator for 48 hours. The crystalline precipitate obtained is filtered off on a sinter funnel, washed with 50 cm³ of ice-cold water, spin-filtered and then dried in a desiccator under reduced pressure (5 kPa) for 16 hours. After drying in an oven under reduced pressure (0.1 kPa) at a temperature in the region of 40° C. for 4 hours, 50.2 g of diethyl 2-(acetylamino)-2-(3-pyridylmethyl) malonate are obtained in the form of a dark beige-colored solid melting at 96° C. [$^1$H NMR spectrum (400 MHz, (CD$_3$)$_2$SO-d$_6$, δ in ppm) 1.19 (t, J=7 Hz: 6H); 1.97 (s: 3H); 3.47 (s: 2H); 4.17 (q, J=7 Hz: 4H); 7.33 (dd, J=8 and 5 Hz: 1H); 7.41 (dt, J=8 and 2 Hz: 1H); 8.21 (d, J=2 Hz: 1H); 8.24 (s: 1H); 8.24 (s: 1H); 8.47 (dd, J=5 and 2 Hz: 1H)].

EXAMPLE 2

(+)-(4R)-4-(3-Nitrobenzyl)-4,5-dihydro-1,3-thiazol-2-ylamine hydrochloride 1.1 g of N-(tert-butyl)-N'-[(1R)-2-hydroxy-1-(3-nitrobenzyl)ethyl]thiourea in 12 cm³ of 6N hydrochloric acid are heated for 5 hours at a temperature in the region of 100° C. The reaction medium is then cooled to a temperature in the region of 0° C.; a white precipitate forms, which is filtered off on a sinter funnel and then washed with 3 times 20 cm³ of diethyl ether. The filter cake is then dried in a desiccator under vacuum. 0.68 g of (+)-(4R)-4-(3-nitrobenzyl)-4,5-dihydro-1,3-thiazol-2-ylamine hydrochloride is obtained in the form of beige-colored crystals melting at 232° C. [$^1$H NMR spectrum (300 MHz, (CD$_3$)$_2$SO-d$_6$, δ in ppm): 3.15 (limiting AB: 2H); from 3.25 to 3.45 (mt: 1H); 3.63 (dd, J=13 and 8 Hz: 1H); 4.62 (mt: 1H); 7.68 (t, J=8 Hz: 1H); 7.81 (broad d, J=8 Hz: 1H); 8.18 (broad d, J=8 Hz: 1H); 8.24 (broad s: 1H); from 9.00 to 10.40 (unres. mult.: 3H); ($\alpha_D^{20}$=+18.8±0.6 at a concentration of 0.5% in methanol)].

N-(tert-Butyl)-N'-[(1R)-2-hydroxy-1-(3-nitrobenzyl) ethyl]thiourea: A suspension of 0.92 g of (2R)-2-amino-3-(3-nitrophenyl)-1-propanol hydrochloride and 0.6 cm³ of tert-butyl isothiocyanate in 10 cm³ of ethanol is cooled to a temperature in the region of 0° C. and 0.56 cm³ of triethylamine is then added. The mixture is stirred for 18 hours at room temperature and is then heated at a temperature in the region of 60° C. for 2 hours; the suspension thus dissolves. 0.6 cm³ of tert-butyl isothiocyanate is added and heating is continued for 3 hours, after which the reaction medium is concentrated under reduced pressure (2 kPa) at a temperature in the region of 50° C. The yellow oil obtained is dissolved in 50 cm³ of ethyl acetate, after which the organic solution is washed with twice 50 cm³ of sodium chloride solution, dried over sodium sulfate, filtered and concentrated under reduced pressure (2 kPa) at a temperature in the region of 40° C. 1.2 g of N-(tert-butyl)-N'-[(1R)-2-hydroxy-1-(3-nitrobenzyl)-ethyl]thiourea are obtained in the form of a yellow oil. $^1$H NMR spectrum (300 MHz, (CD$_3$)$_2$SO-d$_6$ with addition of a few drops of CD$_3$COOD-d$_4$, δ in ppm): 1.39 (s: 9H); 2.98 (limiting AB: 2H); 3.38 (limiting AB: 2H); 4.48 (mt: 1H); 7.60 (t, J=8 Hz: 1H); 7.74 (broad d, J=8 Hz: 1H); 8.09 (broad d, J=8 Hz: 1H); 8.16 (broad s: 1H).

(2R)-2-Amino-3-(3-nitrophenyl)-1-propanol hydrochloride: A suspension of 0.98 g of N-[(1R)-2-hydroxy-1-(3-nitrobenzyl)ethyl]acetamide in 10 cm$^3$ of 6N hydrochloric acid is heated at a temperature in the region of 100° C. for 10 hours (dissolution). The reaction medium is concentrated under reduced pressure (2 kPa) at a temperature in the region of 40° C. The residue is taken up in 20 cm$^3$ of diethyl ether and re-evaporated under the same conditions to give beige-colored crystals, which are washed with 3 times 20 cm$^3$ of diethyl ether and then filtered off on a sinter funnel and finally dried in a fume cupboard. 0.92 g of (2R)-2-amino-3-(3-nitrophenyl)-1-propanol hydrochloride is obtained in the form of beige-colored crystals melting at 192° C. [$^1$H NMR spectrum (250 MHz, (CD$_3$)$_2$SO-d$_6$, δ in ppm): 3.06 (limiting AB: 2H); from 3.25 to 3.65 (mt: 3H); 5.45 (t, J=4.5 Hz: 1H); 7.65 (t, J=7 Hz: 1H); 7.79 (broad d, J=7 Hz: 1H); from 8.05 to 8.40 (mt: 5H)].

N-[(1R)-2-Hydroxy-1-(3-nitrobenzyl)ethyl]-acetamide: A light suspension, under an inert atmosphere, of 1.4 g of ethyl (2R)-2-(acetylamino)-3-(3-nitrophenyl)propanoate in 13 cm$^3$ of ethanol is cooled to a temperature of 20° C. and 0.29 g of sodium borohydride is then added thereto. The yellow solution obtained is stirred at room temperature for 18 hours. The reaction medium is then concentrated under reduced pressure (2 kPa) at a temperature in the region of 50° C., after which 10 cm$^3$ of water are added and the mixture is extracted with twice 50 cm$^3$ of ethyl acetate. The combined organic phases are dried over sodium sulfate, filtered and then concentrated under reduced pressure (2 kPa) at a temperature in the region of 40° C. 1 g of N-[(1R)-2-hydroxy-1-(3-nitrobenzyl)ethyl]-acetamide is obtained in the form of pale yellow crystals melting at 135° C. $^1$H NMR spectrum (250 MHz, (CD$_3$)$_2$SO-d$_6$, δ in ppm): 1.75 (s: 3H); 2.74 (dd, J=14 and 9 Hz: 1H); 3.02 (dd, J=14 and 5 Hz: 1H); from 3.25 to 3.45 (mt: 2H); 3.96 (mt: 1H); 4.90 (broad s: 1H); 7.59 (t, J=8 Hz: 1H); 7.70 (broad d, J=8 Hz: 1H); 7.82 (d, J=8.5 Hz: 1H); from 8.05 to 8.15 (mt: 2H).

Ethyl (2R)-2-(acetylamino)-3-(3-nitrophenyl)-propanoate: A mixture of 2.8 g of ethyl 2-(acetylamino)-3-(3-nitrophenyl)propanoate in 17 cm$^3$ of acetonitrile [lacuna] to which is added 3.95 g of ammonium hydrogen carbonate and 35 cm$^3$ of water at a pH in the region of 8. 0.017 g of type-II α-chymotrypsin is then introduced and the mixture is left stirring at room temperature for 1 hour 15 min, while measuring the pH regularly. After this reaction time, the pH is less than 8, a further 0.017 g of type-II α-chymotrypsin is added and stirring of the reaction medium is continued for 2 hours 45 min. The aqueous phase is extracted with 3 times 50 cm$^3$ of ethyl acetate; the combined organic phases are then dried over sodium sulfate, filtered and evaporated under reduced pressure (2 kPa) at a temperature in the region of 40° C. 1.4 g of ethyl (2R)-2-(acetylamino)-3-(3-nitrophenyl) propanoate are obtained in the form of white crystals melting at 110° C.

Ethyl 2-(acetylamino)-3-(3-nitrophenyl)-propanoate: 9.52 cm$^3$ of acetic anhydride are added dropwise to 12 g of ethyl 2-amino-3-(3-nitrophenyl)propanoate at a temperature in the region of 0° C. After stirring at 0° C. for 1 hour, the mixture sets to a solid. 10 cm$^3$ of acetic anhydride are then added and stirring is continued at 0° C. for a further 1 hour. The precipitate is filtered off on a sinter funnel, washed with 3 times 25 cm$^3$ of water and dried in a fume cupboard and then in an oven under vacuum (10 Pa) at a temperature in the region of 50° C. 12 g of ethyl 2-(acetylamino)-3-(3-nitrophenyl)propanoate are obtained in the form of white crystals melting at 91° C. $^1$H NMR spectrum (250 MHz, (CD$_3$)$_2$SO-d$_6$, δ in ppm): 1.14 (t, J=7 Hz: 3H); 1.80 (s: 3H); 3.04 (dd, J=14 and 9 Hz: 1H); 3.18 (t, J=14 and 4 Hz: 1H); 4.08 (q, J=7 Hz: 2H); 4.52 (mt: 1H); 7.61 (broad t, J=8 Hz: 1H); 7.72 (broad d, J=8 Hz: 1H); 8.12 (mt: 2H); 8.42 (d, J=8.5 Hz: 1H).

Ethyl 2-amino-3-(3-nitrophenyl)propanoate: Gaseous hydrogen chloride is bubbled, to the saturation point, into a mixture of 23.4 g of 3-nitrophenylalanine hydrochloride in 300 cm$^3$ of ethanol cooled to a temperature in the region of 0° C. The suspension obtained is heated at a temperature in the region of 78° C. for 18 hours: this suspension dissolves when hot. The heating is stopped and gaseous hydrogen chloride is bubbled into the solution for 15 min, with re-heating at a temperature in the region of 78° C. for 70 hours. The reaction medium is concentrated under reduced pressure (2 kPa) at a temperature in the region of 50° C. and the residue is then basified to a pH of about 10 with sodium carbonate solution. This aqueous phase is extracted with 3 times 100 cm$^3$ of dichloromethane and the combined organic phases are then dried over sodium sulfate, filtered and evaporated under reduced pressure (2 kPa) at a temperature in the region of 40° C. to give 12.2 g of ethyl 2-amino-3-(3-nitrophenyl)propanoate in the form of an orange-colored oil. 1H NMR spectrum (250 MHz, (CD$_3$)$_2$SO-d$_6$, δ in ppm): 1.14 (t, J=7 Hz: 3H); 1.88 (unres. mult.: 2H); 2.92 (dd, J=13 and 7 Hz: 1H); 3.02 (dd, J=13 and 6 Hz: 1H); 3.62 (dd, J=7 and 6 Hz: 1H); 4.05 (q, J=7 Hz: 2H); 7.59 (resolved t, J=8.5 and 1.5 Hz: 1H); 7.71 (broad d, J=8 Hz: 1H); from 8.05 to 8.20 (mt: 2H).

3-Nitrophenylalanine hydrochloride: A suspension of 34 g of diethyl 2-(acetylamino)-2-(3-nitrobenzyl)malonate in 510 cm$^3$ of concentrated hydrochloric acid is heated at a temperature in the region of 100° C. for 18 hours: a vigorous evolution of gas takes place and the suspension dissolves when hot. The reaction mixture is then cooled to a temperature in the region of 0° C., after which it is stirred for 1 hour at 0° C. and finally filtered through a sinter funnel. The filter cake is washed with twice 50 cm$^3$ of filtrate and dried in a fume cupboard and then in an oven under vacuum (10 Pa) at a temperature in the region of 60° C. 23.4 g of 3-nitrophenylalanine hydrochloride are obtained in the form of white crystals melting at 222° C.

Diethyl 2-(acetylamino)-2-(3-nitrobenzyl)-malonate: 3.1 g of sodium are added, while stirring under an inert atmosphere, to 300 cm$^3$ of ethanol. After total consumption of the sodium, 29.1 g of diethyl acetamidomalonate are added and the mixture is then heated at a temperature in the region of 78° C. for 20 minutes. A solution of 23 g of 3-nitrobenzyl chloride in 100 cm$^3$ of ethanol is then added and heating is continued at this same temperature for 18 hours. The reaction mixture is cooled to a temperature in the region of 0° C. After stirring under these cold conditions for 1 hour, the precipitate formed is filtered off on a sinter funnel and the filter cake is washed with twice 50 cm$^3$ of filtrate and then twice 50 cm$^3$ of water. After drying under a fume cupboard and then in an oven under vacuum (10 Pa) at a temperature in the region of 50° C., 34 g of diethyl 2-(acetylamino)-2-(3-nitrobenzyl)malonate are obtained in the form of white crystals melting at 156° C.

EXAMPLE 3

(+)-(4R,5S)-4-Benzyl-5-methyl-4,5-dihydro-1,3-thiazol-2-ylamine

A suspension of 1.8 g of N-[(1R,2S)-1-benzyl-2-hydroxypropyl]-N'-tert-butylthiourea (diastereoisomer A) in 21 cm³ of 6N hydrochloric acid is heated at a temperature in the region of 100° C. for 6 hours. A further 10 cm³ of 6N hydrochloric acid are added and heating is continued for 6 hours. The reaction medium is filtered while hot through a sinter funnel and the insoluble material is washed with twice 5 cm³ of hot 6N hydrochloric acid. The filtrate is cooled to a temperature in the region of 0° C., after which 20 cm³ of water are added and this mixture is finally basified with 30 cm³ of 30% sodium hydroxide. The resulting mixture is extracted with 3 times 50 cm³ of dichloromethane. The combined organic phases are dried over sodium sulfate, filtered and concentrated under reduced pressure (2 kPa) at a temperature in the region of 40° C. 1 g of a pink oil is obtained, and is purified by chromatography under a pressure of argon (50 kPa) on a column of silica gel (particle size 40–63 μm; diameter 3 cm; height 35 cm), eluting with a mixture of 90% dichloromethane/10% methanol. The fractions containing the expected product are combined and concentrated under reduced pressure (2 kPa) at a temperature in the region of 40° C. 0.31 g of (+)-(4R,5S)-4-benzyl-5-methyl-4,5-dihydro-1,3-thiazol-2-ylamine is obtained in the form of white crystals melting at 90° C. [$^1$H NMR spectrum (300 MHz, $(CD_3)_2SO$-$d_6$ with addition of a few drops of $CD_3COOD$-$d_4$, δ in ppm): 1.31 (d, J=7 Hz: 3H); 2.89 (dd, J=14 and 7.5 Hz: 1H); 3.01 (dd, J=14 and 7.5 Hz: 1H); 3.91 (mt: 1H); 4.41 (mt: 1H); from 7.15 to 7.40 (mt: 5H). The relative stereochemistry at positions 4 and 5 was validated by NOE. A strong response of the methylene of the benzyl is noted after irradiating the methyl: ($α_D^{20}$=+29.6±0.8 at a concentration of 0.5% in methanol)].

N-[(1R,2S)-1-benzyl-2-hydroxypropyl]-N'-tert-butylthiourea: A solution of 12.9 g of a 75%/25% mixture of the 2 diastereoisomers of (3R)-3-amino-4-phenyl-2-butanol in 160 cm³ of ethanol, to which 9.50 cm³ of tert-butyl isothiocyanate have been added, is stirred at room temperature for 36 hours and then heated for 2 hours at a temperature in the region of 60° C. The reaction medium is concentrated under reduced pressure (2 kPa) at a temperature in the region of 40° C. to give 20.8 g of a yellow oil. This oil is purified by chromatography under a pressure of argon (50 kPa) on a column of silica gel (particle size 40–63 μm; diameter 5 cm; height 50 cm), eluting with a mixture of 95% dichloromethane/5% ethyl acetate. The fractions containing diastereoisomer A are evaporated under reduced pressure (2 kPa) at a temperature in the region of 40° C. 1.95 g of N-[(1R,2S)-1-benzyl-2-hydroxypropyl]-N'-tert-butylthiourea are obtained in the form of pale yellow crystals melting at 128° C. $^1$H NMR spectrum (250 MHz, $(CD_3)_2SO$-$d_6$, δ in ppm): 0.96 (d, J=7 Hz: 3H); 1.42 (s: 9H); 2.78 (limiting AB: 2H); 3.64 (mt: 1H); 4.33 (mt: 1H); 5.02 (d, J=4 Hz: 1H); from 7.10 to 7.40 (mt, 6H); 7.44 (broad s, 1H). By concentrating the fractions corresponding to diastereoisomer B under the same conditions, 6.5 g of N-[(1R,2R)-1-benzyl-2-hydroxypropyl]-N'-tert-butylthiourea are obtained in the form of white crystals melting at 155° C. $^1$H NMR spectrum (250 MHz, $(CD_3)_2SO$-$d_6$, δ in ppm): 1.08 (d, J=7 Hz: 3H); 1.39 (s: 9H); 2.80 (limiting AB: 2H); 3.68 (mt: 1H); 4.42 (unres. mult.: 1H); 4.78 (unres. mult.: 1H); 7.08 (d, J=8.5 Hz: 1H); from 7.10 to 7.40 (mt: 6H).

(3R)-3-Amino-4-phenyl-2-butanol: A solution of 19.3 g of tert-butyl (1R)-1-benzyl-2-hydroxypropylcarbamate in 160 cm³ of dioxane and 67 cm³ of 6.5N hydrochloric dioxane is stirred at room temperature for 5 hours and is then concentrated under reduced pressure (2 kPa) at a temperature in the region of 40° C. A yellow oil is obtained, and is taken up in 50 cm³ of water and basified to a pH in the region of 10 with potassium carbonate. This mixture is extracted with 3 times 100 cm³ of ethyl acetate and the combined organic phases are then dried over sodium sulfate, filtered and evaporated under reduced pressure (2 kPa) at a temperature in the region of 40° C. 12.9 g of a 75%/25% mixture of the two diastereoisomers A and B of (3R)-3-amino-4-phenyl-2-butanol are obtained in the form of an orange-colored oil. $^1$H NMR spectrum (300 MHz, $(CD_3)_2SO$-$d_6$, δ in ppm). A mixture of diastereoisomers is observed: from 0.70 to 1.50 (broad unres. mult.: 2H); 1.08 (d, J=6 Hz: 3H); from 2.25 to 2.45 (mt: 1H); from 2.70 to 2.85 (mt: 2H); 3.44 (mt: 1H); from 4.25 to 4.75 (unres. mult.: 1H); from 7.10 to 7.35 (mt: 5H).

tert-Butyl (1R)-1-benzyl-2-hydroxypropylcarbamate: A solution of 21 g of tert-butyl (1R)-1-benzyl-2-oxopropylcarbamate in 200 cm³ of ethanol under an inert atmosphere is cooled to a temperature in the region of 10° C., followed by portionwise addition of 4.55 g of sodium borohydride. The temperature of the reaction medium is allowed to rise to room temperature with stirring, and the stirring is then continued for 18 hours. The reaction medium is concentrated under reduced pressure (2 kPa) at a temperature in the region of 40° C., to give white crystals which are taken up in 150 cm³ of water. This mixture is stirred for 2 hours at room temperature and then filtered through a sinter funnel. The filter cake is washed with twice 150 cm³ of water. After drying overnight in a fume cupboard, 19.37 g of tert-butyl (1R)-1-benzyl-2-hydroxypropylcarbamate are obtained in the form of white crystals melting at 127° C. $^1$H NMR spectrum (300 MHz, $(CD_3)_2SO$-$d_6$ with addition of a few drops of $CD_3COOD$-$d_4$, δ in ppm). A mixture of two diastereoisomers in 70/30 proportions is observed: 1.04 and 1.10 (2d, J=6 Hz: 3H); 1.29 and 1.32 (2s: 9H); from 2.40 to 3.10 (mt: 2H); from 3.35 to 3.70 (mt: 2H); 6.40 and 6.54 (2d, J=9 Hz: 1H); from 7.10 to 7.35 (mt: 5H).

tert-Butyl (1R)-1-benzyl-2-oxopropylcarbamate: A mixture of 26.7 9 of tert-butyl (1R)-1-benzyl-2-[methoxy(methyl)amino]-2-oxoethylcarbamate in 534 cm³ of tetrahydrofuran dried over 4 Å sieves is cooled, under an inert atmosphere, to a temperature in the region of 0° C. 87 cm³ of a 3 M solution of methylmagnesium bromide in diethyl ether are then added over 45 minutes and the resulting mixture is then stirred for 1 hour at 0° C. and for 18 hours at room temperature. The reaction medium is re-cooled to a temperature in the region of 0° C., 55 cm³ of 1N hydrochloric acid are then added dropwise and the mixture is stirred for 30 minutes at this temperature. After filtration through Celite, 200 cm³ of water are added to the filtrate, which is then extracted with twice 200 cm³ of ethyl acetate. The combined organic phases are dried over sodium sulfate, filtered and then concentrated under reduced pressure (2 kPa) at a temperature in the region of 40° C. 21.2 g of tert-butyl (1R)-1-benzyl-2-oxopropylcarbamate are obtained in the form of yellow crystals melting at 59° C. $^1$H NMR spectrum (300 MHz, $(CD_3)_2SO$-$d_6$, δ in ppm): 1.34 (s: 9H); 2.13 (s: 3H); 2.71 (dd, J=14 and 10 Hz: 1H); 3.01 (dd, J=14 and 5 Hz: 1H); 4.13 (mt: 1H); from 7.10 to 7.35 (mt: 6H).

tert-Butyl (1R)-1-benzyl-2-[methoxy(methyl)-amino]-2-oxoethylcarbamate: A solution of 26.5 g of D-N-Boc-phenylalanine and 22 cm³ of N-methylmorpholine in 300 cm³ of dichloromethane is cooled, under an inert atmosphere, to a temperature in the region of −15° C. 13 cm³ of isobutyl chloroformate are then added and the mixture is stirred for 15 min at this temperature. After addition of 10.14 g of N,O-dimethylhydroxylamine hydrochloride, stirring is continued for 1 hour at a temperature in the region of −15° C. and then for 3 hours at room temperature. 300 cm³ of water are added to the reaction medium, followed by extraction with twice 200 cm³ of dichloromethane. The combined organic phases are dried over sodium sulfate, filtered and concentrated under reduced pressure (2 kPa) at a temperature in the region of 50° C. 32.2 g of an orange-colored oil are obtained, and are purified on a column of silica gel (particle size 40–63 μm; height 32 cm), eluting with a mixture of 97% dichloromethane/3% methanol. After concentration of the fractions containing the expected product under reduced pressure (2 kPa) at a temperature in the region of 40° C., 26.7 g of tert-butyl (1R)-1-benzyl-2-[methoxy (methyl)amino]-2-oxoethylcarbamate are obtained in the form of a yellow oil. $^1$H NMR spectrum (250 MHz, (CD$_3$)$_2$SO-d$_6$, δ in ppm): 1.32 (s: 9H); 2.72 (dd, J=13.5 and 10 Hz: 1H); 2.86 (dd, J=13.5 and 5 Hz: 1H); 3.12 (s: 3H); 3.74 (broad s: 3H); 4.55 (mt: 1H); from 7.10 to 7.35 (mt: 6H).

EXAMPLE 4

(+)-(4R,5R)-4-Benzyl-5-methyl-4,5-dihydro-1,3-thiazol-2-ylamine

A suspension of 6.5 g of N-[(1R,2R)-1-benzyl-2-hydroxypropyl]-N'-tert-butylthiourea (diastereoisomer B) in 77 cm³ of 6N hydrochloric acid is heated at a temperature in the region of 100° C. for 10 hours. The reaction medium is then concentrated under reduced pressure (2 kPa) at a temperature in the region of 40° C. to give a yellow oil which is taken up in 100 cm³ of water. This aqueous phase is washed with twice 50 cm³ of dichloromethane and is then basified to a pH in the region of 10 by addition of 5 cm³ of concentrated sodium hydroxide. The resulting mixture is then extracted with 3 times 50 cm³ of dichloromethane. The combined organic phases are dried over sodium sulfate, filtered and then concentrated under reduced pressure (2 kPa) at a temperature in the region of 40° C. 4.09 g of (+)-(4R,5R)-4-benzyl-5-methyl-4,5-dihydro-1,3-thiazol-2-ylamine are obtained in the form of white crystals melting at 89° C. [$^1$H NMR spectrum (300 MHz, (CD$_3$)$_2$SO-d$_6$, δ in ppm): 1.22 (d, J=7 Hz: 3H); 2.66 (dd, J=13 and 7 Hz: 1H); 2.76 (dd, J=13 and 7 Hz: 1H); 3.54 (mt: 1H); 3.95 (mt: 1H); from 5.60 to 6.45 (unres. mult.: 2H); from 7.10 to 7,40 (mt: 5H). The relative stereochemistry in positions 4 and 5 was validated by NOE. A strong response of the proton H4 is noted after irradiating the methyl; ($\alpha_D^{20}$=+83.9±1.3 at a concentration of 0.5% in methanol)].

EXAMPLE 5

(−)-(4R)-4-(3-Thienylmethyl)-4,5-dihydro-1,3-thiazol-2-ylamine hydrochloride

A mixture of 0.94 g of N-(tert-butyl)-N'-[(1R)-2-hydroxy-1-(3-thienylmethyl)ethyl]thiourea in 9.2 cm³ of 6N hydrochloric acid is heated at a temperature in the region of 100° C. with stirring for 3 hours and is then concentrated under reduced pressure (2 kPa) at a temperature in the region of 40° C. A greenish oil is obtained, which is taken up in 10 cm³ of acetone to give a sticky gum. 1.5 cm³ of ethanol are then added, followed by dropwise addition, with stirring, of 6 cm³ of diethyl ether. The crystals obtained are filtered off on a sinter funnel, washed with diethyl ether and then dried in an oven under vacuum (10 Pa) at a temperature in the region of 50° C. 0.5 g of (−)-(4R)-4-(3-thienylmethyl)-4,5-dihydro-1,3-thiazol-2-ylamine hydrochloride is obtained in the form of gray crystals melting at 152° C. $^1$H NMR spectrum (400 MHz, (CD$_3$)$_2$SO-d$_6$, δ in ppm): 2.99 (mt: 2H); 3.26 (dd, J=11 and 5.5 Hz: 1H); 3.59 (dd, J=11 and 8 Hz: 1H); 4.54 (mt: 1H); 7.10 (dd, J=5.5 and 1 Hz: 1H); 7.38 (mt: 1H); 7.54 (dd, J=5 and 3 Hz: 1H); from 9.15 to 10.55 (broad unres. mult.: 3H). ($\alpha_D^{20}$=−4.3±0.5 at a concentration of 0.5% in methanol).

N-(tert-butyl)-N'-[(1R)-2-hydroxy-1-(3-thienylmethyl) ethyl]thiourea: 0.9 cm³ of tert-butyl isothiocyanate and then 0.82 cm³ of triethylamine are added to a suspension of 0.9 g of (2R)-2-amino-3-(3-thienyl)-1-propanol hydrochloride in 9 cm³ of absolute ethanol stirred and under an inert atmosphere. After stirring for 66 hours at room temperature, the reaction medium is evaporated under reduced pressure (2 kPa) at a temperature in the region of 40° C. The thick brown oil obtained is taken up in 6 cm³ of water and then extracted with twice 12 cm³ of ethyl acetate. The organic phase is filtered through Celite and washed with twice 4 cm³ of saturated aqueous sodium chloride solution, dried over magnesium sulfate and evaporated under reduced pressure (2 kPa) at a temperature in the region of 40° C. A brown oil is obtained, which crystallizes rapidly under cold conditions and which is dried in an oven under vacuum (10 Pa) at a temperature in the region of 48° C. to give 0.97 g of N-(tert-butyl)-N'-[(1R)-2-hydroxy-1-(3-thienylmethyl) ethyl]thiourea in the form of a beige-colored solid melting at 109° C. $^1$H NMR spectrum (400 MHz, (CD$_3$)$_2$SO-d$_6$, δ in ppm): 1.43 (s: 9H); 2.84 (mt: 2H); 3.38 (mt: 2H); 4.42 (unres. mult.: 1H); 4.86 (broad t, J=4.5 Hz: 1H); 7.04 (broad d, J=5 Hz: 1H); from 7.10 to 7.20 (mt: 2H); 7.25 (broad s: 1H); 7.46 (dd, J=5 and 3 Hz: 1H).

(2R)-2-Amino-3-(3-thienyl)-1-propanol hydrochloride: A solution of 1.4 g of N-[(1R)-2-hydroxy-1-(3-thienylmethyl) ethyl]acetamide in 17.6 cm³ of aqueous 6N hydrochloric acid is heated with stirring at a temperature in the region of 100° C. for 2 hours. The reaction mixture is then concentrated under reduced pressure (2 kPa) at a temperature in the region of 40° C. to give a greenish oil, which crystallizes from 60 cm³ of acetone. The crystals are filtered off on a sinter funnel, washed with acetone and then dried in an oven under vacuum (10 Pa) at a temperature in the region of 50° C. 0.92 g of (2R)-2-amino-3-(3-thienyl)-1-propanol hydrochloride is obtained in the form of an off-white solid. $^1$H NMR spectrum (400 MHz, (CD$_3$)$_2$SO-d$_6$, δ in ppm): 2.93 (mt: 2H); from 3.25 to 3.50 (mt: 2H); 3.53 (broad d, J=11 Hz: 1H); 5.37 (unres. mult.: 1H); 7.07 (broad d, J=5 Hz: 1H); 7.35 (mt: 1H); 7.53 (dd, J=5 and 3 Hz: 1H); 8.18 (unres. mult.: 3H)

N-[(1R)-2-Hydroxy-1-(3-thienylmethyl)-ethyl] acetamide: A solution of 2.15 g of ethyl (2R)-2-(acetylamino)-3-(3-thienyl)propanoate in 24 cm³ of ethanol, stirred under an inert atmosphere, is brought to a temperature of 20° C. 0.5 g of sodium borohydride is added and the reaction medium, which is slightly brown, is stirred for 24 hours at room temperature. A further 0.2 g of sodium borohydride is added and stirring is continued for 24 hours. After evaporation of the reaction mixture under reduced pressure (2 kPa) at a temperature in the region of 40° C., a solid residue is obtained, which is taken up in 30 cm³ of water. This mixture is extracted with twice 100 cm³ of ethyl acetate and the organic phase is then dried over magnesium sulfate and evaporated under reduced pressure (2 kPa) at a temperature in the region of 40° C. to give an off-white solid which is dried in an oven under vacuum (10 Pa) at a temperature in the region of 48° C. 1.4 g of N-[(1R)-2-hydroxy-1-(3-thienylmethyl)ethyl]acetamide are obtained in the form of an off-white solid melting at about 105° C. to become pasty. $^1$H NMR spectrum (400 MHz, (CD$_3$)$_2$SO-d$_6$, δ in ppm): 1.78 (s: 3H); 2.64 (dd, J=14 and 8 Hz: 1H); 2.87 (dd, J=14 and 5.5 Hz: 1H); from 3.20 to 3.40 (mt: 2H); 3.90 (mt: 1H); 4.76 (t, J=5.5 Hz: 1H); 6.99 (dd, J=5 and 1 Hz:

1H); 7.16 (dd, J=3 and 1 Hz: 1H); 7.43 (dd, J=5 and 3 Hz: 1H); 7.70 (d, J=8.5 Hz: 1H).

Ethyl (2R)-2-(acetylamino)-3-(3-thienyl)propanoate: 3.95 g of ammonium hydrogen carbonate and 35 cm$^3$ of deionized water are added to a stirred solution, under an inert atmosphere, of 2.41 g of ethyl 2-(acetylamino)-3-(3-thienyl)propanoate in 17 cm$^3$ of acetonitrile. 0.017 g of type-II α-chymotrypsin is added and the pH of the reaction medium is then in the region of 8. This mixture is stirred for 1 hour at room temperature and, after checking that the pH is still at 8, a further 0.017 g of type-II α-chymotrypsin is added. After stirring for 1 hour, with the pH remaining constant, a further 0.017 g of type-II α-chymotrypsin is introduced and stirring of the reaction mixture is continued for 19 hours at room temperature. The acetonitrile is evaporated off under reduced pressure (2 kPa) at a temperature in the region of 33° C. and 25 cm$^3$ of ethyl acetate are then added to the residual aqueous phase. The emulsion obtained is filtered through Celite and the aqueous phase is then extracted with twice 25 cm$^3$ of ethyl acetate. The organic phases are combined, washed with twice 15 cm$^3$ of sodium carbonate solution and then evaporated under reduced pressure (2 kPa) at a temperature in the region of 40° C. The solid residue is then dried in an oven under vacuum (10 Pa) at room temperature. 1.1 g of ethyl (2R)-2-(acetylamino)-3-(3-thienyl)propanoate are obtained in the form of a beige-colored solid melting at about 75° C.

Ethyl 2-(acetylamino)-3-(3-thienyl)-propanoate: 9.83 g of lithium iodide are added in a single portion to a stirred pale yellow solution, under an inert atmosphere, of 7.7 g of diethyl 2-(acetylamino)-2-(3-thienylmethyl)malonate in 62 cm$^3$ of dimethylformamide, and the resulting mixture is heated in an oil bath at a temperature in the region of 128° C. for 19 hours. 6.6 g of lithium iodide are added and heating is continued for 5 hours. The reaction medium is then evaporated under reduced pressure (2.4 kPa) at a temperature in the region of 55° C. The residual brown oil is taken up in 180 cm$^3$ of water and is extracted with 4 times 60 cm$^3$ of ethyl acetate. The organic phases are combined, washed with 30 cm$^3$ of saturated aqueous sodium chloride solution, dried over magnesium sulfate and then evaporated under reduced pressure (2 kPa) at a temperature in the region of 62° C., to give 5.34 g of a brown oil which crystallizes under cold conditions. The crystals are taken up in 40 cm$^3$ of petroleum ether, ground in a mortar and then filtered off on a sinter funnel and dried in an oven under vacuum (10 Pa) at room temperature. 4.9 g of ethyl 2-(acetylamino)-3-(3-thienyl)propanoate are obtained in the form of an off-white solid melting at about 60° C. $^1$H NMR spectrum (400 MHz, (CD$_3$)$_2$SO-d$_6$, δ in ppm) 1.14 (t, J=7 Hz: 3H); 1.84 (s: 3H); 2.93 (dd, J=14 and 9 Hz: 1H); 3.03 (dd, J=14 and 5.5 Hz: 1H); 4.06 (mt: 2H); 4.44 (mt: 1H); 7.02 (dd, J=5 and 1 Hz: 1H); 7.24 (mt: 1H); 7.45 (dd, J=5 and 3 Hz: 1H); 8.31 (d, J=8 Hz: 1H).

Diethyl 2-(acetylamino)-2-(3-thienylmethyl)malonate: 1.54 g of sodium are added, with stirring under an inert atmosphere, to 115 cm$^3$ of absolute ethanol. After total consumption of the sodium, 14.55 g of diethyl acetamidomalonate are added, followed by heating at a temperature in the region of 78° C. for 20 minutes. A solution of 16.5 g of freshly prepared 3-(bromomethyl)thiophene in 50 cm$^3$ of ethanol is then added and heating is continued at this same temperature for 19 hours. The reaction medium, which contains an insoluble white material, is cooled to a temperature in the region of 0° C. and is then filtered through a sinter funnel. The filtrate is concentrated under reduced pressure (2 kPa) at a temperature in the region of 40° C. and is then filtered through a sinter funnel. The crystals are taken up in 100 cm$^3$ of water, filtered again, washed with petroleum ether and dried in a fume cupboard at room temperature. 1.45 g of diethyl 2-(acetylamino)-2-(3-thienylmethyl) malonate are obtained in the form of a white solid melting at about 92° C. After evaporation of the filtration solvent in ambient air, the residue is taken up in 150 cm$^3$ of water and is then filtered on a sinter funnel. The yellowish solid obtained is washed with 50 cm$^3$ of water and is then dissolved in 25 cm$^3$ of absolute ethanol, followed by crystallization by addition of 25 cm$^3$ of water. After filtration, washing with 3 times 30 cm$^3$ of petroleum ether and then drying in a fume cupboard at room temperature, 6.57 g of diethyl 2-(acetylamino)-2-(3-thienylmethyl)malonate are obtained in the form of a white solid melting at about 92° C. $^1$H NMR spectrum (300 MHz, (CD$_3$)$_2$SO-d$_6$, δ in ppm): 1.18 (t, J=7 Hz: 6H); 1.98 (s: 3H); 3.50 (s: 2H); 4.16 (q, J=7 Hz: 4H); 6.80 (broad d, J=5 Hz: 1H); 7.14 (broad s: 1H); 7.46 (dd, J=5 and 3 Hz: 1H); 8.20 (broad s: 1H).

3-(Bromomethyl)thiophene can be prepared according to J. Gourier and P. Cannone; Bull. Soc. Chim. Fr. 1971, 3299–3306.

EXAMPLE 6

[3-(2-Amino-4,5-dihydrothiazol-4-yl)phenyl]-(1-iminoethyl)amine 0.15 g of benzyl ethanimidothioate hydrochloride and then 5 cm$^3$ of ethanol are added, under an inert atmosphere and at a temperature in the region of 0° C., to a stirred solution of 0.14 g of 4-(3-aminophenyl)-4,5-dihydro-1,3-thiazol-2-ylamine in 15 cm$^3$ of ethanol. The mixture is stirred for 1 hour at about 0° C. and then for 2 hours at a temperature in the region of 20° C. A further 0.030 g of benzyl ethanimidothioate is added to complete the reaction, after which the mixture is maintained at a temperature in the region of 45° C. for 24 hours. The reaction medium is evaporated under reduced pressure (5 kPa) at a temperature in the region of 40° C. The residue obtained is taken up in 30 cm$^3$ of water and the solution is washed with 30 cm$^3$ of dichloromethane. The aqueous solution is concentrated under the above conditions and the solid obtained is then triturated from diethyl ether, filtered, air-dried and purified by chromatography at atmospheric pressure on a column of silica gel (particle size 40–63µ; mass 63 g), eluting with a dichloromethane/methanol/aqueous ammonia mixture (12/3/0.5 by volume). The fractions containing the expected product are collected. These fractions are combined and then evaporated under reduced pressure (5 kPa) at a temperature in the region of 40° C. 0.100 g of [3-(2-amino-4,5-dihydrothiazol-4-yl)phenyl]-(1-iminoethyl)amine is obtained in the form of a white solid melting at 180° C. $^1$H NMR spectrum (250 MHz, (CD$_3$)$_2$SO-d$_6$, with addition of a few drops of CD$_3$COOD-d$_4$, δ in ppm): 2.28 (unres. mult.: 3H); 3.18 (dd, J=12.5 and 8.5 Hz: 1H); 3.80 (dd, J=12.5 and 8.5 Hz: 1H); 5.30 (t, J=8.5 Hz: 1H); 7.21 (broad d, J=8.5 Hz: 1H); 7.27 (broad s: 1H); 7.36 (broad d, J=8.5 Hz: 1H); 7.49 (broad t, J=8.5: Hz: 1H).

Benzyl ethanimidothioate hydrochloride can be obtained by applying the method described in patent WO 96/19440.

4-(3-Aminophenyl)-4,5-dihydro-1,3-thiazol-2-ylamine: 3 g of zinc powder are added, with stirring at a temperature in the region of 20° C., to a suspension of 2.4 g of 4-(3-nitrophenyl)-4,5-dihydro-1,3-thiazol-2-ylamine hydrochloride in 50 cm$^3$ of 85% by volume of acetic acid. After stirring for 20 minutes at room temperature, the reaction medium is filtered; the filter cake is washed with 10 cm³ of water and the filtrate is then concentrated under reduced pressure (5 kPa) at a temperature in the region of 50° C. The residue obtained is taken up in methanol and then in diethyl ether, and concentrated under the same conditions as above. This operation is repeated a second time. The product obtained is taken up in 100 cm³ of acetonitrile and filtered. The filtrate is concentrated as above and taken up in 60 cm³ of water. The insoluble material is filtered off, while the filtrate is made alkaline by addition of 7 cm³ of aqueous 1N sodium hydroxide solution. The insoluble material is separated out by filtration and the filtrate is again concentrated as above, and taken up in 40 cm³ of a dichloromethane/methanol/aqueous ammonia mixture (40/5/0.5 by volume). The insoluble material is filtered off and the filtrate is concentrated as above. 4.2 g of a yellow oil are obtained, and are purified by chromatography at atmospheric pressure on a column of silica gel (particle size 40–63μ; 100 g of silica), eluting with a dichloromethane/methanol/aqueous ammonia mixture (40/5/0.5 by volume). The fractions containing the product are combined and then concentrated (5 kPa) at a temperature in the region of 40° C. 0.73 g of 4-(3-aminophenyl)-4,5-dihydro-1,3-thiazol-2-ylamine is obtained in the form of a yellow solid melting at 152° C.

4-(3-Nitrophenyl)-4,5-dihydro-1,3-thiazol-2-ylamine hydrochloride: The process is performed as in Example 2, starting with 4.77 g of N-(tert-butyl)-N'-[2-hydroxy-1-(3-nitrophenyl)ethyl]thiourea and 44 cm³ of aqueous 6N hydrochloric acid, and this mixture is maintained at a temperature in the region of 100° C. for 2 h 30 min. After an identical work-up, 3.1 g of 4-(3-nitrophenyl)-4,5-dihydro-1,3-thiazol-2-ylamine hydrochloride are obtained in the form of a cream-colored solid melting at 232° C.

N-(tert-Butyl)-N'-[2-hydroxy-1-(3-nitrophenyl)ethyl]thiourea: The process is performed as in Example 2, starting with 5.1 g of 2-amino-2-(3-nitrophenyl)-1-ethanol in 170 cm³ of ethanol containing 85 cm³ of dichloromethane and 4.6 cm³ of tert-butyl isothiocyanate, at a temperature in the region of 20° C. for 3 days and then at a temperature in the region of 60° C. for 7 hours. After addition of a further 0.35 cm³ of tert-butyl isothiocyanate and 16 hours at a temperature in the region of 60° C., an identical work-up gives 5.7 g of N-(tert-butyl)-N'-[2-hydroxy-1-(3-nitrophenyl)ethyl]thiourea in the form of an ocher-colored solid melting at 162° C.

2-Amino-2-(3-nitrophenyl)-1-ethanol: The process is performed as in Example 2, starting with 1 g of ethyl 3-nitrophenylglycinate in 20 cm³ of ethanol with 0.255 g of sodium borohydride and 20 hours at a temperature in the region of 20° C. After an identical work-up, 0.200 g of 2-amino-2-(3-nitrophenyl)-1-ethanol is obtained in the form of an ocher-yellow paste. ($R_f$=0.18 in a 90/10 by volume mixture of dichloromethane/methanol, on a Merck 60F$_{254^R}$ silica plate).

Ethyl 3-nitrophenylglycinate: 2 g of 3-nitrophenylglycine are heated for 20 hours with stirring at a temperature in the region of 100° C. in 100 cm³ of absolute ethanol containing 20 cm³ of 6.5N hydrochloric ethanol. The suspension is filtered at a temperature in the region of 50° C.; the filtrate is concentrated under reduced pressure (5 kPa) at a temperature in the region of 40° C. The residue obtained is taken up in water and then extracted with about 100 cm³ of ethyl acetate. The aqueous phase is made alkaline by addition of sodium carbonate until a pH in the region of 10 is obtained. The medium is extracted with ethyl acetate; the combined extracts are washed with aqueous sodium chloride solution, dried over magnesium sulfate and then concentrated under reduced pressure (5 kPa) at 40° C. 1 g of ethyl 3-nitrophenylglycinate is obtained in the form of a yellow oil. ($R_f$=0.38 in a 95/5 by volume mixture of dichloromethane/methanol, on a Merck 60F$_{254^R}$ silica plate).

3-Nitrophenylglycine: 1.01 g of potassium nitrate are added slowly, at a temperature in the region of 0° C. with stirring, to a mixture of 1.51 g of D-(−)-α-phenylglycine in 6 cm³ of 95% sulfuric acid and the temperature is then allowed to return to about 20° C. The solution obtained is poured into 30 cm³ of ice-cold water and then brought to pH 7 by addition of 18.5 cm³ of 10N sodium hydroxide, at a temperature below 5° C. The mixture is stirred for 2 hours and then filtered. The filter cake obtained is washed with twice 50 cm³ of water and then dried. 0.60 g of 3-nitrophenyl-glycine is obtained in the form of a cream-colored solid melting at 230° C.

EXAMPLE 7

(+)-(4R)-4-Benzyl-4,5-dihydro-1,3-thiazol-2-ylamine hydrochloride

The process is performed as in Example 2, starting with 2 g of N-(tert-butyl)-N'-[(1R)-2-hydroxy-1-(phenylmethyl)ethyl]thiourea and 20 cm³ of aqueous 6N hydrochloric acid. The reaction lasts 1 h 30 min. After cooling the reaction mass to a temperature in the region of 0° C., the solution is concentrated under reduced pressure (5 kPa) at a temperature in the region of 40° C. Crystallization of the oil obtained is initiated by addition of diethyl ether. The resulting precipitate is spin-filtered, washed with twice 10 cm³ of diethyl ether and then dried under reduced pressure (10 Pa) at a temperature in the region of 60° C. The product is purified by taking it up in 100 cm³ of dichloromethane with stirring for 30 minutes. After filtration of the suspension, the filter cake is washed with twice 10 cm³ of dichloromethane and is then dried under the same conditions as above. 1.1 g of (+)-(4R)-4-phenylmethyl-4,5-dihydro-1,3-thiazol-2-ylamine hydrochloride are obtained in the form of a white solid melting at 168° C. ($\alpha_D^{20}$=+8.7±0.3 at a concentration of 1% in methanol).

N-(tert-Butyl)-N'-[(1R)-2-hydroxy-1-(benzyl)ethyl]thiourea: The process is performed as in Example 2, starting with 5 g of (R)-(+)2-amino-3-phenyl-1-propanol in 50 cm³ of ethanol and 5.7 g of tert-butyl isothiocyanate at a temperature in the region of 20° C. for 16 hours. After an identical work-up, 8.7 g of N-(tert-butyl)-N'-[(1R)-2-hydroxy-1-(phenylmethyl)ethyl]thiourea are obtained in the form of a white solid melting at 107° C.

EXAMPLE 8

(+)-(4R)-4-(3-Carboxybenzyl)-4,5-dihydro-1,3-thiazol-2-ylamine hydrochloride

The process is performed as in Example 2, starting with 2.31 g of N-(tert-butyl)-N'-[(1R)-2-hydroxy-1-(3-carboxybenzyl)ethyl]thiourea in 25 cm³ of 6N hydrochloric acid for 18 hours. After concentration of the reaction mixture under reduced pressure (5 kPa) at a temperature in the region of 55° C., the residue is taken up in 20 cm³ of acetone and is then concentrated again under the above conditions. The residue obtained is purified by chromatography under a pressure of 50 kPa of argon, on a column of silica gel (particle size 40–63μ; mass of silica: 100 g), eluting with a chloroform/methanol/20% aqueous ammonia mixture (12/6/1 by volume) and collecting 30 cm³ fractions. Fractions 16 to 38 are combined and then concentrated under reduced pressure (5 kPa) at a temperature in the region of 40° C. The solid obtained is dissolved in 10 cm³ of aqueous 6N hydrochloric acid and is then concentrated as previously. After taking up the residue obtained in 10 cm³ of acetone, the resulting insoluble material is filtered off; the filtrate is concentrated as above. A solid is obtained, which is dried for 5 hours in an oven at 40° C., under reduced pressure (8 Pa). 0.650 g of (+)-(4R)-4-(3-carboxybenzyl)-4,5-dihydro-1,3-thiazol-2-ylamine hydrochloride is obtained in the form of a beige-colored solid melting at 151° C. ($\alpha_D^{20}$=+13.4±0.6 at a concentration of 0.5% in methanol).

N-(tert-Butyl)-N'-[(1R)-2-hydroxy-1-(3-carboxybenzyl) ethyl]thiourea: The process is performed as in Example 2, starting with 1.82 g of (2R)-2-amino-3-(3-carboxyphenyl)-1-propanol hydrochloride in 20 cm³ of ethanol, 4.2 cm³ of triethylamine and 1.7 cm³ of tert-butyl isothiocyanate. After heating for 21 hours at a temperature in the region of 60° C. and an identical work-up, 2.31 g of N-(tert-butyl)-N'-[(1R)-2-hydroxy-1-(3-carboxybenzyl)ethyl]thiourea are obtained in the form of a light brown foam. ($R_f$=0.33 in a 12/6/1 by volume mixture of chloroform/methanol/aqueous ammonia, on a Merck $60F_{254^R}$ silica plate).

(2R)-2-Amino-3-(3-carboxyphenyl)-1-propanol hydrochloride: The process is performed as in Example 2, starting with 1.96 g of N-[(1R)-2-hydroxy-1-(3-carboxybenzyl) ethyl]acetamide in 14 cm³ of aqueous 6N hydrochloric acid heated at a temperature in the region of 100° C. for 17 hours. After an identical work-up, 2.16 g of (2R)-2-amino-3-(3-carboxyphenyl)-1-propanol hydrochloride are obtained in the form of a white solid melting at 194° C.

N-[(1R)-2-Hydroxy-1-(3-cyanobenzyl)ethyl]-acetamide: The process is performed as in Example 2, starting with 3.3 g of ethyl (2R)-2-acetylamino-3-(3-cyanophenyl) propanoate and 1.23 g of sodium borohydride in 50 cm³ of ethanol and working at a temperature in the region of –30° C. After stirring for 16 hours at a temperature in the region of 20° C., the reaction medium is evaporated under reduced pressure (5 kPa) at a temperature in the region of 45° C. and the residue obtained is then stirred in a mixture of 100 cm³ of water and 100 cm³ of ethyl acetate. The organic phase is separated out after settling has taken place and the aqueous phase is extracted with twice 100 cm³ of ethyl acetate. The organic extracts are combined and then washed with twice 50 cm³ of water, dried over magnesium sulfate, filtered and evaporated under reduced pressure (5 kPa) at a temperature in the region of 45° C. 2.13 g of N-[(1R)-2-hydroxy-1-(3-cyanobenzyl)ethyl]acetamide are obtained in the form of a white solid. ($\alpha_D^{20}$=+7.5±0.6 at a concentration of 0.5% in methanol).

Ethyl (2R)-2-acetylamino-3-(3-cyanophenyl)-propanoate: The process is performed as in Example 2, starting with 11.39 g of ethyl (2RS)-2-acetylamino-3-(3-cyanophenyl)propanoate, 17.39 g of ammonium hydrogen carbonate and 0.1 g of α-chymotrypsin in 200 cm³ of water and 70 cm³ of acetonitrile. After stirring for 24 hours at a temperature in the region of 20° C. and an identical work-up, 5.40 g of ethyl (2R)-2-acetylamino-3-(3-cyanophenyl) propanoate are obtained in the form of a beige-colored solid. ($R_f$=0.76 in a 40/10/20 by volume mixture of n-butanol/acetic acid/water, on a Merck $60F_{254^R}$ silica plate).

Ethyl (2RS)-2-acetylamino-3-(3-cyanophenyl)-propanoate: The process is performed as in Example 5, starting with 14.9 g of ethyl 2-acetylamino-2-(3-cyanobenzyl)malonate, 30 g of anhydrous lithium iodide and 150 cm³ of dry dimethylformamide. After stirring for 5 hours at a temperature in the region of 150° C., the reaction mass is cooled to room temperature. 1500 cm³ of water are added and the mixture is extracted with 3 times 300 cm of ethyl acetate. The extracts are combined, dried over magnesium sulfate, filtered and concentrated under reduced pressure (5 kPa) at a temperature in the region of 45° C. After drying in an oven at a temperature in the region of 40° C. under reduced pressure (10 Pa), 11.39 g of ethyl (2RS)-2-acetylamino-3-(3-cyanophenyl)propanoate are obtained in the form of a beige-colored paste. ($R_f$=0.51 in a 90/10 by volume mixture of ethyl acetate/cyclohexane, on a Merck $60F_{254^R}$ silica plate).

Ethyl 2-acetylamino-2-(3-cyanobenzyl)-malonate: The process is performed as in Example 5, starting with 27.7 g of diethyl acetamidomalonate, 25 g of 3-cyanobenzyl bromide and 3.2 g of sodium in 400 cm³ of absolute ethanol. After an identical work-up, the cooled reaction mass is filtered and the filter cake is washed with twice 50 cm³ of ethanol and then with twice 50 cm³ of water. After drying in an oven under reduced pressure (10 Pa) at a temperature in the region of 40° C., 21.98 g of a white powder are obtained. The filtrate is evaporated under reduced pressure (5 kPa) at a temperature in the region of 50° C.; a foam is obtained, which is taken up in 100 cm³ of water and extracted with 100 cm³ of ethyl acetate and then twice 50 cm³ of the same solvent. The extracts are combined, washed with twice 50 cm³ of water, dried over magnesium sulfate, filtered and evaporated under reduced pressure (5 kPa) at a temperature in the region of 45° C. The residue obtained is taken up in 20 cm³ of ethanol. The crystals obtained are spin-filtered, washed with ethanol and dried in an oven under reduced pressure (10 Pa) at a temperature in the region of 40° C. The two crops are combined to give 31.94 g of ethyl 2-acetylamino-2-(3-cyanobenzyl)-malonate in the form of a white powder melting at 138° C.

EXAMPLE 9

(+)-(4R)-4-(4-Aminobutyl)-4,5-dihydro-1,3-thiazol-2-ylamine dihydrochloride

The process is performed as in Example 1, starting with 5.9 g of benzyl (5R)-5-{[(tert-butylamino)carbothioyl] amino}-6-hydroxyhexylcarbamate in 40 cm³ of aqueous 6N hydrochloric acid at a temperature in the region of 100° C. for 3 hours. After concentration of the reaction medium under reduced pressure (5 kPa) at a temperature in the region of 50° C., the residue obtained is taken up in ethanol and then concentrated again under the above conditions. The paste obtained is crystallized by trituration from an ethanol/methanol mixture (8/2 by volume). The crystals are filtered off, washed with acetonitrile and air-dried. 1.3 g of (+)-(4R)-4-(4-aminobutyl)-4,5-dihydro-1,3-thiazol-2-ylamine dihydrochloride are obtained in the form of a white solid melting at 188° C. ($\alpha_D^{20}$=+16.2±0.7 at a concentration of 0.5% in methanol).

Benzyl (5R)-5-{[(tert-butylamino)-carbothioyl]amino}-6-hydroxyhexylcarbamate: 1.78 g of lithium chloride and then 1.6 g of sodium borohydride are added, under an inert atmosphere, to a stirred solution of 12.7 g of ethyl (2R)-6-{[(benzyloxy)-carbonyl]amino}-2-{[(tert-butylamino) carbothioyl]-amino}hexanoate in 130 cm³ of ethanol and 65 cm³ of tetrahydrofuran, cooled to between 0° C. and 5° C. After stirring for 16 hours at a temperature in the region of 20° C., a further 0.4 g of borohydride is added and the mixture is maintained at about 80° C. for 4 hours. The reaction medium is filtered and the filter cake is washed with ethanol. The filtrate is concentrated under reduced pressure (5 kPa) at a temperature in the region of 40° C. and the residue obtained is taken up in a dichloromethane/ethyl acetate mixture (85/15 by volume) and left under cold conditions at about 5° C. The crystalline product is spin-filtered and purified by chromatography at atmospheric pressure on a column of silica gel (particle size 40–63µ; mass of silica: 600 g), eluting with a dichloromethane/ethyl acetate mixture (85/15 by volume). The fractions containing the expected product are collected. These fractions are combined and then concentrated under reduced pressure (5 kPa) at a temperature in the region of 40° C. 6.9 g of benzyl (5R)-5-{[(tert-butylamino)carbothioyl]amino}-6-hydroxyhexylcarbamate are obtained in the form of a colorless oil. ($\alpha_D^{20}$=+24.0±0.8 at a concentration of 0.5% in methanol).

Ethyl (2R)-6-{[(benzyloxy)carbonyl]amino}-2-{[(tert-butylamino)carbothioyl]amino}hexanoate: The process is performed as in Example 2, starting with 7.4 g of ethyl (2R)-2-amino-6-{[(benzyloxy)carbonyl]-amino}hexanoate with 5 cm$^3$ of tert-butyl isothiocyanate in 200 cm$^3$ of anhydrous ethanol at a temperature in the region of 20° C. for 20 hours. The reaction is completed by addition of a further 1 cm$^3$ of isothiocyanate and heating for 2 hours at a temperature in the region of 80° C. The reaction medium is concentrated under reduced pressure (5 kPa) at a temperature in the region of 40° C. The residue obtained is taken up in ether and concentrated again under the above conditions. 13 g of ethyl (2R)-6-{[(benzyloxy)carbonyl]amino}-2-{[(tert-butylamino)carbothioyl]amino}hexanoate are obtained in the form of a colorless oil. ($\alpha_D^{20}$=−12.5±0.5 at a concentration of 0.5% in methanol).

Ethyl (2R)-2-amino-6-{[(benzyloxy)carbonyl]-amino}hexanoate: 3.9 cm$^3$ of thionyl chloride are added to a stirred suspension of 7.9 g of (2R)-2-amino-6-{[(benzyloxy)carbonyl]amino}hexanoic acid (Nε-CBZ-D-lysine) in 120 cm$^3$ of anhydrous ethanol cooled to a temperature in the region of −25° C. The mixture is stirred for 3 hours at this temperature and is then allowed to warm to about 20° C. After leaving for 3 days, the reaction mass is concentrated under reduced pressure (5 kPa) at a temperature in the region of 40° C. The residue obtained is taken up in 200 cm$^3$ of ethyl acetate and the resulting solution is washed with aqueous sodium carbonate solution and then with aqueous sodium chloride solution. The organic solution is dried over magnesium sulfate, filtered and concentrated under reduced pressure (5 kPa) at a temperature in the region of 40° C. 7.4 g of ethyl (2R)-2-amino-6-{[(benzyloxy)-carbonyl]amino}hexanoate are obtained in the form of a pale yellow oil. ($\alpha_D^{20}$=−11.7±0.6 at a concentration of 0.5% in methanol).

EXAMPLE 10

(−)-(4S)-4-(3-Nitrobenzyl)-4,5-dihydro-1,3-thiazol-2-ylamine hydrochloride

The process is performed as in Example 2, starting with N-(tert-butyl)-N'-[(1S)-2-hydroxy-1-(3-nitrobenzyl)ethyl]thiourea in 80 cm$^3$ of aqueous 6N hydrochloric acid. The heating time is 7 hours. The product is isolated in an identical manner and then purified by chromatography under an argon pressure of 80 kPa, on a column of silica gel (particle size 40–63µ; diameter 3.5 cm; height 30 cm), eluting with a dichloromethane/methanol mixture (95/5 by volume). The fractions corresponding to the expected product are collected. These fractions are combined and then concentrated under reduced pressure (5 kPa) at a temperature in the region of 40° C. 3.90 g of (−)-(4S)-4-(3-nitrobenzyl)-4,5-dihydro-1,3-thiazol-2-ylamine hydrochloride are obtained in the form of a white solid melting at 220° C. ($\alpha_D^{20}$=−18.4±0.05 at a concentration of 0.5% in methanol).

N-(tert-Butyl)-N'-[(1S)-2-hydroxy-1-(3-nitrobenzyl)ethyl]thiourea: The process is performed as in Example 2, starting with 5.65 g of (2S)-2-amino-3-(3-nitrophenyl)-1-propanol hydrochloride, 3.7 cm$^3$ of tert-butyl isothiocyanate and 3.41 cm$^3$ of triethylamine in 60 cm$^3$ of ethanol. After stirring for 3 days at a temperature in the region of 20° C. and then heating for 30 minutes at a temperature in the region of 60° C., 3.7 cm$^3$ of tert-butyl isothiocyanate are added to the reaction medium and heating is then continued for a further 3 hours at the same temperature. After an identical work-up, 6.45 g of N-(tert-butyl)-N'-[(1S)-2-hydroxy-1-(3-nitrobenzyl)ethyl]thiourea are obtained in the form of a yellow foam. ($R_f$=0.61 in a 40/5/0.5 by volume mixture of dichloromethane/methanol/aqueous ammonia, on a Merck 60F$_{254}$$^R$ silica plate).

(2S)-2-Amino-3-(3-nitrophenyl)-1-propanol hydrochloride: The process is performed as in Example 2, starting with 5.8 g of N-[(1S)-2-hydroxy-1-(3-nitrobenzyl)ethyl]acetamide in 60 cm$^3$ of aqueous 6N hydrochloric acid, for 10 hours at a temperature in the region of 100° C. After cooling the medium, the precipitate is filtered off and then washed with 30 cm$^3$ of acetone and 3 times 50 cm$^3$ of ether, and dried in an oven under reduced pressure (10 Pa) at a temperature in the region of 60° C. The filtrate is concentrated under reduced pressure (5 kPa) at about 50° C. The residue obtained is taken up in 30 cm$^3$ of diethyl ether and the crystals are filtered off, washed with twice 30 cm$^3$ of ether and dried in an oven under the same conditions as above. The 2 crops crystallized are combined. 5.65 g of (2S)-2-amino-3-(3-nitrophenyl)-1-propanol hydrochloride are obtained in the form of a beige-colored solid melting at 188° C.

N-[(1S)-2-Hydroxy-1-(3-nitrobenzyl)ethyl]-acetamide: The process is performed as in Example 2, starting with 7.15 g of ethyl (2S)-2-(acetylamino)-3-(3-nitrophenyl)propanoate and 1.46 g of sodium borohydride in 70 cm$^3$ of ethanol. After an identical work-up, 5.8 g of N-[(1S)-2-hydroxy-1-(3-nitrobenzyl)-ethyl]acetamide are obtained in the form of a white solid melting at 131° C.

Ethyl (2S)-2-(acetylamino)-3-(3-nitrophenyl)-propanoate can be prepared according to Rivier et al., J. Med. Chem. (1995), 2658.

EXAMPLE 11

(−)-(4S,5S)-4-Benzyl-5-methyl-4,5-dihydro-1,3-thiazol-2-ylamine

The process is performed as in Example 3, starting with 3.9 g of diastereoisomer A of the N-(tert-butyl)-N'-((1S)-1-benzyl-2-hydroxypropyl)thiourea in 46 cm$^3$ of aqueous 6N hydrochloric acid. After heating for 5 hours at a temperature in the region of 100° C., the reaction mass is concentrated under reduced pressure (5 kPa) at a temperature in the region of 50° C. The oil obtained is dissolved in 50 cm$^3$ of water; the solution is washed with twice 50 cm$^3$ of dichloromethane. The aqueous phase is made alkaline by addition of 3 cm$^3$ of 30% caustic soda and then extracted with 3 times 50 cm$^3$ of dichloromethane. The organic extracts are combined and dried over sodium sulfate. After filtration and concentration under reduced pressure (5 kPa) at a temperature in the region of 40° C., 2.5 g of (−)-(4S,5S)-4-benzyl-5-methyl-4,5-dihydro-1,3-thiazol-2-ylamine are obtained in the form of a white solid melting at 89° C. (trans isomer). ($\alpha_D^{20}$=−87.3±1.3 at a concentration of 0.5% in methanol).

N-(tert-Butyl)-N'-((1S)-1-benzyl-2-hydroxypropyl) thiourea: The process is performed as in Example 3, starting with 9.5 g of (3S)-3-amino-4-phenyl-2-butanol in 80 cm³ of ethanol and in the presence of 7.86 cm³ of tert-butyl isothiocyanate. After stirring the mixture for 3 days at a temperature in the region of 20° C. and an identical work-up, 15.9 g of an oil are obtained, and are purified by chromatography under a pressure of argon (50 kPa), on a column of silica gel (particle size 40–63µ; diameter 5 cm; height of silica 38 cm), eluting with a dichloromethane/ethyl acetate mixture (95/5 by volume). The fractions containing diastereoisomer A are combined and evaporated under reduced pressure (5 kPa) at a temperature in the region of 40° C. 3.98 g of diastereoisomer A of N-(tert-butyl)-N'-((1S)-1-benzyl-2-hydroxypropyl)thiourea are obtained in the form of a white solid melting at 156° C. By concentrating the fractions corresponding to diastereoisomer B under the same conditions, 0.72 g of diastereoisomer B of N-(tert-butyl)-N'-((1S)-1-benzyl-2-hydroxypropyl)thiourea is obtained in the form of a yellow solid melting at 116° C.

(3S)-3-Amino-4-phenyl-2-butanol: The process is performed as in Example 3, starting with 17.6 g of tert-butyl (1S)-1-benzyl-2-hydroxypropylcarbamate in 145 cm³ of dioxane and 61 cm³ of 6.5N hydrochloric dioxane, stirring for 16 hours at a temperature in the region of 20° C. After an identical work-up, 9.56 g of (3S)-3-amino-4-phenyl-2-butanol are obtained in the form of an orange-colored oil as a mixture of the two diastereoisomers (80/20). ($R_f$=0.25 in a 40/5/0.5 by volume mixture of dichloromethane/methanol/aqueous ammonia, on a Merck 60F$_{254^R}$ silica plate).

tert-Butyl (1S)-1-benzyl-2-hydroxypropyl-carbamate: The process is performed as in Example 3, starting with 2.66 g of tert-butyl (1S)-1-benzyl-2-oxopropylcarbamate in 25 cm³ of ethanol, with 0.58 g of sodium borohydride. After 4 h 30 min at a temperature in the region of 20° C., the reaction mixture is worked up in an identical manner. 2.7 g of tert-butyl (1S)-1-benzyl-2-hydroxypropylcarbamate are obtained in the form of a white solid melting at 125° C., as a mixture of the two diastereoisomers (70/30).

tert-Butyl (1S)-1-benzyl-2-oxopropyl-carbamate: The process is performed as in Example 3, starting with 5 g of tert-butyl (1S)-1-benzyl-2-[methoxy(methyl)amino]-2-oxoethylcarbamate, 16 cm³ of a 1M solution of methylmagnesium bromide in ether, and 100 cm³ of anhydrous tetrahydrofuran. Once the reaction is complete, the reaction medium is stirred for 18 hours at a temperature in the region of 20° C. After an identical work-up, 3.91 g of an orange-colored oil are obtained, and are purified by chromatography at atmospheric pressure on a column of silica gel (particle size 63–200µ; diameter 3.5 cm; height 20 cm), eluting with dichloromethane. The fractions corresponding to the expected product are collected. These fractions are combined and then concentrated under reduced pressure (5 kPa) at a temperature in the region of 40° C. 2.82 g of tert-butyl (1S)-1-benzyl-2-oxopropylcarbamate are obtained in the form of a white solid melting at 62° C.

tert-Butyl (1S)-1-benzyl-2-[methoxy(methyl)-amino]-2-oxoethylcarbamate: The process is performed as in Example 3, starting with 26.5 g of L-N-Boc-phenylalanine, 22 cm³ of N-methylmorpholine, 13 cm³ of isobutyl chloroformate and 10.14 g of N,O-dimethyl-hydroxylamine hydrochloride in 300 cm³ of dichloromethane. The product is worked up in an identical manner and then purified by chromatography at atmospheric pressure on a column of silica gel (particle size 63–200µ; diameter 6 cm; height 25 cm), eluting with a dichloromethane/methanol mixture (97/3 by volume). The fractions containing the expected product are collected. These fractions are combined and then concentrated under reduced pressure (5 kPa) at a temperature in the region of 40° C. 17.1 g of tert-butyl (1S)-1-benzyl-2-[methoxy(methyl)amino]-2-oxoethylcarbamate are obtained in the form of a colorless oil. ($R_f$=0.65 in a 97/3 by volume mixture of dichloromethane/methanol, on a Merck 60F$_{254^R}$ silica plate).

EXAMPLE 12

(−)-(4S)-4-(4-Aminobutyl)-4,5-dihydro-1,3-thiazol-2-ylamine dihydrochloride

The process is performed as in Example 9, starting with 0.59 g of ethyl (2S)-6-{[(benzyloxy)-carbonyl]amino}-2-{[(tert-butylamino)carbothioyl]-amino}hexanoate in 6 cm³ of 6N hydrochloric acid. After concentration of the reaction medium under the same conditions, the foam obtained is taken up 3 times in diethyl ether and the phases are separated each time after settling has taken place, and the remaining insoluble material is then taken up in 10 cm³ of acetonitrile. The resulting crystalline product is spin-filtered, washed with hot acetonitrile and then dried under reduced pressure (5 kPa) at a temperature in the region of 20° C. 0.34 g of (−)-(4S)-4-(4-amino-butyl)-4,5-dihydro-1,3-thiazol-2-ylamine dihydro-chloride in the form of cream-colored crystals melting at 170° C. ($\alpha_D^{20}$=−15.5±0.6 at a concentration of 0.5% in methanol).

Ethyl (2S)-6-{[(benzyloxy)carbonyl]amino}-2-{[(tert-butylamino)carbothioyl]amino}hexanoate: The process is performed as in Example 9, starting with 0.42 g of benzyl (5S)-5-amino-6-hydroxyhexylcarbamate and 0.24 cm³ of tert-butyl isothiocyanate in 30 cm³ of ethanol at a temperature in the region of 20° C. for 3 days. The reaction is completed by addition of a further 0.48 cm³ of isothiocyanate followed by heating for 1 hour at a temperature in the region of 80° C. After an identical work-up, 0.6 g of ethyl (2S)-6-{[(benzyloxy)carbonyl]amino}-2-{[(tert-butylamino)-carbothioyl]amino}hexanoate is obtained in the form of a beige-colored oil with a tendency to crystallize. ($R_f$=0.62 in a 90/10 by volume mixture of dichloromethane/methanol, on a Merck 60F$_{254^R}$ silica plate).

Benzyl (5S)-5-amino-6-hydroxyhexylcarbamate: A mixture of 4 g of benzyl (5S)-5-{[(tert-butyloxy)carbonyl]amino}-6-hydroxyhexylcarbamate, 30 cm³ of trifluoroacetic acid and 20 cm³ of ethanol is stirred at a temperature in the region of 20° C. for 2 hours. After concentration of the reaction medium under reduced pressure (5 kPa) at a temperature in the region of 40° C., the residue obtained is taken up in 50 cm³ of water and washed with twice 100 cm³ of diethyl ether. The aqueous phase is separated out after settling has taken place, basified with sodium carbonate to pH 9–10 and then extracted with 3 times 100 cm³ of dichloromethane. The combined extracts are washed with aqueous sodium chloride solution and then dried on magnesium sulfate, filtered and concentrated under reduced pressure (5 kPa) at a temperature in the region of 40° C. 2.0 g of benzyl (5S)-5-amino-6-hydroxyhexylcarbamate are obtained in the form of a white solid melting at 82° C.

Benzyl (5S)-5-{[(tert-butyloxy)carbonyl]-amino}-6-hydroxyhexylcarbamate: The process is performed as in Example 9, starting with 7 g of methyl (2S)-6-{[(benzyloxy)carbonyl]amino}-2-{[(tert-butyloxy)carbonyl]amino}hexanoate in 70 cm³ of ethanol, 35 cm³ of tetrahydrofuran, 1 g of lithium chloride and 0.81 g of sodium borohydride. After 16 hours at a temperature in the region of 20° C., the reaction mass is filtered and the filter cake is washed with ethanol. The resulting filtrate is concentrated under reduced pressure (5 kPa) at a temperature in the region of 40° C. After dissolving the residue obtained in 150 cm$^3$ of dichloromethane, washing with twice 100 cm$^3$ of aqueous sodium chloride solution and twice 100 cm$^3$ of water, drying over magnesium sulfate and finally concentrating under the same conditions as above, 5.2 g of benzyl (5S)-5-{[(tert-butyloxy)carbonyl]amino}-6-hydroxyhexylcarbamate are obtained in the form of a white solid melting at 67° C.

Methyl (2S)-6-{[[benzyloxy)carbonyl]amino}-2-{[(tert-butyloxy)carbonyl]amino}hexanoate: 4.8 g of di-tert-butyl dicarbonate are added, under an inert atmosphere, to a stirred solution of 6.6 g of Nε-CBZ-L-lysine methyl ester hydrochloride in 66 cm$^3$ of methanol and 66 cm$^3$ of tetrahydrofuran, cooled to a temperature in the region of 0° C., followed by addition of 5.7 cm$^3$ of triethylamine and 10 cm$^3$ of methanol. After stirring the mixture at a temperature in the region of 5° C. for 2 hours and then at about 20° C. for 2 hours, the reaction medium is concentrated under reduced pressure (5 kPa) at a temperature in the region of 40° C. The residue obtained is taken up in dichloromethane and the solution is washed with 100 cm$^3$ of water, dried over magnesium sulfate, filtered and concentrated under the same conditions as above. 7 g of methyl (2S)-6-{[(benzyloxy)carbonyl]amino}-2-{[(tert-butyloxy)-carbonyl]amino}hexanoate are obtained in the form of a cream-colored oil. ($R_f$=0.90 in a 90/10 by volume mixture of dichloromethane/methanol, on a Merck 60F$_{254}$$^R$ silica plate).

EXAMPLE 13

(4S,5R)-4-Benzyl-5-methyl-4,5-dihydro-1,3-thiazol-2-ylamine

The process is performed as in Example 3, starting with 0.7 g of diastereoisomer B of N-(tert-butyl)-N'-((1S)-1-benzyl-2-hydroxypropyl)thiourea which is heated to a temperature in the region of 100° C. for 5 hours in 8.3 cm$^3$ of aqueous 6N hydrochloric acid. After concentration of the reaction medium under reduced pressure (5 kPa) at a temperature in the region of 50° C., 50 cm$^3$ of water are added to the residue obtained and the solution is then extracted with 3 times 25 cm$^3$ of dichloromethane. The aqueous phase is made alkaline by addition of 0.5 cm$^3$ of 30% caustic soda and extracted with 3 times 50 cm$^3$ of dichloromethane. The extracts are combined, dried over sodium sulfate, filtered and then concentrated under reduced pressure (5 kPa) at a temperature in the region of 50° C. An oil is obtained, which is purified by chromatography under an argon pressure of 50 kPa, on a column of silica gel (particle size 40–63μ; diameter 2 cm; height 28 cm), eluting with a dichloromethane/methanol mixture (95/5 by volume). The fractions containing the expected product are collected. These fractions are combined and then concentrated under reduced pressure (5 kPa) at a temperature in the region of 40° C. 0.10 g of (4S)-4-benzyl-5-methyl-4,5-dihydro-1,3-thiazol-2-ylamine is obtained in the form of a pale pink solid melting at 90° C. to become pasty (mixture of diastereoisomers: 82% of cis [(4S,5R)-4-benzyl-5-methyl-4,5-dihydro-1,3-thiazol-2-ylamine] 18% of trans [(4S,5S)-4-benzyl-5-methyl-4,5-dihydro-1,3-thiazol-2-ylamine]). ($R_f$=0.15 in a 95/5 by volume mixture of dichloromethane/methanol, on a Merck 60F$_{254}$$^R$ silica plate).

EXAMPLE 14

(−)-(4R)-4-Butyl-4,5-dihydro-1,3-thiazol-2-ylamine oxalate

The process is performed as in Example 1, starting with 2.3 g of N-(tert-butyl)-N'-[(1R)-1-butyl-2-hydroxyethyl] thiourea in 32 cm$^3$ of aqueous 6N hydrochloric acid. After concentration under reduced pressure (5 kPa) at a temperature in the region of 50° C., the residue obtained is taken up in 10 cm$^3$ of water and then made alkaline by addition of 2 cm$^3$ of 30% caustic soda. After extraction with 3 times 50 cm$^3$ of dichloromethane, the organic extracts are combined and dried over sodium sulfate and concentrated under reduced pressure (5 kPa) at a temperature in the region of 40° C. 1.37 g of a yellow oil are obtained, the oxalate of which is prepared in the following way: starting with 0.3 g of the above oil in 1 cm$^3$ of acetone, 0.24 g of oxalic acid dissolved in 1 cm$^3$ of acetone is added. After precipitation of the salt, the medium is diluted with 5 cm$^3$ of acetone and filtered. The crystals are washed with twice 4 cm$^3$ of acetone and then dried in an oven under reduced pressure (10 Pa) at a temperature in the region of 40° C. 0.26 g of (−)-(4R)-4-butyl-4,5-dihydro-1,3-thiazol-2-ylamine oxalate is obtained in the form of a white solid melting at 91° C. ($\alpha_D^{20}$=−7 under a 589 nm Na lamp and $\alpha_D^{20}$=−70.1±1.2 under a 365 nm Hg lamp, at a concentration of 0.5% in methanol).

N-(tert-Butyl)-N'-[(1R)-1-butyl-2-hydroxyethyl]thiourea: The process is performed as in Example 2, starting with 1.14 g of (2R)-2-amino-2-butyl-1-ethanol and 1.36 cm$^3$ of tert-butyl isothiocyanate in 15 cm$^3$ of ethanol, with stirring for 18 hours at a temperature in the region of 20° C. and then for 3 hours in the region of 60° C. After concentration of the reaction medium under reduced pressure (5 kPa) at a temperature in the region of 40° C. 2.38 g of N-(tert-butyl)-N'-[(1R)-1-butyl-2-hydroxyethyl]thiourea are obtained in the form of a yellow oil. Infrared spectrum (CH$_2$Cl$_2$):3620; 4430; 4410; 2960; 1560; 1500; 1395; 1375 and 1205 cm$^{-1}$.

(2R)-2-Aminohexanol: 3.7 g of L-norleucine methyl ester hydrochloride are dissolved in 20 cm$^3$ of water. The required amount of aqueous sodium carbonate solution to obtain a pH of 10 is added to this stirred solution at a temperature in the region of 20° C. The medium is extracted with 3 times 50 cm$^3$ of ethyl acetate. The extracts are combined, dried over sodium sulfate, filtered and concentrated under reduced pressure (5 kPa) at a temperature in the region of 50° C. 2.95 g of methyl (2R)-2-amino-2-butylacetate are obtained in the form of a yellow oil. The process is then performed as in Example 2, starting with 2.9 g of methyl (2R)-2-amino-2-butylacetate and 1.14 g of sodium borohydride in 50 cm$^3$ of ethanol. The reaction is carried out at a temperature in the region of −15° C. and the reaction medium is then stirred for 18 hours at a temperature in the region of 20° C., and finally for 1 h 30 min at a temperature in the region of 80° C. After concentration of the reaction mass under reduced pressure (5 kPa) at a temperature in the region of 50° C., the residue obtained is purified by chromatography under a pressure of argon (50 kPa) on a column of silica gel (particle size 40–63μ; diameter 2 cm; height 20 cm), eluting with a mixture of ethyl acetate/methanol (80/20 by volume). The fractions containing the expected product are combined and then concentrated under reduced pressure (5 kPa) at a temperature in the region of 40° C. 1.2 g of (2R)-2-aminohexanol are obtained in the form of an oil which has a tendency to crystallize. ($\alpha_D^{20}$=+2.6±0.4 at a concentration of 0.5% in methanol).

EXAMPLE 15

(+)-(5S)-5-Methyl-4,5-dihydro-1,3-thiazol-2-ylamine hydrochloride

The process is performed as in Example 1, starting with 11.86 g of N-[(2S)-2-hydroxypropyl]-N'-tert-butylthiourea in 168 cm$^3$ of aqueous 6N hydrochloric acid. After heating for 3 hours at a temperature in the region of 100° C. and an identical work-up, 2.30 g of (+)-(5S)-5-methyl-4,5-dihydro-1,3-thiazol-2-ylamine hydrochloride are obtained in the form of a white solid melting at 173° C. ($\alpha_D^{20}$=+73.8±1.4 at a concentration of 0.5% in methanol).

N-[(2S)-2-Hydroxypropyl]-N'-tert-butylthiourea: The process is performed as in Example 1, starting with 5 g of (+)-(S)-1-amino-2-propanol and 8.43 g of tert-butyl isothiocyanate in 60 cm³ of ethanol. After stirring the reaction medium for 5 hours at a temperature in the region of 20° C. and then concentration under reduced pressure (5 kPa) at a temperature in the region of 50° C., the white solid obtained is taken up in diethyl ether. The suspension is again concentrated under the same conditions as above. 11.86 g of N-[(2S)-2-hydroxypropyl]-N'-tert-butylthiourea are obtained in the form of a white solid melting at 106° C.

EXAMPLE 16

(−)-(4S)-4-Cyclohexylmethyl-4,5-dihydro-1,3-thiazol-2-ylamine

The process is performed as in Example 1, starting with 11.1 g of N-(tert-butyl)-N'-[(1S)-1-cyclohexylmethyl-2-hydroxyethyl]thiourea in 110 cm³ of aqueous 6N hydrochloric acid maintained at a temperature in the region of 100° C. for 2 hours. By means of an identical work-up, 3.6 g of (−)-(4S)-4-cyclohexylmethyl-4,5-dihydro-1,3-thiazol-2-ylamine are obtained in the form of a white solid melting at 169° C. ($\alpha_D^{20}$=−33.9±0.8 at a concentration of 0.5% in methanol).

N-(tert-Butyl)-N'-[(1S)-1-cyclohexylmethyl-2-hydroxyethyl]thiourea: The process is performed as in Example 3, starting with 8.1 g of (+)-(2S)-2-amino-3-cyclohexyl-1-propanol and 9.8 cm³ of tert-butyl isothiocyanate in 79 cm³ of ethanol. The reaction medium is stirred for 72 hours at a temperature in the region of 20° C. After concentration of the reaction mass under reduced pressure (5 kPa) at a temperature in the region of 50° C., the oil obtained is taken up in 110 cm³ of cold petroleum ether. The crystals are filtered off and dried under reduced pressure (10 Pa) at a temperature in the region of 60° C. 11.1 g of N-(tert-butyl)-N'-[(1S)-1-cyclohexylmethyl-2-hydroxyethyl]thiourea are obtained in the form of a white solid melting at 97° C.

EXAMPLE 17

(+)-(4R)-4-Cyclohexylmethyl-4,5-dihydro-1,3-thiazol-2-ylamine hydrochloride

The process is performed as in Example 1, starting with 2.9 g of N-(tert-butyl)-N'-[(1R)-1-cyclohexylmethyl-2-hydroxyethyl]thiourea in 28 cm³ of aqueous 6N hydrochloric acid by heating at a temperature in the region of 100° C. for 2 h 15 min. By means of an identical work-up, a solid is obtained which is purified by dissolution in 15 cm³ of water and extraction with 10 cm³ of dichloromethane. The aqueous phase is made alkaline by addition of 10 cm³ of 1N sodium hydroxide and is extracted with twice 15 cm³ of ethyl acetate. The combined organic extracts are concentrated under reduced pressure (5 kPa) at a temperature in the region of 40° C. The resulting paste is taken up in twice 20 cm³ of diethyl ether. The solid is filtered off and dried in an oven under reduced pressure (10 Pa) at a temperature in the region of 60° C. 0.4 g of (+)-(4R)-4-cyclohexylmethyl-4,5-dihydro-1,3-thiazol-2-ylamine hydrochloride is obtained in the form of a white solid melting at 169° C. ($\alpha_D^{20}$=+31.8±0.9 at a concentration of 0.5% in methanol).

N-(tert-Butyl)-N'-[(1R)-1-cyclohexylmethyl-2-hydroxyethyl]thiourea: The process is performed as in Example 3, starting with 4.89 g of (2R)-2-amino-3-cyclohexyl-1-propanol and 5.9 cm³ of tert-butyl isothiocyanate in 48 cm³ of absolute ethanol. After stirring for 5 days at a temperature in the region of 20° C., the reaction medium is concentrated under reduced pressure (5 kPa) at a temperature in the region of 40° C. The solid obtained is taken up in 200 cm³ of petroleum ether and the insoluble material is then filtered off and air-dried. 2.96 g of N-(tert-butyl)-N'-[(1R)]-1-cyclohexylmethyl-2-hydroxyethyl]thiourea are obtained in the form of a white solid. ($R_f$=0.29 in an ethyl acetate/cyclohexane mixture, on a Merck 60F$_{254}{}^R$ silica plate).

(2R)-2-Amino-3-cyclohexyl-1-propanol: The process is performed as in Example 1, starting with 6.2 g of ethyl (2R)-2-amino-3-cyclohexylpropionate and 1.93 g of sodium borohydride in 120 cm³ of absolute ethanol at about 5° C. for 10 minutes. The medium is warmed to room temperature and stirred for a further 3 h 30 minutes. After cooling again to about 5° C. and addition of a further 40.94 g of borohydride, followed by stirring at a temperature in the region of 20° C. for 65 hours, the reaction medium is concentrated under reduced pressure (5 kPa) at a temperature in the region of 40° C. A solid is obtained, which is purified by chromatography under a pressure of argon (100 kPa) on a column of silica gel (particle size 40–63μ; 320 g), eluting with pure methanol. The fractions containing the expected product are collected. These fractions are combined and then concentrated under reduced pressure (5 kPa) at a temperature in the region of 40° C. 5.16 g of (2R)-2-amino-3-cyclohexyl-1-propanol are obtained in the form of a sticky white solid. ($R_f$=0.25 in methanol on a Merck 60F$_{254}{}^R$ silica plate).

Ethyl (2R)-2-amino-3-cyclohexylpropionate: The process is performed as in Example 2, starting with 10 g of β-cyclohexyl-(D)-alanine hydrochloride in 96 cm³ of absolute ethanol, by treating it with a stream of dry hydrogen chloride at a temperature in the region of 0° C. for 20 minutes. After heating to about 80° C. for 4 days, followed by cooling to 0° C., the mixture is again treated with a stream of hydrogen chloride for 20 minutes, followed by heating to a temperature in the region of 80° C. for 20 hours. The reaction medium is concentrated under reduced pressure (5 kPa) at a temperature in the region of 40° C., and the residue obtained is dissolved in 200 cm³ of water, made alkaline by addition of 19 g of solid potassium carbonate. After evaporation, the resulting solid is taken up in 200 cm³ of ethanol at a temperature in the region of 80° C. The insoluble material is filtered off and the filtrate is evaporated under reduced pressure (5 kPa) at a temperature in the region of 40° C. The residue obtained is taken up in 130 cm³ of ethanol at room temperature. The insoluble material is filtered off and the filtrate is again evaporated under the same conditions as above. 4.8 g of ethyl (2R)-2-amino-3-cyclohexylpropionate are obtained in the form of a whitish paste. ($R_f$=0.80 in a 90/10 by volume mixture of ethanol/aqueous ammonia, on a Merck 60F$_{254}{}^R$ silica plate).

EXAMPLE 18

4-(3-Nitrophenyl)-4,5-dihydro-1,3-thiazol-2-ylamine

The process is performed as in Example 2, starting with 1.49 g of N-(tert-butyl)-N'-[2-hydroxy-1-(3-nitrophenyl) ethyl]thiourea in 14 cm³ of aqueous 6 N hydrochloric acid by heating to a temperature in the region of 100° C. for 2 h 30 min. By means of an identical work-up, 1.01 g of 4-(3-nitrophenyl)-4,5-dihydro-1,3-thiazol-2-ylamine are obtained in the form of a cream-colored solid melting at 232° C.

EXAMPLE 19

(+)-(4R)-4-(4-Pyridylmethyl)-4,5-dihydro-1,3-thiazol-2-ylamine dihydrochloride

The process is performed under the conditions of Example 1 starting with 0.46 g of N-(tert-butyl)-N'-[(1R)-2-hydroxy-1-(4-pyridylmethyl)ethyl]thiourea which is heated in 5 cm³ of aqueous 5 N hydrochloric acid for 16 hours at a temperature in the region of 100° C. After concentration of the reaction mass under reduced pressure (5 kPa) at a temperature in the region of 40° C., an oil is obtained which is taken up in 3 cm³ of 2-propanol. The resulting crystalline precipitate is spin-filtered, washed with 2-propanol and air-dried. 0.1 g of (+)-(4R)-4-(4-pyridylmethyl)-4,5-dihydro-1,3-thiazol-2-ylamine dihydrochloride is obtained in the form of an orange-colored solid melting at 150° C. ($\alpha_D^{20}$=+38.3±0.9 at a concentration of 0.5% in MeOH).

N-(tert-Butyl)-N'-[(1R)-2-hydroxy-1-(4-pyridylmethyl) ethyl]thiourea: A solution of 0.1 g of tert-butyl (1R)-1-(4-pyridylmethyl)-2-hydroxyethyl-carbamate in 3 cm³ of 4 N hydrochloric dioxane is stirred for 16 hours at a temperature in the region of 20° C. The reaction mass is concentrated under reduced pressure (5 kPa) at a temperature in the region of 40° C. 0.075 g of a white product is obtained, and is dissolved in 4 cm³ of ethanol. After addition of 0.08 cm³ of triethylamine and then 0.09 cm³ of tert-butyl isothiocyanate, the mixture is stirred for 16 hours at a temperature in the region of 20° C. and then for 6 hours at a temperature in the region of 50° C. The mixture is evaporated under reduced pressure (5 kPa) at a temperature in the region of 40° C. and the residue obtained is then triturated from 20 cm³ of water. The water is separated out after settling has taken place, ethanol is added to the resulting oil and the solution is then concentrated under the above conditions. 0.10 g of N-(tert-butyl)-N'-[(1R)-2-hydroxy-1-(4-pyridylmethyl)ethyl] thiourea is obtained in the form of an orange-colored oil. ($R_f$=0.50 in a 4/1/1 by volume mixture of ethyl acetate/acetic acid/water, on a Merck 60F$_{254}$$^R$ silica plate).

Tert-Butyl (1R)-1-(4-pyridylmethyl)-2-hydroxyethylcarbamate: 0.52 cm³ of triethylamine is added to a stirred mixture of 1 g of Boc-D-4-pyridylalanine in 10 cm³ of tetrahydrofuran, under an inert atmosphere, and the mixture is then cooled to a temperature in the region of –18° C. After addition of 0.47 cm³ of isobutyl chloroformate, stirring is continued for 30 minutes at a temperature of between –18° C. and –10° C. The mixture is rapidly filtered, followed by addition to the filtrate of 0.28 g of sodium borohydride predissolved in 2 cm³ of water. The mixture is stirred for 1 hour at a temperature in the region of 0° C. and then for 16 hours at a temperature in the region of 20° C. The mixture is made alkaline by addition of aqueous potassium carbonate solution and then stirred in the presence of ethyl acetate. The organic phase is separated out after settling has taken place and then washed with water, dried over magnesium sulfate, filtered and concentrated under reduced pressure (5 kPa) at a temperature in the region of 40° C. The residue obtained is purified by chromatography under an argon pressure of 50 kPa on a column of silica gel (particle size 40–63μ: diameter 2.2 cm; height of silica 30 cm), eluting first with ethyl acetate alone and collecting 30-cm³ fractions. Fractions 1 to 18 are discarded and the column is then eluted with a mixture of ethyl acetate/methanol (90/10 by volume). Fractions 23 to 26 are collected and then combined. After concentration under reduced pressure (5 kPa) at a temperature in the region of 40° C., 0.10 g of tert-butyl (1R)-1-(4-pyridylmethyl)-2-hydroxyethylcarbamate is obtained in the form of an oil. Infrared spectrum (CH$_2$Cl$_2$): 3618; 3434; 2981; 1708; 1501; 1367; 1168 and 1057 cm$^{-1}$.

EXAMPLE 20

(+)-(4R,5R)-5-Methyl-(4R,5R)-4-(4-pyridylmethyl)-4,5-dihydrothiazol-2-ylamine dihydrochloride A suspension of 1.96 g of N-tert-butyl-N'-[1R,2RS)-1-(4-pyridylmethyl)-2-hydroxypropyl]-thiourea in 25 cm³ of 5N hydrochloric acid is heated at a temperature in the region of 100° C. for 18 hours. The reaction medium is concentrated under reduced pressure (2 kPa) at a temperature in the region of 40° C. The residue obtained is purified by chromatography on a Chiralcel OD 20μ column in a heptane/isopropanol/triethylamine mixture (90/10/0.1 by volume). The fractions containing the expected product are concentrated under reduced pressure (1 kPa) at a temperature in the region of 40° C. The residue obtained is purified by chromatography at atmospheric pressure on a column of silica gel (particle size 40–60 μm; diameter 1.2 cm; height 30 cm), eluting with a mixture of ethyl acetate/acetic acid/water (2/1/1 by volume). The fractions containing the expected product are combined and concentrated under reduced pressure (2 kPa) at a temperature in the region of 40° C. The residue obtained is taken up in 5 cm³ of 5N hydrochloric acid and ethanol and is then concentrated under reduced pressure (2 kPa) at a temperature in the region of 40° C. After drying in a desiccator under reduced pressure (0.1 kPa) at a temperature in the region of 40° C., 0.4 g of (+)-(4R,5R)-4-(4-pyridylmethyl)-5-methyl-4,5-dihydrothiazol-2-ylamine dihydrochloride is obtained in the form of a highly hygroscopic foam [$^1$H NMR spectrum (300 MHz, (CD$_3$)$_2$SO-d$_6$, δ in ppm): 1.44 (d, J=7 Hz: 3H); 3.22 (dd, J=13.5 and 7.5 Hz: 1H); 3.32 (dd, J=13.5 and 5 Hz: 1H); 3.90 (mt: 1H); 4.37 (mt: 1H); 8.01 (broad d, J=6 Hz: 2H); 8.88 (broad d, J=6 Hz: 2H); 9.34 (broad s: 1H); 9.85 (broad s: 1H); 10.31 (unresolved complex: 1H); ($a_D^{20}$=+75.3+/–1.3 in 0.5% methanol).

N'-tert-Butyl-N'[(1R,2RS)-1(4-pyridylmethyl)-2-hydroxypropyl]thiourea: a solution of 1.41 g of (3R,2RS)-3-amino-4-(4-pyridinyl)-2-butanol in 30 cm³ of ethanol, to which are added 1.08 cm³ of tert-butyl isothiocyanate and then 2.16 cm³ of triethylamine, is heated for 16 hours with stirring at a temperature in the region of 50° C. The reaction medium is concentrated under reduced pressure (2 kPa) at a temperature in the region of 40° C., taken up in 10 cm³ of water, washed with twice 30 cm³ of dichloromethane, dried over magnesium sulfate, filtered, evaporated under the above conditions and then dried in a desiccator under reduced pressure (0.1 kPa) at a temperature in the region of 40° C. 2 g of N'-tert-butyl-N'-[(1R,2RS)-1-(4-pyridylmethyl)-2-hydroxypropyl]thiourea are obtained in the form of an orange-colored oil [$^1$H NMR spectrum (300 MHz, (CD$_3$)$_2$SO-d$_6$, δ in ppm). We observe a mixture of two diastereoisomers A and B in respective proportions of 70/30, δ=0.99 (d, J=6.5 Hz: 0.9H); 1.09 (d, J=6.5 Hz: 2.1H); 1.37 (s: 6.3H); 1.41 (s: 2.7H); 2.74 (dd, J=14.5 and 9 Hz: 0.7H); from 2.75 to 2.90 (mt: 0.6H); 2.93 (dd, J=14.5 and 5 Hz: 0.7H); from 3.55 to 3.80 (mt: 1H); from 4.35 to 4.60 (unresolved complex: 1H; 4.65 (unresolved complex: 0.3H); 4.88 (unresolved complex: 0.7H); from 7.10 to 7.25 (mt: 1H); 7.17 (broad s: 0.7H); 7.27 (broad d, J=6 Hz: 1.4H); 7.31 (broad d, J=6 Hz: 0.6H); 7.44 (broad s: 0.3H); from 8.35 to 8.50 (mt: 2H).

(3R,2RS)-3-Amino-4-(4-pyridyl)-2-butanol dihydrochloride: a solution of 20 cm³ of 4N hydrochloric acid in dioxane is added with stirring, at a temperature in the region of 20° C., to a solution of 1.85 g of tert-butyl N-[(1R,2RS)-1-(4-pyridylmethyl)-2-hydroxypropyl]carbamate. The mixture is stirred at a temperature in the region of 20° C. for 5 hours and is then concentrated under reduced pressure (2 kPa) at a temperature in the region of 40° C. 1.8 g of (3R,2RS)-3-amino-4-(4-pyridyl)-2-butanol dihydrochloride are obtained in the form of a yellow solid [¹H NMR spectrum (300 MHz, $(CD_3)_2SO$-$d_6$ with addition of a few drops of $CD_3COOD$-$d_4$, δ in ppm). We observe a mixture of two diastereoisomers A and B in respective proportions of 70/30; δ=1.18 and 1.20 (2 d, J=6.5 Hz: 3H in total); 3.13 (dd, J=10.5 and 6 Hz: 0.7H); from 3.20 to 3.35 (mt: 1.3H); from 3.45 to 3.65 (mt: 0.6H); 3.72 (mt: 0.7H); 3.96 (mt: 0.7H); from 8.05 to 8.15 (mt: 2H); 8.88 (broad d, J=6 Hz: 2H)].

Tert-Butyl N-[(1R,2RS)-1-(4-pyridylmethyl)-2-hydroxypropyl]carbamate: 0.43 g of sodium borohydride is added, with stirring and at a temperature in the region of 10° C., to a solution of 2 g of tert-butyl N-[(1R)-1-(4-pyridylmethyl-2-oxopropyl]carbamate and the mixture is then stirred at a temperature in the region of 20° C. for 18 hours. The reaction medium is concentrated under reduced pressure (1 kPa) at a temperature in the region of 40° C., taken up in 50 cm³ of water, extracted with 100 cm³ of ethyl acetate, dried over magnesium sulfate, filtered and concentrated under reduced pressure (1 kPa) at a temperature in the region of 40° C. 1.83 g of tert-butyl N-[(1R,2RS)-1-(4-pyridylmethyl)-2-hydroxy-propyl]carbamate are obtained in the form of a yellow solid [¹H NMR spectrum (300 MHz, $(CD_3)_2SO$-$d_6$, δ in ppm). We observe a mixture of two diastereoisomers A and B in respective proportions of 70/30; δ=1.03 (d, J=6.5 Hz: 0.9H); 1.09 (d, J=6.5 Hz: 2.1H); 1.28 (s:2.7H); 1.30 (s, 6.3H); from 2.45 to 2.55 (mt: 0.7H); 2.61 (dd, J=13.5 and 10.5 Hz: 0.3H); 2.81 (dd, J=13.5 and 4 Hz 0.3H); 3.01 (dd, J=13.5 and 2 Hz: 0.7H); from 3.40 to 3.70 (mt: 2H); 4.70 (d, J =5.5 Hz: 0.3H); 4.78 (d, J=5.5 Hz: 0.7H); 6.53 (d, J =9 Hz: 0.3H); 6.67 (d, J=9 Hz: 0.7H); 7.20 (broad d, J=6 Hz: 1.4H); 7.25 (broad, J=6 Hz: 0.6H); from 8.40 to 8.50 (mt: 2H)].

Tert-Butyl N-[(1R)-1-(4-pyridylmethyl)-2-oxopropyl] carbamate: a mixture, under an inert atmosphere, of 5.3 g of N-{2-[N-methoxy-N-(methyl)-amino]-2-oxo-(1R)-1-(4-pyridylmethyl)ethyl}carbamate in 120 cm³ of tetrahydrofuran is cooled to a temperature in the region on 0° C. 17 cm³ of a 3M solution of methylmagnesium bromide in diethyl ether are then added over 1 hour and the mixture is stirred for 1 hour at 0° C. and for 18 hours at a temperature in the region of 20° C. The reaction medium is cooled again to a temperature in the region of 0° C., followed by dropwise addition of 30 cm³ of 1N hydrochloric acid and 100 cm³ of water, the resulting mixture is extracted with ethyl acetate and the extracts are washed with twice 100 cm³ of water. The combined organic phases are dried over sodium sulfate, filtered and then concentrated under reduced pressure (2 kPa) at a temperature in the region of 40° C. The residue obtained is purified by chromatography at atmospheric pressure on a column of silica gel (particle size 60–200 μm; diameter 4 cm; height 35 cm), eluting with ethyl acetate. The fractions containing the expected product are combined and concentrated under reduced pressure (2 kPa) at a temperature in the region of 40° C. 0.2 g of tert-butyl N-[(1R,2RS)-1-(4-pyridylmethyl)-2-oxopropyl]carbamate is obtained [¹H NMR spectrum (300 MHz, $(CD_3)_2SO$-$d_6$, δ in ppm): 1.34 (s: 9H); 2.16 (s: 3H); 2.71 (dd, J=14 and 10,5 Hz: 1H); 3.08 (dd, J=14 and 4.5 Hz); 4.21 (mt: 1H); 7.27 (broad d, J=5.5 Hz: 2H); 7.34 (d, J=8 Hz: 1H); 8.47 (broad d, J=5.5 Hz: 2H)].

Tert-Butyl N-{2-[N-methoxy-N-(methyl)amino]-2-oxo-(1R)-1-(4-pyridylmethyl)ethyl}carbamate: a solution, under an inert atmosphere, of 20 g of D-N-Boc-pyridylalanine and 16.5 cm³ of N-methylmorpholine in 500 cm³ of dichloromethane is cooled to a temperature in the region of −15° C. 9.75 cm³ of isobutyl chloroformate are then added and the mixture is stirred for 15 minutes at this temperature. After addition of 7.61 g of N,O-dimethylhydroxylamine hydrochloride, stirring is continued for 1 hour at a temperature in the region of −15° C. and then for 18 hours at room temperature. 250 cm³ of water are added to the reaction medium, followed by extraction with 100 cm³ of dichloromethane. The organic phase is dried over sodium sulfate, filtered and concentrated under reduced pressure (2 kPa) at a temperature in the region of 50° C. The residue is purified on a column of silica gel (particle size 60–200 μm; height 35 cm), eluting with ethyl acetate. The fractions containing the expected product are combined and concentrated under reduced pressure (2 kPa) at a temperature in the region of 40° C. 6.5 g of tert-butyl N-{2-[N-methoxy-N-(methyl)-amino]-2-oxo-(1R)-1-(4-pyridylmethyl)ethyl}carbamate are obtained in the form of a thick yellow oil [¹H NMR spectrum (300 MHz, $(CD_3)_2SO$-$d_6$, δ in ppm): 1.33 (s: 9H); 2.78 (dd, J=13.5 and 10 Hz: 1H); 2.89 (dd, J=13.5 and 4.5 Hz: 1H); 3.14 (broad s: 3H); 3.76 (broad s: 3H); 4.63 (mt: 1H); 7.24 (mt: 1H); 7.27 (broad d, J=5.5 Hz: 2H); 8.48 (broad d, J=5.5 Hz: 2H)].

EXAMPLES 21 and 22

(+)-4-(5-Thiazolylmethyl)4,5-dihydrothiazol-2-ylamine dihydrochloride and (−)-4-(5-thiazolylmethyl)4,5-dihydrothiazol-2-ylamine dihydrochloride A racemic mixture of 0.38 g of (4RS)-4-(5-thiazolylmethyl)-4,5-dihydrothiazol-2-ylamine dihydrochloride is separated on a Chiralcel OD 10μ column in a mixture of heptane/2-isopropanol/triethylamine (80/20/0.1 by volume). The fractions containing the expected product are concentrated under reduced pressure (1 kPa) at a temperature in the region of 40° C. to give 0.053 g of (+)-4-(5-thiazolylmethyl)4,5-dihydrothiazol-2-ylamine dihydrochloride and 0.057 g of (−)-4-(5 thiazolylmethyl)4,5-dihydrothiazol-2-ylamine dihydrochloride.

(+)-4-(5-Thiazolylmethyl)4,5-dihydro-thiazol-2-ylamine dihydrochloride: ¹H NMR spectrum (300 MHz, $(CD_3)_2SO$-$d_6$, δ in ppm): from 3.20 to 3.40 (mt: 3H); 3.70 (dd, J=11.5 and 8 Hz: 1H); 4.58 (mt: 1H); 7.85 (s: 1H); 9.10 (s: 1H); 9.26 (unresolved complex: 1H); 9.67 (unresolved complex: 1H); 10.13 (broad s: 1H).

(−)-4-(5-Thiazolylmethyl)4,5-dihydro-thiazol-2-ylamine dihydrochloride: ¹H NMR spectrum (300 MHz, $(CD_3)_2SO$-$d_6$, δ in ppm): from 3.20 to 3.40 (mt: 3H); 3.70 (dd, J=12 and 8 Hz: 1H); 4.58 (mt: 1H); 7.85 (s: 1H); 9.10 (s: 1H); 9.26 (unresolved complex: 1H); 9.67 (unresolved complex: 1H); 10.14 (broad s, 1H); $\alpha_D^{20}$=−4.2+/−0.6 at a concentration of 0.5% in methanol).

(4RS)-4-(5-Thiazolylmethyl)-4,5-dihydro-thiazol-2-ylamine dihydrochloride: a solution of 0.56 g of N-(tert-butyl)-N'-[(1RS)-1-hydroxymethyl-2-(5-thiazolyl)ethyl]thiourea in 5.5 cm³ of 6N hydrochloric acid is heated at a temperature in the region of 110° C. for 3 hours. The reaction medium is concentrated under reduced pressure (1 kPa) at a temperature in the region of 60° C., taken up in 4 cm³ of ethanol and 6 cm³ of diethyl ether and evaporated under the same conditions as above. The residue is taken up in 6 cm³ of ethanol and filtered, and the solid is dried in a desiccator under reduced pressure (0.1 kPa) at a temperature in the region of 40° C. and then dissolved in 5.5 cm³ of 6N hydrochloric acid solution and refluxed at a temperature in the region of 110° C. for 9 hours. The reaction medium is concentrated under reduced pressure (1 kPa) at a temperature in the region of 40° C. and dried in a desiccator under reduced pressure (0.1 kPa) at a temperature in the region of 40° C., to give 0.54 g of (4RS)-4-(5-thiazolylmethyl)-4,5-dihydro-thiazol-2-ylamine dihydrochloride in the form of a pasty solid [¹HNMR spectrum (300 MHz, (CD$_3$)$_2$SO-d$_6$, δ in ppm): from 3.20 to 3.40 (mt: 3H); from 3.60 to 3.80 (mt: 1H); 4.57 (mt: 1H); 7.85 (s, 1H); 9.10 (s: 1H); 9.26 (unresolved complex: 1H); 9.66 (unresolved complex: 1H); 10.13 (broad s: 1H].

N-(tert-Butyl)-N'-[(1RS)-1-hydroxymethyl-2-(5-thiazolyl)ethyl]thiourea: 0.52 cm³ of triethylamine is added to a solution of 0.56 g of (2RS)-2-amino-3-(5-thiazolyl)-1-propanol hydrochloride in 8 cm³ of ethanol, followed by addition of 0.55 cm³ of tert-butyl isothiocyanate. The mixture is stirred at a temperature in the region of 20° C. for 18 hours and is then heated at a temperature in the region of 60° C. for 1 hour 30 minutes. After cooling, the reaction medium is concentrated under reduced pressure (1 kPa) at a temperature in the region of 40° C., taken up in 6 cm³ of water and washed with 3 times 20 cm³ of dichloromethane, dried over magnesium sulfate, filtered, evaporated under the above conditions and then dried in a desiccator under reduced pressure (0.1 kPa) at a temperature in the region of 40° C. 0.56 g of N'-(tert-butyl-N[prime]-[(1RS)-1-hydroxymethyl-2-(5-thiazolyl)ethyl]-thiourea is obtained in the form of a viscous yellow oil [¹H NMR spectrum (300 MHz, (CD$_3$)$_2$SO-d$_6$, δ in ppm): 1.43 (s: 9H); 3.03 (dd, J=15 and 7 Hz: 1H); 3.19 (dd, J=15 and 7 Hz: 1H); from 3.30 to 3.50 (mt: 2H); 4.41 (mt: 1H); 4.97 (t, J=5 Hz: 1H); 7.23 (d, J=8 Hz: 1H); 7.30 (broad s: 1H); 7,67 (s: 1H); 8.94 (s: 1H)].

(2RS)-2-Amino-3-(5-thiazolyl)-1-propanol hydrochloride: a solution of 0.63 g of N-[(1RS)-1-hydroxymethyl-2-(5-thiazolyl)ethyl]acetamide in 7.86 cm³ of 6N hydrochloric acid is heated to a temperature in the region of 110° C. for 3 hours. The reaction mixture is filtered, concentrated under reduced pressure (1 kPa) at a temperature in the region of 40° C., taken up in isopropyl ether, concentrated under the above conditions, taken up in 10 cm³ of isopropyl ether, filtered and dried in a desiccator under reduced pressure (0.1 kPa) at a temperature in the region of 40° C. 0.56 g of (2RS)-2-amino-3-(5-thiazolyl)-1-propanol hydrochloride is obtained in the form of a beige-colored solid melting at 192° C. [¹H NMR spectrum (300 MHz, (CD$_3$)$_2$SO-d$_6$, δ in ppm): 3.21 (d, J=7 Hz: 2H); 3.35 (mt: 1H); 3.48 (dd, J=11.5 and 5.5 Hz: 1H); 3.61 (dd, J=11.5 and 4 Hz: 1H); 7.83 (broad s: 1H); 8.19 (unresolved complex: 3H); 9.10 (broad s: 1H)].

N-[(1RS)-1-Hydroxymethyl-2-(5-thiazolyl)-ethyl] acetamide: 0.4 g of sodium borohydride is added to a solution of 1.2 g of ethyl (2RS)-2-acetylamino-3-(5-thiazolyl)propanoate in 20 cm³ of ethanol, followed by stirring under an inert atmosphere at a temperature in the region of 20° C. After 18 hours, a further 0.1 g of sodium borohydride is added and the mixture is then stirred for 24 hours at a temperature in the region of 20° C. The reaction medium is concentrated under reduced pressure (1 kPa) at a temperature in the region of 40° C. The residue is taken up in 10 cm³ of water and extracted with 3 times 30 cm³ of ethyl acetate. The organic phase is dried over magnesium sulfate, filtered and concentrated under reduced pressure (1 kPa) at a temperature in the region of 40° C. The residue is chromatographed under an argon pressure of 60 kPa on a column of silica gel (particle size 40–63μ; diameter 3.5 cm; height 31 cm), eluting with 100 cm³ of dichloromethane, 600 cm³ of a dichloromethane/methanol mixture (98/2 by volume), 500 cm³ of a dichloromethane/methanol mixture (96/4 by volume) and 1 dm³ of a dichloromethane/methanol mixture (90/10 by volume). The fractions containing the expected product are combined and then concentrated under the above conditions. 0.63 g of N-[(1RS)-1-hydroxymethyl-2-(5-thiazolyl)-ethyl]acetamide is obtained in the form of a yellow oil [¹H NMR spectrum (300 MHz, (CD$_3$)$_2$SO-d$_6$, δ in ppm): 1.80 (s: 3H); 2.85 (dd, J=15 and 9 Hz: 1H); 3.16 (dd, J=15 and 5 Hz: 1H); from 3.25 to 3.45 (mt: 2H); 3.87 (mt: 1H); 4.85 (mt: 1H); 7.65 (S: 1H); 7.79 (d, J=8.5 Hz: 1H); 8.91 (s: 1H)].

Ethyl (2RS)-2-acetylamino-3-(5-thiazolyl)-propanoate: 2.7 cm³ of 6N sodium hydroxide are added dropwise to a solution of 3.3 g of diethyl 2-acetyl-amino-2-(5-thiazolylmethyl)malonate in 70 cm³ of ethanol. The mixture is stirred for 5 hours, followed by dropwise addition of 1.5 cm³ of 12N hydrochloric acid; a precipitate forms. The product is concentrated under reduced pressure (1 kPa) at a temperature in the region of 40° C. to give a brown solid which is dried for 12 hours in a desiccator under reduced pressure (0.1 kPa) at a temperature in the region of 40° C. This residue is taken up in 50 cm³ of dioxane and then heated at a temperature in the region of 100° C. for 3 hours 30 minutes. The reaction medium is evaporated under reduced pressure (1 kPa) at a temperature in the region of 40° C. The residue is chromatographed under an argon pressure of 60 kPa on a column of silica gel (particle size 40–63μ; diameter 3.5 cm; height 31 cm), eluting with 675 cm³ of dichloromethane, 500 cm³ of a dichloromethane/methanol mixture (99/1 by volume), 500 cm³ of a dichloromethane/methanol mixture (98/02 by volume), 500 cm³ of a dichloromethane/methanol mixture (97/3 by volume), 500 cm³ of a dichloromethane/methanol mixture (95/5 by volume), 500 cm³ of a dichloromethane/methanol/aqueous ammonia mixture (12/1.5/0.5 by volume) and 500 cm³ of a dichloromethane/methanol/aqueous ammonia mixture (12/3/0.5 by volume). The fractions containing the expected product are combined and then concentrated under the above conditions. 0.8 g of ethyl (2RS)-2-acetylamino-3-(5-thiazolyl)propanoate is obtained in the form of brown oil [Mass spectrum: DCI m/z=243 MH⁺].

Diethyl 2-acetylamino-2-(5-thiazolylmethyl)-malonate: after dissolving 1.24 g of sodium in 20 cm³ of ethanol, 10.86 cm³ of diethyl acetamidomalonate are added, followed by heating at a temperature in the region of 75° C. After 15 minutes, a solution of 5-chloromethylthiazole in 20 cm³ of ethanol is added, followed by heating for 2 hours at a temperature in the region of 75° C. The reaction medium is evaporated under reduced pressure (1 kPa) at a temperature in the region of 40° C. The residue is chromatographed under an argon pressure of 60 kPa on a column of silica gel (particle size 60–200μ; diameter 6.5 cm; height 40 cm), eluting with a dichloromethane/methanol mixture (99/1 by volume), a dichloromethane/methanol mixture (98/02 by volume) and then a dichloromethane/methanol mixture (95/5 by volume). The fractions containing the expected product are combined and then concentrated under the above conditions. 3.3 g of diethyl 2-acetylamino-2-(5-thiazolylmethyl)malonate are obtained in the form of an orange-colored solid [¹H NMR spectrum (300 MHz, (CD$_3$)$_2$SO-d$_6$, δ in ppm): 1.18 (t, J=7.5 Hz: 6H); 2.00 (s: 3H); 3.75 (s: 2H); 4.17 (q, J=7.5 Hz: 4H); 7.61 (s: 1H); 8.37 (broad s: 1H); 9.00 (s: 1H)].

5-Chloromethylthiazole: 11 g of N-chloro-succinimide are added to a solution of 8.2 g of 5-methylthiazole in 250 cm³ of carbon tetrachloride, followed by addition of 0.1 g of benzoyl peroxide. The mixture is heated for 20 hours at a temperature in the region of 80° C. and is then exposed to UV for 5 hours. The reaction mixture is cooled, filtered and concentrated under reduced pressure (1 kPa) at a temperature in the region of 20° C. 6.4 g of 5-chloro-methylthiazole are obtained [Mass spectrum: DCI m/z=134 MH$^+$].

EXAMPLE 23

(+)-(4R)-4-(2-Pyrazinylmethyl)-4,5-dihydro-2-thiazolyl-amine dihydrochloride A racemic mixture of 2.9 g of (4RS)-4-(2-pyrazinylmethyl)-4,5-dihydro-2-thiazolyl-amine dihydrochloride is separated on a Chiralcel OD10μ column in a heptane/ethanol/triethylamine mixture (80/20/0.1 by volume). The fractions containing the expected product are concentrated under reduced pressure (1 kPa) at a temperature in the region of 40° C. The residue obtained is dissolved in 5 cm³ of ethanol, followed by addition of 6 cm³ of hydrochloric acid dissolved in diethyl ether and 15 cm³ of diethyl ether. After filtration, washing with 15 cm³ of diethyl ether and drying, 0.371 g of (+)-(4R)-4-(2-pyrazinylmethyl)-4,5-dihydro-2-thiazolylamine dihydrochloride is obtained in the form of a beige-colored solid melting at 154° C. [$^1$H NMR spectrum (300 MHz, (CD$_3$)$_2$SO-d$_6$, δ in ppm): 3.22 (d, J=6.5 Hz: 2H); 3.45 (dd, J=11.5 and 5.5 Hz: 1H); 3.75 (dd, J=11.5 and 8 Hz: 1H); 4.73 (mt: 1H); 8.60 (broad d, J=2.5 Hz: 1H); 8.63 (dd, J=2.5 and 1.5 Hz: 1H); 8.66 (broad s; 1H); 9.09 (unresolved complex: 1H); 9.58 (unresolved complex: 1H); 9.95 (broad s: 1H); ($\alpha_D^{20}$=+46.3+/−1.1 at a concentration of 0.5% in methanol)].

(4RS)-4-(2-Pyrazinylmethyl)-4,5-dihydro-2-thiazolylamine dihydrochloride: A solution of 7.2 g of N-(tert-butyl)-N'-[(1RS)-1-hydroxymethyl-2-(2-pyrazinyl)ethyl]thiourea in 20 cm³ of 5N hydrochloric acid is heated at a temperature in the region of 110° C. for 20 hours. The reaction medium is concentrated under reduced pressure (1 kPa) at a temperature in the region of 55° C. and then taken up in ethanol and concentrated under the same conditions as above. The residue is chromatographed at atmospheric pressure on a column of silica gel (particle size 40–60μ; diameter 4 cm; height 30 cm), eluting with an acetic acid/water/ethyl acetate mixture (1/1/4 by volume). The fractions containing the expected product are combined and then concentrated under the above conditions. The oil obtained is taken up in ethanol and the precipitate obtained is filtered off and then dried in a desiccator under reduced pressure (0.1 kPa) at a temperature in the region of 40° C. to give 2.9 g of (4RS)-4-(2-pyrazinylmethyl)-4,5-dihydro-1,3-thiazol-2-ylamine dihydrochloride in the form of a brown solid melting at 190° C. [$^1$H NMR spectrum (300 MHz, (CD$_3$)$_2$SO-d$_6$, δ in ppm): 3.23 (d, J=6 Hz: 2H); 3.43 (dd, J=11.5 and 5.5 Hz: 1H); 3.72 (dd, J=11.5 and 7.5 Hz: 1H); 4.74 (mt: 1H); 8.59 (broad s: 1H); 8.64 (broad s: 1H); 8.67 (broad s: 1H); 9.29 (unresolved complex: 1H); 9.77 (unresolved complex: 1H); 10.16 (broad s: 1H)].

N-(tert-Butyl)-N'-[(1RS)-1-hydroxymethyl-2-(2-pyrazinyl)ethyl]thiourea: 11.2 cm³ of triethylamine are added with stirring to a solution of 7.91 g of (2RS)-2-amino-3-(2-pyrazinyl)-1-propanol dihydrochloride in 80 cm³ of ethanol, followed by addition of 7.2 cm³ of tert-butyl isothiocyanate. The mixture is heated at a temperature in the region of 50° C. for 18 hours. After cooling, the reaction medium is concentrated under reduced pressure (1 kPa) at a temperature in the region of 40° C., taken up in 100 cm³ of water and extracted with dichloromethane. The organic phases are combined, washed with 50 cm³ of water, dried over magnesium sulfate, filtered and then concentrated under reduced pressure (1 kPa) at a temperature in the region of 40° C. 7.2 g of N-(tert-butyl)-N'-[(1RS)-1-hydroxymethyl-2-(2-pyrazinyl)-ethyl]thiourea are obtained in the form of a colorless paste [mass spectrum: DCI m/z=269 MH$^+$].

(2RS)-2-Amino-3-(2-pyrazinyl)-1-propanol dihydrochloride: A solution of 11 g of N-[(1RS)-1-hydroxymethyl-2-(2-pyrazinyl)ethyl]acetamide in 30 cm³ of 5N hydrochloric acid is heated at a temperature in the region of 115° C. for 18 hours. The reaction mixture is concentrated under reduced pressure (1 kPa) at a temperature in the region of 40° C. 7.9 g of (2RS)-2-amino-3-(2-pyrazinyl)-1-propanol dihydrochloride are obtained in the form of a black paste [mass spectrum: DCI m/z=154 MH$^+$]

N-[(1RS)-1-Hydroxymethyl-2-(2-pyrazinyl)-ethyl] acetamide: 2.8 g of sodium borohydride are added to a solution of 8.5 g of ethyl (2RS)-2-acetylamino-3-(2-pyrazinyl)propanoate in 100 cm³ of ethanol and the mixture is then stirred at a temperature in the region of 20° C. After 18 hours, the reaction medium is taken up in 50 cm³ of water and 100 cm³ of dichloromethane and the aqueous phase is concentrated under reduced pressure (1 kPa) at a temperature in the region of 40° C. 11 g of N-[(1RS)-1-hydroxymethyl-2-(2-pyrazinyl)-ethyl]acetamide are obtained in the form of a brown paste [$^1$H NMR spectrum (300 MHz, (CD$_3$)$_2$SO-d$_6$ with addition of a few drops of CD$_3$COOD-d$_4$ δ in ppm): 1.71 (s: 3H); 2.81 (dd, J=14.5 and 9 Hz: 1H); 3.03 (dd, J=14.5 and 5 Hz: 1H); 3.35 (dd, J=11 and 6 Hz); 3.42 (dd, J=11 and 5 Hz: 1H); 4.11 (mt: 1H); 7.75 (residual d, J=8.5 Hz: 0.5H); 8.45 (d, J=2.5 Hz: 1H); 8.50 (broad s: 1H); 8.53 (mt: 1H)]).

Ethyl (2RS)-2-acetylamino-3-(2-pyrazinyl)-propanoate: 12 cm³ of 6N sodium hydroxide are added dropwise to a solution of 14 g of diethyl 2-acetylamino-2-(2-pyrazinylmethyl)malonate in 240 cm³ of ethanol and the mixture is then stirred at a temperature in the region of 20° C. After 1 hour, the reaction medium is neutralized with 6 cm³ of 12N hydrochloric acid. After stirring for 2 hours at a temperature in the region of 20° C., the reaction medium is filtered and the filtrates are then concentrated under reduced pressure (1 kPa) at a temperature in the region of 40° C. The residue is taken up in 200 cm³ of dioxane, refluxed for 2 hours and concentrated as above. 8.5 g of ethyl (2RS)-2-acetylamino-3-(2-pyrazinyl)propanoate are obtained in the form of a cream-colored solid [$^1$H NMR spectrum (300 MHz, (CD$_3$)$_2$SO-d$_6$ δ in ppm): 1.13 (t, J=7 Hz: 3H); 1.80 (s: 3H); 3.12 (dd, J=14 and 8.5 Hz: 1H); 3.22 (dd, J=14 and 6 Hz: 1H); 4.07 (q, J=7 Hz: 2H); 4.71 (mt: 1H); 8.36 (d, J=8 Hz: 1H); 8.52 (d, J=2.5 Hz: 1H); from 8.55 to 8.65 (mt: 2H]).

Diethyl 2-acetylamino-2-(2-pyrazinylmethyl)-malonate may be prepared according to C. Petermann and J. L. Fauchere; Helv.Chim.Acta (1983), 66(5), 1513–1518.

EXAMPLES 24 AND 25

4-(1-Imidazolylmethyl)-4,5-dihydro-2-thiazolylamine, enantiomer A, and 4-(1-imidazolylmethyl)-4,5-dihydro-2-thiazolylamine, enantiomer B A racemic mixture of 0.75 g of (4RS)-4-(1-imidazolylmethyl)-4,5-dihydroxy-2-thiazolylamine is separated on a Chiralcel OD10μ column in a heptane/2-isopropanol/triethylamine mixture (80/20/0.1 by volume).

The fractions containing the expected product are combined and then concentrated under reduced pressure (1 kPa) at a temperature in the region of 40° C. to give 0.215 g of 4-(1-imidazolyl-methyl)-4,5-dihydro-2-thiazolylamine, enantiomer A and 0.21 g of 4-(1-imidazolylmethyl)-4,5-dihydro-2-thiazolylamine, enantiomer B.

4-(1-Imidazolylmethyl)-4,5-dihydro-2-thiazolylamine, enantiomer A: $^1$H NMR spectrum (300 MHz, CD$_3$)$_2$SO-d$_6$, δ in ppm): 2.93 (dd, J=11 and 7 Hz: 1H); 3.25 (dd, J=11 and 7 Hz: 1H); 4.03 (d, J=6 Hz: 2H); 4.38 (mt: 1H); 6.49 (unresolved complex: 2H); 6.88 (broad s: 1H); 7.20 (broad s: 1H); 7.64 (broad s: 1H).

4-(1-Imidazolylmethyl)-4,5-dihydro-2-thiazolylamine, enantiomer B: $^1$H NMR spectrum (300 MHz, CD$_3$)$_2$SO-d$_6$, δ in ppm): 2.96 (dd, J=11 and 7.5 Hz: 1H); from 3.20 to 3.40 (mt: 1H); 4.05 (d, J=6 Hz: 2H); 4.41 (mt: 1H); 6.88 (broad s: 1H); 7.20 (broad s: 1H); 7.64 (broad s: 1H).

(4RS)-4-(1-Imidazolylmethyl)-4,5-dihydro-2-thiazolylamine: 5 cm$^3$ of 4N hydrochloric acid in dioxane are added to a solution of 1.39 g of tert-butyl N-[(4RS)-4-(1-imidazolylmethyl)-4,5-dihydro-2-thiazolyl]carbamate in 5 cm$^3$ of dioxane, followed by addition of methanol to dissolve the reaction medium. After stirring at a temperature in the region of 20° C. for 48 hours, the reaction medium is concentrated under reduced pressure (1 kPa) at a temperature in the region of 40° C. and washed with isopropyl ether, with ethyl acetate and then with methanol. The suspension obtained is filtered and the filtrate is evaporated as above and then chromatographed on a column of silica gel, eluting with a mixture of dichloromethane/methanol/28% aqueous ammonia (50/5/1 by volume). The fractions containing the expected product are combined and then concentrated under the above conditions to give 0.33 g of (4RS)-4-(1-imidazolylmethyl)-4,5-dihydro-2-thiazolyl-amine in the form of a viscous yellow oil [$^1$H NMR spectrum (300 MHz, CD$_3$)$_2$SO-d$_6$, δ in ppm): 2.93 (mt: 1H); 3.26 (mt: 1H); 4.03 (d, J=6 Hz: 2H); 4.39 (mt: 1H); 6.49 (unresolved complex: 2H); 6.87 (mt: 1H); 7.20 (mt: 1H); 7.63 (broad s: 1H)].

Tert-Butyl N-[(4RS)-4-(1-imidazolylmethyl)-4,5-dihydro-2-thiazolyl]carbamate: 0.21 g of imidazole predissolved in 10 cm$^3$ of dimethylformamide is added to a solution of 0.085 g of sodium hydride in 20 cm$^3$ of dimethylformamide. After the sodium hydride has disappeared, a solution of 1 g of tert-butyl N-[(4RS)-4-(p-toluenesulfonyloxymethyl)-4,5-dihydro-2-thiazolyl]carbamate in 10 cm$^3$ of dimethylformamide is added and the mixture is then stirred at a temperature in the region of 70° C. for 3 hours. The reaction medium is diluted with ethyl acetate, washed with water, dried over magnesium sulfate and then concentrated under reduced pressure (1 kPa) at a temperature in the region of 40° C. The residue obtained is chromatographed on a column of alumina, eluting with ethyl acetate and a mixture of ethyl acetate/methanol (80/20 by volume). The fractions containing the expected product are combined and then concentrated under the above conditions to give 0.25 g of tert-butyl N-[(4RS)-4-(1-imidazolylmethyl)-4,5-dihydro-2-thiazolyl]carbamate in the form of a sticky yellow mass [mass spectrum: DCI m/z=283 MH$^+$ m/z=183 (M-C$_5$H$_7$O$_2$)$^+$].

Tert-Butyl N-[(4RS)-4-(p-toluenesulfonyloxy-methyl)-4,5-dihydro-2-thiazolyl]carbamate: A solution of 0.8 g of tert-butyl N-[(4RS)-4-hydroxymethyl-4,5-dihydro-2-thiazolyl]carbamate, 0.76 g of p-toluenesulfonyl chloride and 0.56 cm$^3$ of triethylamine in 25 cm$^3$ of dichloromethane is stirred for 16 hours at a temperature in the region of 20° C. The solution obtained is concentrated under reduced pressure (1 kPa) at a temperature in the region of 40° C. The evaporation residue obtained is purified by chromatography at atmospheric pressure on a column of silica gel (particle size 60–200μ; diameter 2 cm; height 25 cm ), eluting with a mixture of cyclohexane/ethyl acetate (70/30 by volume) and collecting 30 cm$^3$ fractions. The fractions containing the expected product are combined and then concentrated under the above conditions. 0.8 g of tert-butyl N-[(4RS)-4-(p-toluenesulfonyloxymethyl)-4,5-dihydro-2-thiazolyl] carbamate is obtained in the form of a white solid [$^1$H NMR spectrum (300 MHz, CD$_3$l$_2$, δ in ppm): 1.48 (s: 9H); 2.46 (s: 3H); 3.10 (dd, J=11.5 and 5.5 Hz: 1H); 3.33 (dd, J=11.5 and 8.5 Hz: 1H); 3.97 (dd, J=9.5 and 8 Hz: 1H); 4.06 (dd, J=9.5 and 4.5 Hz: 1H); 4.43 (mt: 1H); 7.36 (d, J=8 Hz: 2H); 7.80 (d, J=8 Hz: 2H); from 8.50 to 9.40 (very broad unresolved complex: 1H)].

Tert-Butyl N-[(4RS)-4-hydroxymethyl-4,5-dihydro-2-thiazolyl]carbamate: 10 cm$^3$ of aqueous 1N sodium hydroxide are added to a solution of 2 g of tert-butyl 2-[(tert-butoxycarbonyl)imino]-(4RS)-4-[(tert-butoxycarbonyl)oxy]methyl-1,3-thiazolidine-3-carboxylate in 20 cm$^3$ of methanol and the mixture is then stirred at a temperature in the region of 20° C. for 4 hours. The reaction mixture is concentrated under reduced pressure (1 kPa) at a temperature in the region of 50° C. The residue obtained is taken up in 30 cm$^3$ of water, filtered and washed with ethyl acetate and then with water. 0.37 g of tert-butyl N-[(4RS)-4-hydroxymethyl-4,5-dihydro-2-thiazolyl]-carbamate is obtained in the form of a white solid [mass spectrum: DCI m/z=233 MH$^+$ m/z=177 (M-C$_4$H$_7$)$^+$].

Tert-Butyl 2-[(tert-butoxycarbonyl)imino]-(4RS)-4-[(tert-butoxycarbonyl)oxy]methyl-1,3-thiazolidine-3-carboxylate: 10.91 g of di-tert-butyl dicarbonate and 2.81 cm$^3$ of triethylamine are added to a solution of 1.98 g of (4RS)-4-hydroxymethyl-4,5-dihydro-2-thiazolylamine in 20 cm$^3$ of dichloromethane, and the mixture is then stirred at a temperature in the region of 20° C. After 4 hours, a further 3 cm$^3$ of triethylamine are added and the mixture is then stirred for 16 hours at a temperature in the region of 20° C. 50 cm$^3$ of water are added to the reaction mixture and the phases are separated after settling has taken place. The organic phase is dried over magnesium sulfate, filtered and concentrated under reduced pressure (1 kPa) at a temperature in the region of 40° C. 7 g of tert-butyl 2-[(tert-butoxycarbonyl)imino]-(4RS)-4-[(tert-butoxycarbonyl)oxy]methyl-1,3-thiazolidine-3-carboxylate are obtained in the form of a white solid [mass spectrum: DCI m/z=433 MH$^+$ m/z=333 (M-C$_5$H$_7$O$_2$)$^+$].

(4RS)-4-Hydroxymethyl-4,5-dihydro-2-thiazolylamine: A solution of 90 g of 1-tert-butyl-3-(2-hydroxy-1-hydroxymethylethyl)thiourea in 500 cm$^3$ of 6N hydrochloric acid is stirred at a temperature in the region of 100° C. After 3 hours, the reaction mixture is cooled to a temperature in the region of 20° C. and is then concentrated under reduced pressure (1 kPa) at a temperature in the region of 50° C. The residue obtained is taken up in 100 cm$^3$ of water, basified with 100 cm$^3$ of 5N sodium hydroxide and then concentrated as above. The oil obtained is stirred for 20 hours at a temperature in the region of 20° C. in 300 cm$^3$ of ethanol, filtered and washed with 5 times 50 cm$^3$ of ethanol and 3 times 100 cm$^3$ of methanol. The various filtrates are combined, evaporated under reduced pressure (1 kPa) at a temperature in the region of 40° C. and then crystallized from 400 cm$^3$ of ethanol to give 31 g of (4RS)-4-hydroxymethyl-4,5-dihydro-2-thiazolylamine in the form of a white solid melting at 122° C. [infrared spectrum (KBr): 3311; 3164; 1648; 1601; 1349; 1051 and 982 cm$^{-1}$].

1-tert-Butyl-3-(2-hydroxy-1-hydroxymethyl-ethyl) thiourea: 30.4 cm³ of tert-butyl isothiocyanate are added to a solution of 14.6 g of 2-amino-1,3-propanediol in 245 cm³ of ethanol, and the mixture is then stirred at a temperature in the region of 20° C. for 94 hours. The reaction medium is concentrated under reduced pressure (5 kPa) at a temperature in the region of 40° C. and the residue is slurried in a mixture of 160 cm³ of petroleum ether and 26 cm³ of ethanol, and the product is filtered off and then dried in a desiccator under reduced pressure (0.1 kPa) at a temperature in the region of 60° C. 30 g of 1-tert-butyl-3-(2-hydroxy-1-hydroxymethylethyl)thiourea are obtained in the form of a white solid [$^1$H NMR spectrum (250 MHz, (CD$_3$)$_2$SO-d$_6$, δ in ppm): 1.42 (s: 9H); 3.38 (mt: 2H); 3.54 (mt: 2H); 4.17 (unresolved complex: 1H); 4.70 (t, J=5 Hz: 2H); 7.08 (d, J=8 Hz: 1H); 7.38 (s: 1H]).

EXAMPLE 26

(+)-(4R)-4-(4-Thiazolylmethyl)-4,5-dihydro-2-thiazolyl-amine dihydrochloride

A solution of 1.75 g of N-(tert-butyl)-N'-[(1R)-1-hydroxymethyl-2-(4-thiazolyl)ethyl]thiourea in 20 cm³ of 6N hydrochloric acid is heated at a temperature in the region of 110° C. for 20 hours. The reaction medium is concentrated under reduced pressure (1 kPa) at a temperature in the region of 60° C., taken up in 5 cm³ of ethanol and then concentrated under the same conditions as above. The residue is taken up in 5 cm³ of ethanol and the product is then filtered off and dried in a desiccator under reduced pressure (0.1 kPa) at a temperature in the region of 40° C. 0.54 g of (+)-(4R)-4-(4-thiazolylmethyl)-4,5-dihydro-2-thiazolylamine dihydrochloride is obtained in the form of a cream-colored solid melting at 195° C. [$^1$H NMR spectrum (300 MHz, (CD$_3$)$_2$SO-d$_6$, δ in ppm): 3.67 (mt: 2H); 3.41 (dd, J=11.5 and 5.5 Hz: 1H); 3.68 (dd, J=11.5 and 8 Hz: 1H); 4.63 (mt: 1H); 7.59 (d, J=2 Hz: 1H); 9.14 (d, J=2 Hz: 1H); 9.18 (unresolved complex: 1H); 9.66 (unresolved complex: 1H); 10.04 (broad s: 1H); ($\alpha_D^{20}$=+24.2+/−0.8 at a concentration of 0.5% in methanol)].

N-(tert-Butyl)-N'-[(1R)-1-hydroxymethyl-2-(4-thiazolyl) ethyl]thiourea: A solution of 2.5 g of tert-butyl N-[(1R)-1-hydroxymethyl-2-(4-thiazolyl)-ethyl]carbamate in 20 cm3 of 6N hydrochloric acid and 20 cm³ of dioxane is stirred at a temperature in the region of 20° C. for 18 hours. The reaction mixture is concentrated under reduced pressure (1 kPa) at a temperature in the region of 40° C. 1.9 g of a white solid are obtained. The solid obtained is taken up in 6 cm³ of absolute ethanol and 2 cm³ of triethylamine are added, followed by addition of 2.1 cm³ of tert-butyl isothiocyanate. The mixture is stirred at a temperature in the region of 50° C. for 20 hours. The reaction medium is concentrated under reduced pressure (1 kPa) at a temperature in the region of 40° C. The residue is taken up in water and the aqueous phase is extracted with dichloromethane. The organic phase is dried over magnesium sulfate, filtered and concentrated under the above conditions. The residue is dried in a desiccator under reduced pressure (0.1 kPa) at a temperature in the region of 40° C. 1.75 g of N-(tert-butyl)-N'-[(1R)-1-hydroxymethyl-2-(4-thiazolyl)ethyl]thiourea are obtained in the form of a yellow solid [$^1$H NMR spectrum (300 MHz, (CD$_3$)$_2$SO-d$_6$, δ in ppm): 1.41 (s: 9H); 2.96 (dd, J=15 and 7 Hz: 1H); 3.05 (dd, J=15 and 7 Hz: 1H); 3.41 (mt: 2H); 4.62 (unresolved complex: 1H); 4.85 (t, J 5 Hz: 1H); 7.21 (d, J=8.5 Hz: 1H); 7.23 (broad s: 1H); 7.37 (d, J 2 Hz: 1H); 9.04 (d, J=2 Hz: 1H)].

Tert-Butyl N-[(1R)-1-hydroxymethyl-2-(4-thiazolyl) ethyl]carbamate: 1.59 cm³ of triethylamine are added with stirring to a solution of 3 g of BOC-D-(4-thiazolyl)alanine in 50 cm³ of tetrahydrofuran. The reaction medium is cooled to a temperature in the region of −18° C., followed by addition, with stirring and under an inert atmosphere, of 1.16 cm³ of isobutyl chloroformate. After stirring for 40 minutes at a temperature in the region of −15° C., the reaction medium is rapidly filtered under cold conditions and a solution of 0.85 g of sodium borohydride predissolved in 6 cm³ of water is then added to the filtrates, at a temperature in the region of −15° C. and with stirring. After stirring for 18 hours at a temperature in the region of 20° C., the reaction medium is diluted with 100 cm³ of water and extracted with ethyl acetate. The organic phase is washed with water, dried over magnesium sulfate, filtered and concentrated under reduced pressure (1 kPa) at a temperature in the region of 50° C. 2.5 g of tert-butyl N-[(1R)-1-hydroxymethyl-2-(4-thiazolyl) ethyl]carbamate are obtained in the form of a colorless oil [infrared spectrum (CCl$_4$): 3442, 3368, 2980, 2932, 2874, 1710, 1501, 1392, 1367, 1243, 1171, 1048 and 875 cm$^{-1}$].

EXAMPLE 27

(+)-(4R)-4-(3-Aminopropyl)-4,5-diydro-2-thiazolylamine dihydrochloride

A solution of 9.6 g of benzyl N-[(4R)-4-(3-tert-butylthioureido)-5-hydroxypentyl]-carbamate in 50 cm³ of 6N hydrochloric acid is heated at a temperature in the region of 110° C. for 18 hours. The reaction medium is concentrated under reduced pressure (1 kPa) at a temperature in the region of 40° C., taken up successively in 30 cm³ of ethanol and 20 cm³ of isopropanol, concentrating under the same conditions as above between each washing. The solid obtained is taken up in ethanol and diethyl ether, filtered off and dried in a desiccator under reduced pressure (0.1 kPa) at a temperature in the region of 40° C. to give 2.8 g of (+)-(4R)-4-(3-aminopropyl)-4,5-diydro-2-thiazolylamine dihydrochloride in the form of a white solid melting at 166° C. [$^1$H NMR spectrum (300 MHz, (CD$_3$)$_2$SO-d$_6$, δ in ppm): from 1.55 to 1.85 (mt: 4H); 2.81 (mt: 2H); 3.25 (dd, J=11 and 6 Hz: 1H); 3.69 (dd, J=11 and 8 Hz: 1H); 4.27 (mt: 1H); 8.16 (unresolved complex: 3H); 9.50 (broad unresolved complex: 2H); from 9.50 to 10.60 (very broad unresolved complex: 1H); ($\alpha_D^{20}$=+7.5+/−0.4 at a concentration of 0.5% in methanol)].

Benzyl N-[(4R)-4-(3-tert-butylthioureido)-5-hydroxypentyl]carbamate: 2.24 g of lithium chloride are added with stirring to a solution of 16 g of ethyl (2R)-5-{[(benzyloxy)carbonyl]amino}-2-(3-tert-butyl-thioureido) pentanoate in 200 cm³ of ethanol and 100 cm³ of tetrahydrofuran. After stirring for 15 minutes at a temperature in the region of 0° C., 2.24 g of sodium borohydride are added. After stirring for 20 hours at a temperature in the region of 20° C., a further 0.5 g of sodium borohydride is added. The reaction medium is filtered and the filtrates are concentrated under reduced pressure (1 kPa) at a temperature in the region of 40° C. The residue is chromatographed at atmospheric pressure on a column of silica gel (particle size 60–200µ; diameter 5.6 cm; height 40 cm), eluting with a mixture of dichloromethane/ethyl acetate (8/2 by volume) and a mixture of dichloromethane/ethyl acetate (6/4 by volume). The fractions containing the expected product are combined and then concentrated under the above conditions. 9.6 g of benzyl N-[(4R)-4-(3-tert-butylthioureido)-5-hydroxypentyl] carbamate are obtained in the form of a yellow oil [$^1$H NMR spectrum (300 MHz, (CD$_3$)$_2$SO-d$_6$, δ in ppm): from 1.30 to 1.60 (mt: 4H); 1.42 (s: 9H); 3.00 (mt: 2H); from 3.25 to 3.40 (mt: 1H); 3.45 (mt: 1H); 4.21 (unresolved complex: 1H);

4.76 (unresolved complex: 1H); 5.02 (s: 2H); 7.09 (d, J=8.5 Hz: 1H); 7.17 (broad s: 1H); 7.27 (t, J 5.5 Hz: 1H); from 7.30 to 7.45 (mt: 5H)].

Ethyl (2R)-5-{[(Benzyloxy)carbonyl]amino}-2-(3-tert-butylthioureido)pentanoate: 7.5 cm³ of tert-butyl isothiocyanate are added to a solution of 13 g of ethyl (2R)-2-amino-5-[(benzyloxy)carbonyl]amino-pentanoate hydrochloride in 200 cm³ of ethanol, and the mixture is then stirred at a temperature in the region of 20° C. After 48 hours, the reaction medium is concentrated under reduced pressure (1 kPa) at a temperature in the region of 40° C. to give 16 g of ethyl (2R)-5-{[(benzyloxy)carbonyl]amino}-2-(3-tert-butyl-thioureido)pentanoate in the form of a colorless oil [mass spectrum: EI m/z=409 M⁺ m/z=232 $(C_{13}H14NO_3)^+$ m/z=142 (232-PhCH)⁺ m/z=91 $(C_7H_7)^+$].

Ethyl (2R)-2-amino-5-[(benzoyloxy)carbonyl]-aminopentanoate hydrochloride: A solution of 12.5 g of (2R)-2-amino-5-[(benzyloxy)carbonyl]aminopentanoic acid hydrochloride in 200 cm³ of ethanol is cooled to a temperature in the region of −20° C. 6.5 cm³ of thionyl chloride are added dropwise and the mixture is then stirred at a temperature in the region of 20° C. for 18 hours. The reaction medium is concentrated under reduced pressure (1 kPa) at a temperature in the region of 40° C. to give 13 g of ethyl (2R)-2-amino-5-[(benzoyloxy)carbonyl]aminopentanoate hydrochloride [mass spectrum: DCI m/z=295 MH⁺].

(2R)-2-Amino-5-[(benzyloxy)carbonyl]amino-pentanoic acid hydrochloride: 30 g of basic copper II carbonate are added to a solution of 15.5 g of D-ornithine hydrochloride in 1 dm³ of water. The mixture is heated at a temperature in the region of 100° C. for 2 hours, filtered while hot and washed with water. The filtrates are cooled to a temperature in the region of 20° C., followed by addition of 14.5 g of magnesium oxide with stirring. The reaction medium is cooled to a temperature in the region of 0° C., followed by addition of 4 times 15.5 cm³ of benzyl chloroformate. After 18 hours at a temperature in the region of 20° C., the mixture is filtered. The solid is washed successively with 3 times 30 cm³ of water and 3 times 30 cm³ of diethyl ether and is then suspended in 500 cm³ of 1N hydrochloric acid with a gentle stream of hydrogen sulfide for 2 hours. The suspension is filtered and the solid is washed with 0.5N hydrochloric acid. The filtrates are brought to pH 4–5 with dilute aqueous ammonia to give a white precipitate. After filtration and drying in a desiccator, 12.5 g of (2R)-2-amino-5-[(benzyloxy)carbonyl]aminopentanoic acid hydrochloride are obtained in the form of a white solid [¹H NMR spectrum (300 MHz, $(CD_3)_2SO-d_6$, δ in ppm): from 1.40 to 1.80 (mt: 4H); 2.99 (mt: 2H); 3.11 (mt: 1H); 5.02 (broad s: 2H); from 7.25 to 7.45 (mt: 6H)].

EXAMPLE 28

(+)-(4R)-4-(4-Hydroxybenzyl)-4,5-dihydro-2-thiazolyl-amine hydrochloride

A solution of 0.2 g of N-(tert-butyl)-N'-[(1R)-1-hydroxymethyl-2-(4-hydroxyphenyl)ethyl]-thiourea in 2.6 cm³ of 6N hydrochloric acid is heated at a temperature in the region of 110° C. for 18 hours. The reaction medium is concentrated under reduced pressure (1 kPa) at a temperature in the region of 55° C. and is then taken up successively in 10 cm³ of isopropyl ether, 10 cm³ of diethyl ether, 10 cm³ of pentane, 10 cm³ of petroleum ether and 10 cm³ of isopropyl ether, concentrating under the same conditions as above between each wash. The solid obtained is dried in a desiccator under reduced pressure (0.1 kPa) at a temperature in the region of 40° C. to give 0.098 g of (+)-(4R)-4-(4-hydroxybenzyl)-4,5-dihydro-2-thiazolyl-amine hydrochloride in the form of an orange-colored solid [¹H NMR spectrum (300 MHz, $(CD_3)_2SO-d_6$, δ in ppm): 2.78 (dd, J=13.5 and 7.5 Hz: 1H); 2.88 (dd, J=13.5 and 5.5 Hz: 1H); 3.26 (dd, J=11.5 and 6 Hz: 1H); 3.55 (dd, J=11.5 and 7.5 Hz: 1H); 4.45 (mt: 1H); 6.74 (d, J=8.5 Hz: 2H); 7.07 (d, J=8.5 Hz: 2H); 9.09 (unresolved complex: 1H); 9.41 (s: 1H); 9.56 (unresolved complex: 1H); 9.97 (broad s: 1H); $(\alpha_D^{20}$=+ 9.5+/−0.5 at a concentration of 0.5% in methanol)].

N-(tert-Butyl)-N'-[(1R)-1-hydroxymethyl-2-(4-hydroxyphenyl)ethyl]thiourea: 0.15 cm³ of triethylamine is added to a solution of 0.2 g of 4-[(2R)-2-amino-3-hydroxypropyl]phenol in 10 cm³ of absolute ethanol, followed by addition of 0.18 cm³ of tert-butyl isothiocyanate. The mixture is stirred at a temperature in the region of 20° C. for 18 hours and is then heated at a temperature in the region of 60° C. for 4 hours. After cooling, the reaction medium is evaporated under reduced pressure (1 kPa) at a temperature in the region of 40° C. and then chromatographed under an argon pressure of 60 kPa on a column of silica gel (particle size 40–63μ; diameter 2.5 cm; height 29 cm), eluting with a mixture of dichloromethane/methanol (98/2 by volume). The fractions containing the expected product are combined and then concentrated under the above conditions. 0.2 g of N-(tert-butyl)-N'-[(1R)-1-hydroxymethyl-2-(4-hydroxyphenyl)ethyl]thiourea is obtained in the form of a colorless viscous oil [¹H NMR spectrum (300 MHz, $(CD_3)_2SO-d_6$, δ in ppm): 1.42 (s: 9H); 2.63 (dd, J=13.5 and 8 Hz: 1H); 2.72 (dd, J=13.5 and 5.5 Hz: 1H); from 3.25 to 3.40 (mt: 2H); 4.29 (unresolved complex: 1H); 4.83 (t, J=4.5 Hz: 1H); 6.67 (d, J=8 Hz: 2H); 7.05 (d, J=8 Hz: 2H); 7.15 (d, J=8 Hz: 1H); 7.26 (broad s: 1H); 9.16 (s: 1H)].

4-[(2R)-2-Amino-3-hydroxypropyl)]phenol: A solution of 2.2 g of tert-butyl N-[(1R)-1-hydroxy-methyl-2-(4-hydroxyphenyl)ethyl]carbamate in 24 cm³ of dichloromethane and 4 cm³ of dioxane is added, with stirring and under an inert atmosphere, at a temperature in the region of 20° C., to a solution of 20.5 cm³ of 4N hydrochloric acid in dioxane. The mixture is heated at a temperature in the region of 60° C. for 18 hours and is then cooled and concentrated under reduced pressure (1 kPa) at a temperature in the region of 60° C. The residue is taken up in 50 cm³ of dichloromethane, filtered, slurried in 20 cm³ of diethyl ether, filtered again, washed with twice 5 cm³ of diethyl ether and then dried in a desiccator under reduced pressure (0.1 kPa) at a temperature in the region of 40° C. 1.4 g of 4-[(2R)-2-amino-3-hydroxy-propyl)]phenol are obtained in the form of a beige-colored solid melting at 156° C. [¹H NMR spectrum (300 MHz, $(CD_3)_2SO-d_6$, δ in ppm): 2.69 (dd, J=13 and 9 Hz: 1H); 2.79 (dd, J=13 and 5.5 Hz: 1H); 3.23 (mt: 1H); from 3.30 to 3.45 (mt: 1H); 3.51 (ddd, J=11.5–5 and 4.5 Hz: 1H); 5.32 (t, J=5 Hz: 1H); 6.73 (d, J=8.5 Hz: 2H); 7.06 (d, J=8.5 Hz: 2H); 7.95 (unresolved complex: 3H); 9.37 (s: 1H)].

Tert-Butyl N-[(1R)-1-hydroxymethyl-2-(4-hydroxyphenyl)ethyl]carbamate: A solution of 29.6 cm³ of lithium aluminum hydride at 1M in tetrahydrofuran is added, with stirring and under an inert atmosphere, at a temperature in the region of 20° C., to a solution of 4.38 g of methyl BOC-D-tyrosinate in 25 cm³ of tetrahydrofuran. After addition of 60 cm³ of tetrahydrofuran, the reaction mixture is heated at a temperature in the region of 70° C. for 3 hours. The reaction mixture is cooled and then concentrated under reduced pressure (1 kPa) at a temperature in the region of 60° C. The evaporation residue is dried in a desiccator under reduced pressure (0.1 kPa) at a temperature in the region of 40° C. and is then chromatographed under an argon pressure of 60 kPa on a column of silica gel (particle size 40–63μ; diameter 7 cm; height 24 cm), eluting with 10 dm$^3$ of a dichloromethane/methanol mixture (98/2 by volume), 2 dm$^3$ of a dichloromethane/methanol mixture (95/5 by volume) and 2 dm$^3$ of a dichloromethane/methanol mixture (90/10 by volume). The fractions containing the expected product are combined and then concentrated under the above conditions. 2.2 g of tert-butyl N-[(1R)-1-hydroxymethyl-2-(4-hydroxyphenyl)ethyl]-carbamate are obtained in the form of a white foam [$^1$H NMR spectrum (400 MHz, (CD$_3$)$_2$SO-d$_6$, δ in ppm): 1.35 (s: 9H); 2.46 (dd, J=14 and 8 Hz: 1H); 2.68 (dd, J=14 and 6 Hz: 1H); from 3.15 to 3.40 (mt: 2H); 3.50 (mt: 1H); 4.61 (mt: 1H); 6.48 (d, J=8.5 Hz: 1H); 6.65 (d, J=8 Hz: 2H); 6.97 (d, J=8 Hz: 2H); 9.11 (broad s: 1H)].

EXAMPLE 29

(+)-4-(4-Pyridylsulphanylmethyl)-4,5-dihydro-2-thiazolylamine

A racemic mixture of 1.75 g of (4RS)-4-(4-pyridylsulphanylmethyl)-4,5-dihydro-2-thiazolylamine dihydrochloride is separated on a Chiralcel OD 10μ column in a heptane/2-isopropanol/triethylamine mixture (80/20/0.1 by volume) to give 0.43 g of (+)-4-(4-pyridylsulphanylmethyl)-4,5-dihydro-2-thiazolylamine [$^1$H NMR spectrum (300 MHz, (CD$_3$)$_2$SO-d$_6$, δ in ppm): 3.12 (dd, J=11 and 6.5 Hz: 1H); 3.20 (d, J=6.5 Hz: 2H); 3.44 (dd, J=11 and 7.5 Hz: 1H); 4.32 (mt: 1H); 6.49 (unresolved complex: 2H); 7.30 (dd, J=5 and 1.5 Hz: 2H); 8.37 (dd, J=5 and 1.5 Hz: 2H), (α$_D^{20}$=+13.3+/−0.6 at a concentration of 0.5% in methanol)].

(4RS)-4-(4-pyridylsulphanylmethyl)-4,5-dihydro-2-thiazolylamine dihydrochloride: 5 cm$^3$ of 4N hydrochloric acid in dioxane are added to a solution of 0.356 g of tert-butyl N-(4RS)-4-(4-pyridylsulphanyl-methyl)-4,5-dihydro-2-thiazolyl]carbamate in 5 cm$^3$ of methanol and 20 cm$^3$ of dioxane, and the mixture is then stirred at a temperature in the region of 20° C. for 18 hours. The reaction medium is concentrated under reduced pressure (5 kPa) at a temperature in the region of 40° C., taken up in diisopropyl ether and then filtered to give 0.287 g of (4RS)-4-(4-pyridylsulphanylmethyl)-4,5-dihydro-2-thiazolylamine dihydrochloride in the form of a cream-colored solid [$^1$H NMR spectrum (300 MHz , (CD$_3$)$_2$SO-d$_6$, δ in ppm): 3.45 (dd, J=11 and 4.5 Hz: 1H); 3.61 (dd, J=14 and 7 Hz: 1H); 3.69 (dd, J=14 and 5.5 Hz: 1H); 3.80 (dd, J=12 and 8 Hz: 1H); 4.59 (mt: 1H); 8.00 (broad d, J=6.5 Hz: 2H); 8.66 (broad d, J=6.5 Hz: 2H); 9.60 (unresolved complex: 1H); 9.81 (unresolved complex: 1H); from 10.00 to 10.50 (broad unresolved complex: 1H).

tert-Butyl N-[(4RS)-4-(4-pyridylsulphanyl-methyl)-4,5-dihydro-2-thiazolyl]carbamate: a suspension of 1.5 g of tert-butyl N-[(4RS)-4-(p-toluenesulfonyl-oxymethyl)-4,5-dihydro-2-thiazolyl]carbamate in 50 cm$^3$ of acetonitrile is heated until the reagent has dissolved and 0.604 g of 4-mercaptopyridine is then added with stirring. After cooling to a temperature in the region of 20° C., 1.07 g of potassium carbonate are added. After stirring for 48 hours at a temperature in the region of 20° C., the reaction mixture is filtered. The filtrate is concentrated under reduced pressure (1 kPa) at a temperature in the region of 50° C. The residue obtained is taken up in ethyl acetate and water and the phases are separated after settling has taken place. The organic phase is washed with sodium chloride solution, dried over magnesium sulfate and chromatographed on a column of alumina, eluting with successive mixtures of ethyl acetate/cyclohexane (50/50 by volume). The fractions containing the expected product are purified by chromatography on a column of silica gel, eluting with ethyl acetate. The fractions containing the expected product are combined and then concentrated under the above conditions. 0.356 g of tert-butyl N-[(4RS)-4-(4-pyridylsulphanylmethyl)-4,5-dihydro-2-thiazolyl]carbamate is obtained in the form of a yellow oil [$^1$H NMR spectrum (300 MHz, (CD$_3$)$_2$SO-d$_6$, δ in ppm): 1.42 (s: 9H); 3.09 (dd, J=11.5 and 6 Hz: 1H); 3.29 (mt: 2H); 3.40 (dd, J=11.5 and 8 Hz: 1H); 4.25 (mt: 1H); 7.35 (dd, J=5 and 1.5 Hz: 2H); 8.40 (dd, J=5 and 1.5 Hz: 2H); from 9.70 to 10.00 (broad unresolved complex: 1H)].

EXAMPLE 30

(4R)-4-(1-Oxy-4-pyridylmethyl)-4,5-dihydro-2-thiazolylamine hydrochloride

A solution of 0.6 g of N-(tert-butyl)-N'-[(1R)-1-hydroxymethyl-2-(1-oxy-4-pyridyl)ethyl]thiourea in 6 cm$^3$ of 6N hydrochloric acid is heated at a temperature in the region of 110° C. for 18 hours. The reaction medium is concentrated under reduced pressure (1 kPa) at a temperature in the region of 55° C., taken up in twice 20 cm$^3$ of ethanol, concentrated under the same conditions as above, taken up in 10 cm$^3$ of ethanol, filtered and dried in a desiccator under reduced pressure (0.1 kPa) at a temperature in the region of 40° C. to give 0.296 g of (4R)-4-(1-oxy-4-pyridylmethyl)-4,5-dihydro-2-thiazolylamine hydrochloride in the form of cream-colored crystals [$^1$H NMR spectrum (300 MHz, (CD$_3$)$_2$SO-d$_6$, δ in ppm): 3.04 (limiting AB: 2H); 3.34 (dd, J=12 and 5.5 Hz: 1H); 3.68 (dd, J=12 and 8 Hz: 1H); 4.63 (mt: 1H); 7.75 (d, J=7 Hz: 2H); 8.65 (d, J=7 Hz: 2H); 9.30 (unresolved complex: 1H); 9.79 (unresolved complex: 1H); 10.30 (broad s: 1H)].

N-(tert-Butyl)-N'-[(1R)-1-hydroxymethyl-2-(1-oxy-4-pyridyl)ethyl]thiourea: 2.6 cm$^3$ of triethylamine are added to a solution of 1.5 g of (2R)-2-amino-3-(1-oxy-4-pyridyl)-1-propanol hydrochloride in 30 cm$^3$ of absolute ethanol, followed by addition of 1.53 cm$^3$ of tert-butyl isothiocyanate. After adding 20 cm$^3$ of methanol, the mixture is stirred at a temperature in the region of 20° C. for 18 hours and is then concentrated under reduced pressure (1 kPa) at a temperature in the region of 40° C. 1 cm$^3$ of triethylamine is added to the evaporation residue taken up in 10 cm$^3$ of methanol, followed by addition of 1.5 cm$^3$ of tert-butyl isothiocyanate. The mixture is stirred at a temperature in the region of 20° C. for 48 hours. The reaction medium is concentrated under reduced pressure (5 kPa) at a temperature in the region of 40° C. and the product is taken up in 25 cm$^3$ of ethyl acetate, filtered off and washed with 10 cm$^3$ of ethyl acetate and 20 cm$^3$ of isopropyl ether. The triethylamine hydrochloride is removed by passage through a column of alumina. 0.6 g of N-(tert-butyl)-N'-[(1R)-1-hydroxy-methyl-2-(1-oxy-4-pyridyl)ethyl]thiourea is obtained in the form of white crystals [R$^f$=0.36 in a dichloromethane/methanol mixture (90/10 by volume) on a Merck 60 F$_{254}$ alumina plate (type E)].

(2R)-2-Amino-3-(1-oxy-4-pyridyl)-1-propanol hydrochloride: a solution of 20 cm$^3$ of 4N hydrochloric acid in dioxane is added with stirring, at a temperature in the region of 20° C., to a solution of 2 g of tert-butyl N-[(1R)-1-hydroxymethyl-2-(1-oxy-4-pyridyl)ethyl]carbamate in 20 cm$^3$ of dioxane. The mixture is stirred at a temperature in the region of 20° C. for 18 hours and is then taken up in 40 cm$^3$ of dioxane, stirred for 30 minutes and filtered. The precipitate is washed with 10 cm³ of dioxane and then with 25 cm³ of isopropyl ether and dried in a desiccator under reduced pressure (0.1 kPa) at a temperature in the region of 40° C. 1.54 g of (2R)-2-amino-3-(1-oxy-4-pyridyl)-1-propanol hydrochloride are obtained in the form of a pale yellow solid [¹H NMR spectrum (300 MHz, (CD₃)₂SO-d₆, δ in ppm): 3.08 (d, J=6 Hz: 2H); from 3.40 to 3.55 (mt: 2H); from 3.55 to 3.70 (mt: 1H); 7.78 (d, J=6.5 Hz: 2H); 8.26 (broad s: 3H); 8.71 (d, J=6.5 Hz: 2H)].

Tert-Butyl N-[(1R)-1-hydroxymethyl-2-(1-oxy-4-pyridyl)ethyl]carbamate: 1 g of tert-butyl (1R)-1-(4-pyridylmethyl)-2-hydroxyethylcarbamate in 5 cm³ of dichloromethane is added to a solution of 1.01 g of 77% m-chloroperbenzoic acid in 10 cm³ of dichloromethane, and the mixture is then heated to a temperature in the region of 60° C. After 45 minutes, a further 0.65 g of m-chloroperbenzoic acid is added and the mixture is heated for 1 hour at a temperature in the region of 60° C., and the above operation is then repeated. After heating for 2 hours at a temperature in the region of 60° C., the reaction medium is cooled and then taken up in 50 cm³ of dichloromethane and 50 cm³ of 1N sodium hydroxide. The aqueous phase is concentrated under reduced pressure (1 kPa) at a temperature in the region of 40° C., taken up in 50 cm³ of dichloromethane, dried over magnesium sulfate, filtered and concentrated under reduced pressure (1 kPa) at a temperature in the region of 40° C. 0.15 g of tert-butyl N-[(1R)-1-hydroxymethyl-2-(1-oxy-4-pyridyl)ethyl]carbamate is obtained [¹H NMR spectrum (300 MHz, (CD₃)₂SO-d₆, δ in ppm): 1.32 (s: 9H); from 2.45 to 2.60 (mt: 1H); 2.86 (very broad d, J=13.5 Hz: 1H); from 3.20 to 3.45 (mt: 2H); 3.63 (mt: 1H); 4.80 (mt: 1H); 6.67 (broad d, J=9 Hz: 1H); 7.23 (broad d, J=5.5 Hz: 2H); 8.14 (broad d, J=5.5 Hz: 2H)].

EXAMPLE 31

(+)-4-(1,2,4-Triazol-1-ylmethyl)-4,5-dihydro-2-thiazol-ylamine dihydrochloride

A racemic mixture of 0.35 g of (4RS)-4-(1,2,4-triazol-1-ylmethyl-4,5-dihydro-2-thiazolylamine dihydrochloride is separated on a Chiralpak AS 20μ column in a heptane/ethanol/triethylamine mixture (80/20/0.1 by volume). The fractions containing the expected product are combined and then concentrated under reduced pressure (1 kPa) at a temperature in the region of 40° C. to give 0.08 g of (+)-4-(1,2,4-triazol-1-ylmethyl)-4,5-dihydro-2-thiazolylamine dihydro-chloride in the form of a yellow solid [¹H NMR spectrum (300 MHz, (CD₃)₂SO-d₆, δ in ppm): 3.46 (dd, J=11.5 and 4.5 Hz: 1H); 3.76 (dd, J=11.5 and 8.5 Hz: 1H); 4.51 (d, J=5 Hz: 2H); 4.69 (mt: 1H); 8.13 (broad s: 1H); 8.68 (broad s: 1H); 9.30 (unresolved complex: 1H); 9.73 (unresolved complex: 1H); 10.10 (broad s: 1H), ($\alpha_D^{20}$=+13.2+/-0.7 at a concentration of 0.5% in methanol)].

(4RS)-4-(1,2,4-Triazol-1-ylmethyl)-4,5-dihydro-2-thiazolylamine dihydrochloride: a solution of 0.3 g of tert-butyl N-[(4RS)-4-(1,2,4-triazol-1-yl-methyl)-4,5-dihydro-2-thiazolyl]carbamate in 10 cm³ of 4N hydrochloric acid in dioxane is stirred at a temperature in the region of 20° C. for 34 hours. The reaction medium is filtered and then washed with 3 times 5 cm³ of diethyl ether and dried in a desiccator. 0.14 g of (4RS)-4-(1,2,4-triazol-1-ylmethyl)-4,5-dihydro-2-thiazolylamine dihydrochloride is obtained in the form of a white foam [mass spectrum: EI m/z=184 MH⁺ m/z=183 M⁺ m/z=114 C₄H₆N₂⁺ M/z=101 C₃H₅N₂S⁺ base peak m/z=36 HCl DCI m/z=184 MH⁺].

Tert-Butyl N-[(4RS)-4-(1,2,4-triazol-1-yl-methyl)-4,5-dihydro-2-thiazolyl]carbamate: 0.6 g of 1,2,4-triazole is added, at a temperature in the region of 20° C. and under an inert atmosphere, to a solution of 0.35 g of sodium hydride in 7 cm³ of dimethyl sulfoxide. The mixture is stirred at a temperature in the region of 20° C. for 45 minutes, followed by addition of 1 g of tert-butyl N-[(4RS)-4-(iodomethyl)-4,5-dihydro-2-thiazolyl]carbamate. After stirring for 3 hours at a temperature in the region of 60° C., 30 cm³ of saturated ammonium chloride solution are added to the reaction medium and the resulting mixture is extracted with 4 times 10 cm³ of ethyl acetate. The organic phases are washed with 10 cm³ of saturated sodium chloride solution, dried over magnesium sulfate, filtered and then concentrated under reduced pressure (1 kPa) at a temperature in the region of 40° C. The residue is chromatographed under an argon pressure of 70 kPa on a column of silica gel (particle size 40–63μ; diameter 4 cm; height 18 cm), eluting with a dichloromethane/methanol mixture (5/1 by volume). The fractions containing the expected product are combined and then concentrated under the above conditions. 0.34 g of tert-butyl N-[(4RS)-4-(1,2,4-triazol-1-ylmethyl)-4,5-dihydro-2-thiazolyl]carbamate is obtained in the form of a white foam [mass spectrum: EI m/z=283 M⁺. m/z=201 C₈H₁₃N₂O₂S⁺ m/z=145 C₄H₅N₂O₂S⁺ m/z=101 C₃H₅N₂S⁺ m/z=82 C₃H₄N₃⁺ m/z=57 C₄H₉⁺].

Tert-Butyl N-[(4RS)-4-(iodomethyl)-4,5-dihydro-2-thiazolyl]carbamate: 17 g of sodium bicarbonate are added, at a temperature in the region of 20° C., to a suspension of 25.4 g of tert-butyl allylsulfanyl-[(tert-butoxycarbonyl)amino]methylidene-carbamate in 650 cm³ of dichloromethane, followed by addition of a solution of 24.4 g of iodine predissolved in 850 cm³ of dichloromethane. After 72 hours at a temperature in the region of 20° C., 500 cm³ of water and 500 cm³ of saturated sodium bicarbonate solution are added to the reaction medium and the resulting mixture is then extracted with twice 1 dm³ of ethyl acetate. The organic phases are washed with saturated sodium sulfite solution and then with saturated sodium chloride solution, dried over magnesium sulfate, filtered and then concentrated under reduced pressure (1 kPa) at a temperature in the region of 50° C. The residue obtained is crystallized from ethyl acetate. 20.5 g of tert-butyl N-[(4RS)-4-(iodomethyl)-4,5-dihydro-2-thiazolyl]carbamate are obtained in the form of a yellow solid [¹H NMR spectrum (300 MHz, (CD₃)₂SO-d₆, δ in ppm): 1.41 (s: 9H); 2.97 (dd, J=11.5 and 7 Hz: 1H); from 3.30 to 3.50 (mt: 3H); 4.12 (mt: 1H); 9.89 (unresolved complex: 1H)].

Tert-Butyl allylsulfanyl-[(tert-butoxycarbonyl)amino]methylidenecarbamate: a catalytic amount of 4-(dimethylamino)pyridine and 4.7 cm³ of triethylamine are added to a solution of 5 g of 2-allylisothiourea hydrochloride in 50 cm³ of dichloromethane, followed by dropwise addition of a solution of 7.1 g of di-tert-butyl dicarbonate predissolved in 30 cm³ of dichloromethane. After 48 hours, the reaction medium is concentrated under reduced pressure (1 kPa) at a temperature in the region of 40° C. The residue is chromatographed under an argon pressure of 70 kPa, on a column of silica gel (particle size 40–63μ; diameter 4 cm; height about 30 cm), eluting with an ethyl acetate/cyclohexane mixture (90/10 by volume). The fractions containing the expected product are combined and then concentrated under the above conditions. 0.2 g of tert-butyl allylsulfanyl-[(tert-butoxycarbonyl)amino]methylidene-carbamate is obtained [mass spectrum: DCI m/z=317 MH⁺ m/z=261 C₁₀H₁₇O₄N₂S⁺ m/z=217 C₉H₁₇O₂N₂S⁺ m/z=161 C₅H₉O₂N₂S⁺].

2-Allylisothiourea hydrochloride: 16 cm³ of allyl chloride are added, at a temperature in the region of 20° C., to a suspension of 15 g of thiourea in 120 cm³ of ethanol. After 15 hours at a temperature in the region of 80° C., the reaction medium is concentrated under reduced pressure (1 kPa) at a temperature in the region of 50° C. The solid obtained is taken up in 3 times 100 cm³ of diethyl ether and then filtered. 29 g of 2-allylisothiourea hydrochloride are obtained in the form of a white solid [mass spectrum: DCI m/z=117 MH⁺].

EXAMPLE 32

(+)-(4R,5R)-5-(Ethyl-4-(4-pyridylmethyl)-4,5-dihydro-2-thiazolylamine

A suspension of 4.2 g of N-tert-butyl-N'-[(1R,2S)-1-(4-pyridylmethyl)-2-hydroxybutyl]thiourea in 40 cm³ of 6N hydrochloric acid is heated at a temperature in the region of 100° C. for 20 hours. After cooling to room temperature, the reaction mixture is concentrated under reduced pressure (1 kPa) at a temperature in the region of 50° C. The residue is chromatographed at atmospheric pressure on a column of silica gel (particle size 40–63μ; diameter 3.6 cm; height 24 cm), eluting with a dichloromethane/methanol mixture (98/2 by volume) and then with a dichloro-methane/methanol mixture (97/3 by volume). The fractions containing the expected product are combined and then concentrated under the above conditions, taken up in 30 cm³ of dichloromethane and basified with 1N sodium hydroxide. The organic phase is dried over magnesium sulfate, filtered and dried in a desiccator under reduced pressure (0.1 kPa) at a temperature in the region of 40° C. 1.4 g of (+)-(4R,5R)-5-(ethyl-4-(4-pyridylmethyl)-4,5-dihydro-2-thiazolylamine are obtained in the form of a white solid melting at 124° C. [$^1$H NMR spectrum (300 MHz, $(CD_3)_2SO-d_6$, δ in ppm): 0.83 (t, J=7.5 Hz: 3H); 1.43 (mt: 1H); 1.61 (mt: 1H); 2.70 (limiting AB: 2H); 3.40 (mt: 1H); 4.08 (mt: 1H); 6.28 (unresolved complex: 2H); 7.29 (broad d, J=5.5 Hz: 2H); 8.45 (broad d, J=5.5 Hz: 2H), $(α_D^{20}$=+166.9+/−2.4 at a concentration of 0.5% in methanol)].

N-tert-Butyl-N'-[(1R,2S)-1-(4-pyridylmethyl)-2-hydroxybutyl]thiourea: 4.3 cm³ of triethylamine are added to a solution of 3.6 g of (2R,3S)-2-amino-1-(4-pyridyl)-3-pentanol dihydrochloride in 60 cm³ of ethanol, followed by addition of 2.6 cm³ of tert-butyl isothiocyanate. The mixture is heated at a temperature in the region of 50° C. for 18 hours. After cooling, the reaction medium is concentrated under reduced pressure (1 kPa) at a temperature in the region of 40° C. and the residue is taken up in 50 cm³ of water and 100 cm³ of dichloromethane. The organic phase is washed with 30 cm³ of water, dried over sodium sulfate, filtered and concentrated under the above conditions. 4.3 g of N-tert-butyl-N'-[(1R,2S)-1-(4-pyridylmethyl)-2-hydroxybutyl]thiourea are obtained in the form of a thick colorless oil [$^1$H NMR spectrum (300 MHz, $(CD_3)_2SO-d_6$, δ in ppm): 0.80 (t, J=7.5 Hz: 3H); from 1.25 to 1.55 (mt: 2H); 1.37 (s: 9H); 2.72 (dd, J=14 and 9 Hz: 1H); 2.93 (dd, J=14 and 4.5 Hz: 1H); 3.37 (mt: 1H); 4.60 (mt: 1H); 4.88 (unresolved complex: 1H); 7.11 (s: 1H); 7.16 (d, J=8.5 Hz: 1H); 7.26 (broad d, J=5.5 Hz: 2H); 8.43 (broad d, J=5.5 Hz: 2H)].

(2R,3S)-2-Amino-1-(4-pyridyl)-3-pentanol dihydrochloride: a solution of 50 cm³ of 4N hydrochloric acid in dioxane is added, with stirring and at a temperature in the region of 20° C., to a solution of 4 g of tert-butyl N-[(1R,2S)-2-hydroxy-1-(4-pyridylmethyl)-butyl]carbamate in 50 cm³ of dioxane. The mixture is stirred at a temperature in the region of 20° C. for 18 hours and is then concentrated under reduced pressure (1 kPa) at a temperature in the region of 60° C. 3.6 g of (2R,3S)-2-amino-1-(4-pyridyl)-3-pentanol dihydrochloride are obtained in the form of a white solid [$^1$H NMR spectrum (300 MHz, $(CD_3)_2SO-d_6$, δ in ppm): 0.92 (t, J=7.5 Hz: 3H); from 1.30 to 1.65 (mt: 2H); 3.13 (dd, J=14 and 9 Hz: 1H); 3.28 (dd, J=14 and 5 Hz: 1H); 3.52 (mt: 1H); 3.68 (mt: 1H); 8.11 (broad d, J=6.5 Hz: 2H); 8.25 (unresolved complex: 3H); 8.90 (broad d, J=6.5 Hz: 2H)].

Tert-Butyl N-[(1R,2S)-2-hydroxy-1-(4-pyridylmethyl)butyl]carbamate: 9.5 g of an 85%/15% mixture of the two diastereoisomers of tert-butyl N-[(2RS)-2-hydroxy-(1R)-1-(4-pyridylmethyl)butyl]carbamate is separated on a Kromasil® 10μ C8 column in an acetonitrile/methanol/tetrahydrofuran/water mixture (15/15/5/65 by volume). The fractions containing the expected product are concentrated under reduced pressure (1 kPa) at a temperature in the region of 40° C. to give 4 g of tert-butyl N-[(1R,2S)-2-hydroxy-1-(4-pyridylmethyl)butyl]carbamate dihydrochloride in the form of a white solid [$^1$H NMR spectrum (300 MHz, $(CD_3)_2SO-d_6$, δ in ppm): 0.91 (t, J=7.5 Hz: 3H); 1.26 (s: 9H); 1.30 (mt: 1H); 1.52 (mt: 1H); from 2.45 to 2.60 (mt: 1H); 3.02 (dd, J=14 and 3.5 Hz: 1H); 3.28 (mt: 1H); 3.53 (mt: 1H); 4.71 (d, J=6 Hz: 1H); 6.62 (d, J=9.5 Hz: 1H); 7.20 (broad d, J=5.5 Hz: 2H); 8.42 (broad d, J=5.5 Hz: 2H)].

Tert-Butyl N-[(2RS)-2-hydroxy-(1R)-1-(4-pyridylmethyl)butyl]carbamate: 2.1 g of sodium borohydride are added, with stirring and at a temperature in the region of 10° C., to a solution of 10.5 g of tert-butyl N-[(1R)-2-oxobutyl-1-(4-pyridyl-methyl)]carbamate in 150 cm³ of ethanol, and the mixture is then stirred at a temperature in the region of 20° C. for 18 hours. The reaction medium is concentrated under reduced pressure (1 kPa) at a temperature in the region of 40° C., taken up in 100 cm³ of water and extracted with 200 cm³ of ethyl acetate. The organic phase is dried over magnesium sulfate, filtered and concentrated under reduced pressure (1 kPa) at a temperature in the region of 40° C. 9.5 g of an 85%/15% mixture of the two diastereoisomers of tert-butyl N-[(2RS)-2-hydroxy-(1R)-1-(4-pyridylmethyl)butyl]carbamate are obtained in the form of a yellow gum [$^1$H NMR spectrum (300 MHz, $(CD_3)_2SO-d_6$, δ in ppm). We observe a mixture of two diastereoisomers in proportions of 85/15; δ=from 0.85 to 0.95 (mt: 3H); from 1.25 to 1.60 (mt: 2H); 1.26 and 1.29 (2s: 9H in total); from 2.45 to 2.60 (mt: 0.85H); 2.67 (dd, J=14 and 10 Hz: 0.15H); 2.80 (dd, J=14 and 4.5 Hz: 0.15H); 3.02 (dd, J=14 and 4.5 Hz: 0.85H); from 3.20 to 3.35 (mt: 1H); 3.52 (mt: 0.85H); 3.69 (mt: 0.15H); 4.61 (d, J=6 Hz: 0.15H); 4.71 (d, J=6 Hz: 0.85H); 6.41 (d, J=9.5 Hz: 0.15H); 6.62 (d, J=9.5 Hz: 0.85H); 7.20 (d, J=6 Hz: 1.7H); 7.23 (d, J=6 Hz: 0.3H); from 8.35 to 8.50 (mt: 2H in total)].

Tert-Butyl N-[(1R)-2-oxo-(4-pyridylmethyl)-butyl]carbamate: 50 cm³ of a 3N solution of ethyl magnesium bromide dissolved in diethyl ether are added over 1 hour to a mixture, under an inert atmosphere, of 14 g of tert-butyl N-{2-[N-methoxy-N-(methyl)amino]-2-oxo-(1R)-1-(4-pyridylmethyl)ethyl}carbamate in 350 cm³ of tetrahydrofuran, cooled to a temperature in the region of 0° C. After stirring for 48 hours at 0° C., water is added to the reaction medium, the resulting mixture is extracted with dichloromethane and the extracts are washed with water. The organic phase is dried over sodium sulfate, filtered and then concentrated under reduced pressure (2 kPa) at a temperature in the region of 40° C. 10.5 g of tert-butyl N-[(1R)-2-oxo-1-(4-pyridylmethyl)butyl]carbamate are obtained in the form of a yellow oil [$^1$H NMR spectrum (300 MHz, $(CD_3)_2SO-d_6$, δ in ppm): 0.94 (t, J=7 Hz: 3H); 1.32 (s: 9H); from 2.40 to 2.65 (mt: 2H); 2.70 (dd, J=14 and 10.5 Hz: 1H); 3.06 (dd, J=14 and 4.5 Hz: 1H); 4.22 (mt: 1H); 7.26 (broad d, J=5.5 Hz: 2H); 7.44 (broad d, J=8 Hz: 1H); 8.45 (broad d, J=5.5 Hz: 2H)].

EXAMPLE 33

(4R)-4-(2-Thienylmethyl)-4,5-dihydro-2-thiazolylamine hydrochloride 0.9 cm$^3$ (9.4 mmol) of ethyl chloroformate is added dropwise to a solution of 2.5 g (9.23 mmol) of Boc-D-2-thienylalanine and 1.3 cm$^3$ (9.4 mmol) of triethylamine in 100 cm$^3$ of anhydrous tetrahydrofuran at −20° C. The resultant suspension is stirred at −20° C. for 1 hour and then filtered. The filtrate is cooled to −20° C. and a solution of 0.71 g (20.9 mmol) of sodium borohydride in 5 cm$^3$ of water is then added. The reaction mixture is stirred at a temperature in the region of 20° C. for 64 hours and is then concentrated under vacuum to give a residue which is used directly without purification. A suspension of the product obtained in 20 cm$^3$ of dioxane is treated with 6 cm$^3$ of a 4M solution of hydrochloric acid in dioxane and is then stirred at a temperature in the region of 20° C. for 16 hours. After concentrating the reaction medium under vacuum, 7.5 g of a white solid are obtained and are used directly without purification.

A suspension of the above product (1.0 g), triethylamine (4 cm$^3$, 28.7 mmol) and tert-butyl isothiocyanate (0.50 g, 4.3 mmol) in 10 cm$^3$ of ethanol is heated at a temperature in the region of 50° C. for 4 hours with stirring. After concentrating under vacuum, the residue is taken up twice in 50 cm$^3$ of ethyl acetate and is then purified by chromatography on a column of silica gel (ethyl acetate/cyclohexane 1/1 by volume). The fractions containing the expected product are concentrated under reduced pressure to give 255 mg of a white solid which is used directly.

A suspension of the product obtained above (240 mg, 0.88 mmol) is refluxed in 6 cm$^3$ of 6N hydrochloric acid solution for 8 hours. The reaction mixture is concentrated to dryness under vacuum and the brown residue is slurried in a mixture of ethanol (5 cm$^3$) and ethyl acetate (3 cm$^3$) and then filtered. This slurrying operation is repeated 3 times, until a clear yellow solution is obtained. After partial concentration, the product crystallizes and is filtered off and then dried under vacuum to give 64 mg of (4R)-4-(2-thienylmethyl)-4,5-dihydro-2-thiazolylamine hydrochloride in the form of pale yellow crystals melting at 125–127° C. [$^1$H NMR spectrum (300 MHz, (CD$_3$)$_2$SO-d$_6$, δ in ppm): 10.1 (bs, 1H), 9.7 (bs, 1H), 9.3 (bs, 1H), 7.4 (m, 1H), 7.0 (m, 2H), 4.5 (m, 1H), 3.6 (m, 1H), 3.3 (m, 1H), 3.2 (m, 2H)].

The pharmaceutical compositions according to the invention consist of a compound of formula (I) or an isomer or tautomer or salt of such a compound, in pure form or in the form of a composition in which it is combined with any other pharmaceutically compatible product, which may be inert or physiologically active. The medicinal products according to the invention may be used orally, parenterally, rectally or topically.

Solid compositions for oral administration which can be used include tablets, pills, powders (gelatin capsules, cachets) or granules. In these compositions, the active principle according to the invention is mixed with one or more inert diluents, such as starch, cellulose, sucrose, lactose or silica, under a stream of argon. These compositions can also comprise substances other than diluents, for example one or more lubricants such as magnesium stearate or talc, a dye, a coating (dragee) or a varnish.

Liquid compositions for oral administration which can be used include pharmaceutically acceptable solutions, suspensions, emulsions, syrups and elixirs containing inert diluents such as water, ethanol, glycerol, plant oils or liquid paraffin. These compositions can comprise substances other than diluents, for example wetting products, sweeteners, thickeners, flavorings or stabilizers.

The sterile compositions for parenteral administration can preferably be aqueous or non-aqueous solutions, suspensions or emulsions. Solvents or vehicles which may be used include water, propylene glycol, a polyethylene glycol, plant oils, in particular olive oil, injectable organic esters, for example ethyl oleate, or other suitable organic solvents. These compositions can also contain adjuvants, in particular wetting agents, isotonic agents, emulsifiers, dispersants and stabilizers. The sterilization can be carried out in several ways, for example by aseptic filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semisynthetic glycerides or polyethylene glycols.

Compositions for topical administration can be, for example, creams, lotions, eye drops, mouth washes, nasal drops or aerosols.

In human therapy, the compounds according to the invention are particularly useful for treating and/or preventing multiple sclerosis, cerebral, focal or global ischemia, cerebral or spinal trauma, Parkinson's disease, Huntington's diseases, Alzheimer's disease, amyotrophic lateral sclerosis, migraine, depression, schizophrenia, anxiety, epilepsy, diabetes, atherosclerosis, myocarditis, arthritis, arthrosis, asthma, irritable bowel syndrome, Crohn's disease, peritonitis, gastro-esophageal reflux, uveitis, Guillain-Barré0 syndrome, glomerulonephritis, lupus erythematosus, psoriasis, the growth of certain forms of tumors such as, for example, epithelioma, adenocarcinoma or sarcoma, and in infections with Gram-positive or Gram-negative intracellular or extracellular bacteria.

The doses depend on the desired effect, the duration of the treatment and the route of administration used; they are generally between 1 mg and 100 mg per day via the oral route for an adult, with unit doses ranging from 0.5 mg to 50 mg of active substance.

In general, the doctor will determine the appropriate dosage as a function of the age, weight and all the other personal factors of the individual to be treated.

The examples which follow illustrate compositions according to the invention:

Example A

Gel capsules containing a 50 mg dose of active product and having the composition below are prepared, according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

Example B

Tablets containing a 50 mg dose of active product and having the composition below are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |

Mixture of hydroxymethylcellulose, glycerol and titanium oxide (72/3.5/24.5) qs 1 finished film-coated tablet weighing 245 mg.

Example C

An injectable solution containing 10 mg of active product and having the composition below is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water | qs 4 ml |

The present invention also relates to the method for preventing and treating diseases in which an abnormal production of nitric oxide (NO) by induction of inducible NO-synthase (NOS-2 or iNOS) is involved by administration of a compound of formula (I), racemic mixtures, enantiomers and diastereoisomers thereof and mixtures thereof, the tautomer thereof or pharmaceutically acceptable salts thereof.

What is claimed is:

1. A compound of the formula (I):

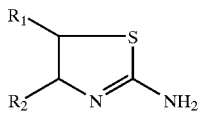

(I)

wherein $R_1$ is hydrogen or $C_{1-6}$alkyl; and $R_2$ is —$CH_2$—$R_3$; and wherein $R_3$ is thienyl, thiazolyl, imidazolyl, or triazolyl;

or a racemic mixture, an enantiomer, a diastereoisomer or a mixture thereof, or a tautomer thereof, or a pharmaceutically acceptable salt thereof.

2. The compound according to claim 1, wherein $R_3$ is thienyl or imidazolyl.

3. The compound according to claim 1, wherein $R_3$ is 2 or 3- thienyl, 4- or 5-thiazolyl, 1-imidazolyl or 1-triazolyl.

4. The compound according to claim 2, wherein $R_3$ is 2 or 3- thienyl or 1-imidazolyl.

5. The compound according to claim 1, which is chosen from the following:
4-(3-thienylmethyl)-4,5-dihydro-1,3-thiazol-2-ylamine,
4-(2-thienylmethyl)-4,5-dihydro-1,3-thiazol-2-ylamine,
4-(4-thiazolylmethyl)-4,5-dihydro-1,3-thiazol-2-ylamine,
4-(1-imidazolylmethyl)-4,5-dihydro-1,3-thiazol-2-ylamine,
4-(5-thiazolylmethyl)-4,5-dihydro-1,3-thiazol-2-ylamine,
4-(1-triazolylmethyl)-4,5-dihydro-1,3-thiazol-2-ylamine,
or a racemic mixture, an enantiomer, a diastereoisomer or a mixture thereof, or a tautomer thereof, or a pharmaceutically acceptable salt thereof.

6. The compound according to claim 1, which is chosen from the following:
(−)-(4R)-4-(3-thienylmethyl)-4,5-dihydro-1,3-thiazol-2-ylamine,
(4R)-4-(2-thienylmethyl)-4,5-dihydro-1,3-thiazol-2-ylamine,
(+)-4-(5-thiazolylmethyl)-4,5-dihydro-1,3-thiazol-2-ylamine,
(−)-4-(5-thiazolylmethyl)-4,5-dihydro-1,3-thiazol-2-ylamine,
(4R)-4-(1-imidazolylmethyl)-4,5-dihydro-1,3-thiazol-2-ylamine,
(4S)-4-(1-imidazolylmethyl)-4,5-dihydro-1,3-thiazol-2-ylamine,
(+)-(4R)-4-(4-thiazolylmethyl)-4,5-dihydro-1,3-thiazol-2-ylamine,
(+)-4-(1-triazolylmethyl)-4,5-dihydro-1,3-thiazol-2-ylamine,
or a tautomer thereof, or a pharmaceutically acceptable salt thereof.

7. The compound according to claim 2, which is chosen from the following:
4-(3-thienylmethyl)-4,5-dihydro-1,3-thiazol-2-ylamine,
4-(2-thienylmethyl)-4,5-dihydro-1,3-thiazol-2-ylamine,
4-(1-imidazolylmethyl)-4,5-dihydro-1,3-thiazol-2-ylamine,
or a racemic mixture, an enantiomer, a diastereoisomer or a mixture thereof, or a tautomer thereof, or a pharmaceutically acceptable salt thereof.

8. The compound according to claim 2, which is chosen from the following:
(−)-(4R)-4-(3-thienylmethyl)-4,5-dihydro-1,3-thiazol-2-ylamine,
(4R)-4-(2-thienylmethyl)-4,5-dihydro-1,3-thiazol-2-ylamine,
(4R)-4-(1-imidazolylmethyl)-4,5-dihydro-1,3-thiazol-2-ylamine,
(4S)-4-(1-imidazolylmethyl)-4,5-dihydro-1,3-thiazol-2-ylamine,
or a tautomer thereof, or a pharmaceutically acceptable salt thereof.

9. A pharmaceutical composition comprising, as active ingredient, at least one compound of formula (I):

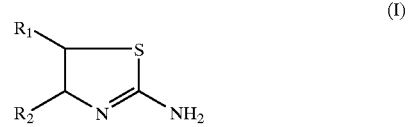

(I)

wherein $R_1$ is hydrogen or $C_{1-6}$alkyl; and $R_2$ is —$CH_2$—$R_3$; and wherein $R_3$ is thienyl, thiazolyl, imidazolyl, or triazolyl;

or a racemic mixture, an enantiomer, a diastereoisomer or a mixture thereof, or a tautomer thereof, or a pharmaceutically acceptable salt thereof.

10. The composition according to claim 9 wherein $R_3$ is thienyl or imidazolyl.

11. The composition according to claim 9, wherein $R_3$ is 2 or 3-thienyl, 4- or 5-thiazolyl, 1-imidazolyl or 1-triazolyl.

12. The composition according to claim 10, wherein $R_3$ is 2 or 3-thienyl or 1-imidazolyl.

13. The composition according to claim 9 wherein said compound is selected from the group consisting of:
4-(3-thienylmethyl)-4,5-dihydro-1,3-thiazol-2-ylamine, 4-(2-thienylmethyl)-4,5-dihydro-1,3-thiazol-2-ylamine,
4-(4-thiazolylmethyl)-4,5-dihydro-1,3-thiazol-2-ylamine,
4-(1-imidazolylmethyl)-4,5-dihydro-1,3-thiazol-2-ylamine,
4-(5-thiazolylmethyl)-4,5-dihydro-1,3-thiazol-2-ylamine, and
4-(1-triazolylmethyl)-4,5-dihydro-1,3-thiazol-2-ylamine,
or a racemic mixture, an enantiomer, a diastereoisomer or a mixture thereof, or a tautomer thereof, or a pharmaceutically acceptable salt thereof.

14. The composition according to claim 9 wherein said compound is selected from the group consisting of:
(−)-(4R)-4-(3-thienylmethyl)-4,5-dihydro-1,3-thiazol-2-ylamine,
(4R)-4-(2-thienylmethyl)-4,5-dihydro-1,3-thiazol-2-ylamine,
(+)-4-(5-thiazolylmethyl)-4,5-dihydro-1,3-thiazol-2-ylamine,
(−)-4-(5-thiazolylmethyl)-4,5-dihydro-1,3-thiazol-2-ylamine,
(4R)-4-(1-imidazolylmethyl)-4,5-dihydro-1,3-thiazol-2-ylamine,
(4S)-4-(1-imidazolylmethyl)-4,5-dihydro-1,3-thiazol-2-ylamine,
(+)-(4R)-4-(4-thiazolylmethyl)-4,5-dihydro-1,3-thiazol-2-ylamine, and
(+)-4-(1-triazolylmethyl)-4,5-dihiydro-1,3-thiazol-2-ylamine,
or a tautomer thereof, or a pharmaceutically acceptable salt thereof.

15. The composition according to claim 10 wherein said compound is selected from the group consisting of:
4-(3-thienylmethyl)-4,5-dihydro-1,3-thiazol-2-ylamine,
4-(2-thienylmethyl)-4,5-dihydro-1,3-thiazol-2-ylamine, and
4-(1-imidazolylmethyl)-4,5-dihydro-1,3-thiazol-2-ylamine,
or a racemic mixture, an enantiomer, a diastereoisomer or a mixture thereof, or a tautomer thereof, or a pharmaceutically acceptable salt thereof.

16. The composition according to claim 10 wherein said compound is selected from the group consisting of:
(−)-(4R)-4-(3-thienylmethyl)-4,5-dihydro-1,3-thiazol-2-ylamine,
(4R)-4-(2-thienylmethyl)-4,5-dihydro-1,3-thiazol-2-ylamine,
(4R)-4-(1-imidazolylmethyl)-4,5-dihydro-1,3-thiazol-2-ylamine,
(4S)-4-(1-imidazolylmethyl)-4,5-dihydro-1,3-thiazol-2-ylamine,
or a tautomer thereof, or a pharmaceutically acceptable salt thereof.

17. A process for preparing a compound of formula (I), including a racemic mixture, an enantiomer, a diastereoisomer or a mixture of said enantiomer or said diastereomer, or a tautomer thereof:

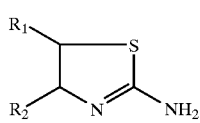
(I)

comprising the step of cyclizing a compound of formula (II) under suitable acidic reaction conditions such that said compound of formula (II) cyclizes to form said compound of formula (I);

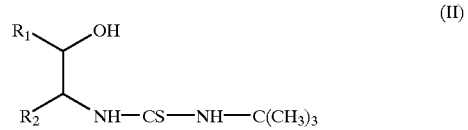
(II)

and isolating said compound of formula (I); wherein
$R_1$ is hydrogen or $C_{1-6}$alkyl; and
$R_2$ is —$CH_2$—$R_3$; and wherein
$R_3$ is thienyl, thiazolyl, imidazolyl, or triazolyl.

18. The process according to claim 17 wherein said process includes an additional step comprising
converting said compound of formula (I) into a pharmaceutically acceptable salt by way of a reaction of said compound with a suitable inorganic or organic acid.

19. A process for the preparation of the compound of formula (II) as defined in claim 17 and in which $R_1$ is hydrogen, comprising the steps of:
reacting a compound of formula (IIa)

(IIa)

with a suitable reducing agent under suitable reaction conditions to form the compound of formula (IIb)

(IIb)

reacting said compound of formula (IIb) with a suitable deprotecting agent to form a compound of formula (IIc)

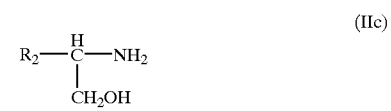
(IIc)

reacting said compound of formula (IIc) with tert-butyl thiocyanate to form said compound of formula (II); wherein
$R_2$ is as defined in claim 17; and
Ra is either hydrogen or an amino protecting group.

20. A process for preparing a compound of formula (I) according to claim 1, for which $R_2$ is —$CH_2$—$R_3$ wherein $R_3$ is 1-imidazolyl or 1-(1,2,4-triazolyl) radical, comprising the step of reacting imidazole or 1,2,4-triazole with a derivative of formula (IV):

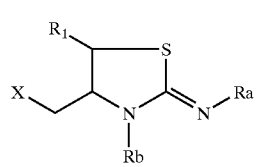
(IV)

wherein $R_1$ has the same meaning as in claim 1, X is halogen or tosyl radical and Ra and Rb are hydrogen or protecting groups for the amine function, optionally followed by a deprotection, and isolating the product.

21. The process according to claim 20 wherein said process includes an additional step comprising converting said compound of formula (I) into a pharmaceutically acceptable salt by way of a reaction of said compound with a suitable inorganic or organic acid.

* * * * *